(12) United States Patent
Hoium et al.

(10) Patent No.: US 6,512,945 B1
(45) Date of Patent: Jan. 28, 2003

(54) METHOD OF NONINVASIVELY DETERMINING A PATIENT'S SUSCEPTIBILITY TO ARRHYTHMIA

(75) Inventors: Harold H. Hoium, Eden Prairie, MN (US); Stephen J. Ryan, Chaska, MN (US); Marek Malik, London (GB)

(73) Assignee: Harbinger Medical, Inc., Eden Prairie, MN (US)

(*) Notice: Subject to any disclaimer, the term of this patent is extended or adjusted under 35 U.S.C. 154(b) by 70 days.

(21) Appl. No.: 09/590,965

(22) Filed: Jun. 9, 2000

Related U.S. Application Data

(60) Provisional application No. 60/191,029, filed on Mar. 21, 2000, provisional application No. 60/138,497, filed on Jun. 10, 1999, and provisional application No. 60/138,439, filed on Jun. 10, 1999.

(51) Int. Cl.$^7$ .............................................. A61B 5/0452
(52) U.S. Cl. ....................................... 600/515; 600/518
(58) Field of Search ................................. 600/515, 518

(56) References Cited

U.S. PATENT DOCUMENTS 5,117,834 A     6/1992   Kroll ........................ 128/705
5,555,888 A  *  9/1996   Brewer et al. .............. 128/702

FOREIGN PATENT DOCUMENTS

GB      2301037 A      11/1996     ............ A61N/1/37
WO      9905964 A       2/1999     ............ A61B/5/04

* cited by examiner

*Primary Examiner*—Carl Layno
(74) *Attorney, Agent, or Firm*—Patterson, Thuente, Skaar & Christensen, P.A.

(57) ABSTRACT

A system and method for detecting a patient's susceptibility to arrhythmias and cardiac tissue abnormality is disclosed. The method consists of using a computer 27, a display 23, software loaded onto the computer that generates graphical user interfaces (GUIs), an electronic interface 18, and a plurality of electrodes. The electronics interface 18 is in electronic communication with the computer 27, and further in electronic communication with the electrodes that are placed by self-adhesion at predetermined locations on a test subject 35. According to one aspect of the invention, the method enables a user, typically a medical professional, to initiate, with minimal input, certain diagnostic tests involving observing and analyzing a series of QRS complexes 130, some of which are biased with a subpacing current, and others of which are unbiased. The signals are then compared, and the differences are analyzed to detect a patient's susceptibility to arrhythmias and cardiac tissue abnormality.

39 Claims, 79 Drawing Sheets

Protocol Steps

Protocol Information

| Step # | Pulses | Sensitivity | Deviation | uA | mS | Position | Ramp |
|---|---|---|---|---|---|---|---|
| 1 | 30 | Low | 15 | 0.00 | 0.50 | -20 | Off |
| 2 | 30 | Low | 15 | 20.00 | 0.50 | -20 | Off |
| 3 | 30 | Low | 15 | 0.00 | 2.00 | -20 | Off |
| 4 | 30 | Low | 15 | 20.00 | 2.00 | -20 | Off |
| 5 | 30 | Low | 15 | 0.00 | 0.50 | 0 | Off |
| 6 | 30 | Low | 15 | 20.00 | 0.50 | 0 | Off |
| 7 | 30 | Low | 15 | 0.00 | 2.00 | 0 | Off |
| 8 | 30 | Low | 15 | 20.00 | 2.00 | 0 | Off |
| 9 | 30 | Low | 15 | 0.00 | 0.50 | 20 | Off |
| 10 | 30 | Low | 15 | 20.00 | 0.50 | 20 | Off |
| 11 | 30 | Low | 15 | 0.00 | 2.00 | 20 | Off |
| 12 | 30 | Low | 15 | 20.00 | 2.00 | 20 | Off |

69

OK   Cancel

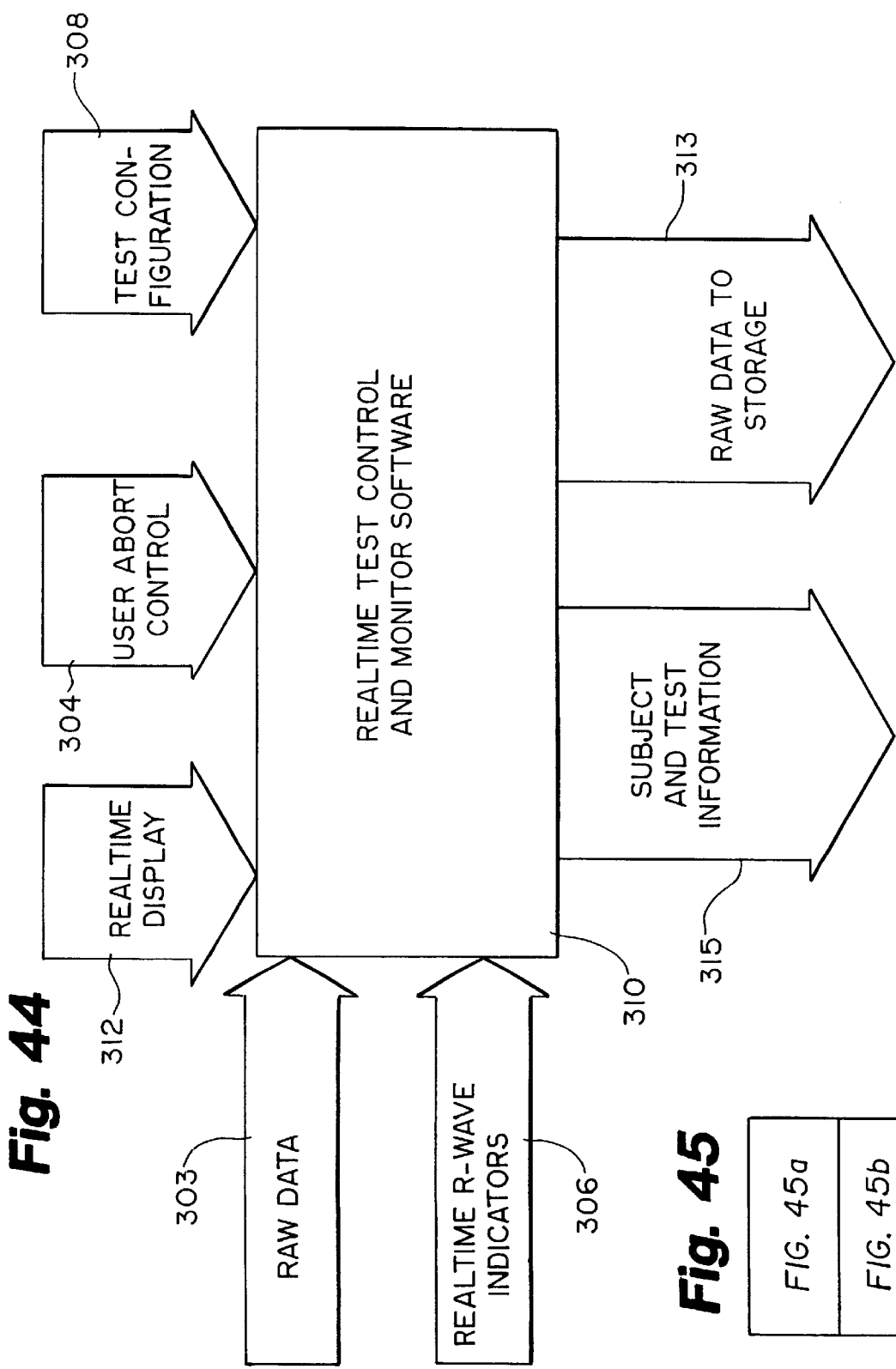

Fig. 54

INTERDEPENDENCE OF TIME-DOMAIN AND WAVELET DECOMPOSITION INDICES

|     | tQRS | LAS | RMS | WCL | WMC | WSA | WRL |
|-----|------|-----|-----|-----|-----|-----|-----|
| tQRS |     | 0.632 | -0.683 | 0.540 | 0.454 | 0.457 | -0.418 |
| LAS | p< $10^{-8}$ |  | -0.880 | 0.308 | 0.296 | 0.208 | -0.302 |
| RMS | p< $10^{-8}$ | $10^{-8}$ |  | -0.276 | -0.267 | -0.209 | 0.277 |
| WCL | p< $10^{-8}$ | $10^{-8}$ | $10^{-8}$ |  | 0.886 | 0.686 | -0.826 |
| WMC | p< $10^{-8}$ | $10^{-8}$ | $10^{-6}$ | $10^{-8}$ |  | 0.629 | -0.733 |
| WSA | p< $10^{-8}$ | $10^{-5}$ | $10^{-8}$ | $10^{-8}$ | $10^{-8}$ |  | -0.520 |
| WRL | p< $10^{-8}$ | $10^{-8}$ | $10^{-8}$ | $10^{-8}$ | $10^{-8}$ | $10^{-8}$ |  |

TABLE PRESENTS CORRELATION COEFFICIENT BETWEEN INDIVIDUAL TIME-DOMAIN AND WAVELET ANALYSIS INDICES.
THE VALUES OF CORRELATION COEFFICIENT ARE SHOWN ABOVE THE DIAGONAL, THE CORRESPONDING P-VALUES ARE DISPLAYED BELOW.

Fig. 55 COMPARISON OF SIGNAL-AVERAGED ECG INDICES IN PATIENTS WITH AND WITHOUT FOLLOW-UP EVENTS

| EVENT | INDEX | PATIENTS EVENT POSITIVE | EVENT NEGATIVE | $p^{**}$ |
|---|---|---|---|---|
| CARDIAC MORTALITY | tQRS<br>RMS40<br>LAS | 101.25±26.54<br>18.50±15.08<br>55.56±75.05 | 96.77±29.22<br>15.98±12.64<br>63.57±85.06 | 0.21<br>0.60<br>0.32 |
| | WCL<br>WMC<br>WSA<br>WRL | 155.66±29.45<br>244.91±67.00<br>4654.2±663.62<br>0.691±0.0822 | 146.13±22.42<br>223.50±56.51<br>4398.2±607.51<br>0.730±0.084 | $7.48 \times 10^{-3}$<br>$1.03 \times 10^{-2}$<br>$6.13 \times 10^{-3}$<br>$1.79 \times 10^{-2}$ |
| POTENTIALLY ARRHYTHMIC DEATH | tQRS<br>RMS40<br>LAS | 99.00±26.74<br>20.95±16.27<br>62.33±90.04 | 96.95±29.18<br>15.93±12.61<br>63.14±84.30 | 0.56<br>0.28<br>0.48 |
| | WCL<br>WMC<br>WSA<br>WRL | 158.10±34.34<br>248.29±76.48<br>4642.6±767.24<br>0.690±0.085 | 146.23±22.31<br>223.81±56.29<br>4404.0±605.16<br>0.729±0.0841 | $2.64 \times 10^{-2}$<br>$3.69 \times 10^{-2}$<br>$8.42 \times 10^{-2}$<br>$4.34 \times 10^{-2}$ |
| SUDDEN CARDIAC DEATH | tQRS<br>RMS40<br>LAS | 98.05±27.91<br>22.23±16.52<br>64.11±94.39 | 96.99±29.13<br>15.91±12.60<br>63.07±84.16 | 0.88<br>0.15<br>0.45 |
| | WCL<br>WMC<br>WSA<br>WRL | 158.95±35.85<br>248.68±79.86<br>4615.4±785.53<br>0.690±0.087 | 146.25±22.28<br>223.88±56.23<br>4405.9±605.55<br>0.729±0.084 | $3.72 \times 10^{-2}$<br>$6.13 \times 10^{-2}$<br>0.16<br>$5.42 \times 10^{-2}$ |
| VENTRICULAR TACHYCARDIA | tQRS<br>RMS40<br>LAS | 117.84±37.10<br>10.36±9.38<br>124.74±151.13 | 96.29±28.49<br>16.33±12.86<br>60.90±80.27 | $1.74 \times 10^{-3}$<br>$1.83 \times 10^{-2}$<br>$4.29 \times 10^{-3}$ |
| | WCL<br>WMC<br>WSA<br>WRL | 175.74±45.02<br>291.53±98.23<br>4783.8±1092.2<br>0.660±0.087 | 145.65±21.08<br>222.35±53.86<br>4399.9±585.3<br>0.730±0.083 | $3.84 \times 10^{-5}$<br>$2.85 \times 10^{-5}$<br>$3.47 \times 10^{-2}$<br>$1.10 \times 10^{-1}$ |
| ARRHYTHMIC EVENTS | tQRS<br>RMS40<br>LAS | 97.71±25.48<br>19.98±15.64<br>59.79±84.52 | 97.00±29.25<br>15.95±12.63<br>63.26±84.53 | 0.62<br>0.35<br>0.52 |
| | WCL<br>WMC<br>WSA<br>WRL | 156.29±32.81<br>245.88±72.50<br>4616.1±751.7<br>0.700±0.089 | 146.25±22.35<br>223.78±56.41<br>4403.9±605.2<br>0.729±0.084 | $3.43 \times 10^{-2}$<br>$2.92 \times 10^{-2}$<br>$8.44 \times 10^{-2}$<br>0.10 |
| ARRHYTHMIC FATALITIES | tQRS<br>RMS40<br>LAS | 96.77±26.38<br>21.00±15.89<br>61.09±88.07 | 97.04±29.20<br>15.92±12.62<br>63.19±84.38 | 0.91<br>0.21<br>0.49 |
| | WCL<br>WMC<br>WSA<br>WRL | 156.86±34.08<br>246.00±75.24<br>4590.2±765.54<br>0.701±0.091 | 146.26±22.32<br>223.85±56.35<br>4405.7±605.6<br>0.729±0.084 | $4.80 \times 10^{-2}$<br>$4.80 \times 10^{-2}$<br>0.16<br>0.13 |

Fig. 56

ASSOCIATION OF POSITIVE SAECG FINDINGS WITH FOLLOW-UP EVENTS

| EVENT | CRITERION | | | | | | | | | | | | | | |
|---|---|---|---|---|---|---|---|---|---|---|---|---|---|---|---|
| | TD* | | | TD | | | $WA_{ALL}$ | | | $WA_{TRIPLET1}$ | | | $WA_{TRIPLET2}$ | | |
| | tp | tn | p** | tp | tn | p** | tp | tn | p** | tp | tn | p= | tp | tn | p** |
| CM | 18 | 222 | 1.00 | 17 | 321 | 0.10 | 10 | 412 | 0.18 | 14 | 387 | 0.04 | 11 | 402 | 0.13 |
| PAD | 11 | 226 | 0.66 | 10 | 325 | 0.50 | 7 | 420 | 0.18 | 9 | 393 | 0.13 | 7 | 409 | 0.29 |
| SCD | 10 | 227 | 0.81 | 8 | 325 | 0.81 | 6 | 421 | 0.26 | 8 | 394 | 0.12 | 6 | 410 | 0.41 |
| VT | 15 | 232 | 0.06 | 13 | 330 | 0.01 | 11 | 426 | $4.2 \times 10^{-4}$ | 11 | 397 | $3.2 \times 10^{-3}$ | 11 | 415 | $9.7 \times 10^{-4}$ |
| PAE | 13 | 225 | 0.83 | 11 | 323 | 0.52 | 8 | 418 | 0.20 | 10 | 391 | 0.10 | 8 | 407 | 0.22 |
| ARF | 12 | 226 | 0.83 | 9 | 323 | 0.83 | 7 | 419 | 0.28 | 9 | 392 | 0.14 | 7 | 408 | 0.31 |

Fig. 57

COMPARISON OF POSITIVE ACCURACY OF PREDICTING FOLLOW-UP EVENTS

| EVENT | SEN [%] | PPA [%] TD | PPA [%] WD | DISCORDANCE TD+ | DISCORDANCE WD+ | p = |
|---|---|---|---|---|---|---|
| CARDIAC MORTALITY | 25 | 10.53 | 25.00 | 15 | 89 | $2.55 \times 10^{-7}$ |
|  | 40 | 9.56 | 13.54 | 37 | 77 | $2.27 \times 10^{-4}$ |
|  | 50 | 8.37 | 11.69 | 61 | 112 | $1.30 \times 10^{-4}$ |
|  | 60 | 8.26 | 11.41 | 59 | 109 | $1.41 \times 10^{-4}$ |
|  | 75 | 7.12 | 10.91 | 38 | 155 | $5.74 \times 10^{-18}$ |
|  | 80 | 6.28 | 10.88 | 15 | 232 | $3.64 \times 10^{-51}$ |
| POTENTIALLY ARRHYTHMIC DEATH | 25 | 6.49 | 21.88 | 13 | 62 | $8.40 \times 10^{-9}$ |
|  | 40 | 6.30 | 14.29 | 18 | 89 | $1.78 \times 10^{-12}$ |
|  | 50 | 5.53 | 8.77 | 42 | 125 | $9.05 \times 10^{-11}$ |
|  | 60 | 5.06 | 7.65 | 56 | 132 | $2.95 \times 10^{8}$ |
|  | 75 | 4.15 | 6.87 | 29 | 182 | $2.75 \times 10^{-28}$ |
|  | 80 | 4.00 | 6.62 | 18 | 209 | $2.03 \times 10^{-42}$ |
| SUDDEN CARDIAC DEATH | 25 | 6.49 | 20.00 | 9 | 61 | $1.28 \times 10^{-10}$ |
|  | 40 | 4.71 | 8.51 | 34 | 129 | $3.15 \times 10^{-14}$ |
|  | 50 | 4.71 | 7.90 | 47 | 124 | $3.38 \times 10^{-9}$ |
|  | 60 | 4.40 | 7.38 | 53 | 154 | $1.29 \times 10^{-12}$ |
|  | 75 | 3.63 | 6.83 | 20 | 201 | $8.61 \times 10^{-39}$ |
|  | 80 | 3.57 | 5.84 | 8 | 276 | $6.30 \times 10^{-71}$ |
| VENTRICULAR TACHYCARDIA | 25 | 21.74 | 31.25 | 15 | 22 | 0.32 |
|  | 40 | 14.29 | 22.22 | 26 | 51 | $5.87 \times 10^{-3}$ |
|  | 50 | 12.82 | 16.67 | 41 | 59 | $8.86 \times 10^{-2}$ |
|  | 60 | 11.83 | 11.96 | 62 | 63 | 1.00 |
|  | 75 | 7.96 | 9.46 | 63 | 91 | $2.92 \times 10^{-2}$ |
|  | 80 | 6.52 | 8.67 | 60 | 117 | $2.20 \times 10^{-5}$ |
| ARRHYTHMIC EVENT | 25 | 6.43 | 21.88 | 7 | 111 | $3.38 \times 10^{-25}$ |
|  | 40 | 6.15 | 10.64 | 33 | 116 | $5.02 \times 10^{-12}$ |
|  | 50 | 6.03 | 9.40 | 61 | 115 | $5.71 \times 10^{-5}$ |
|  | 60 | 5.51 | 9.40 | 48 | 153 | $5.72 \times 10^{-14}$ |
|  | 75 | 4.66 | 7.66 | 29 | 180 | $8.20 \times 10^{-28}$ |
|  | 80 | 4.55 | 7.20 | 18 | 212 | $3.24 \times 10^{-43}$ |
| ARRHYTHMIC FATALITIES | 25 | 6.12 | 18.75 | 11 | 77 | $2.40 \times 10^{-13}$ |
|  | 40 | 5.24 | 9.57 | 34 | 129 | $3.15 \times 10^{-14}$ |
|  | 50 | 4.96 | 8.73 | 52 | 129 | $9.75 \times 10^{-9}$ |
|  | 60 | 4.73 | 8.73 | 23 | 187 | $3.95 \times 10^{-33}$ |
|  | 75 | 4.15 | 6.81 | 29 | 180 | $8.20 \times 10^{-24}$ |
|  | 80 | 4.14 | 6.36 | 12 | 230 | $1.91 \times 10^{-53}$ |

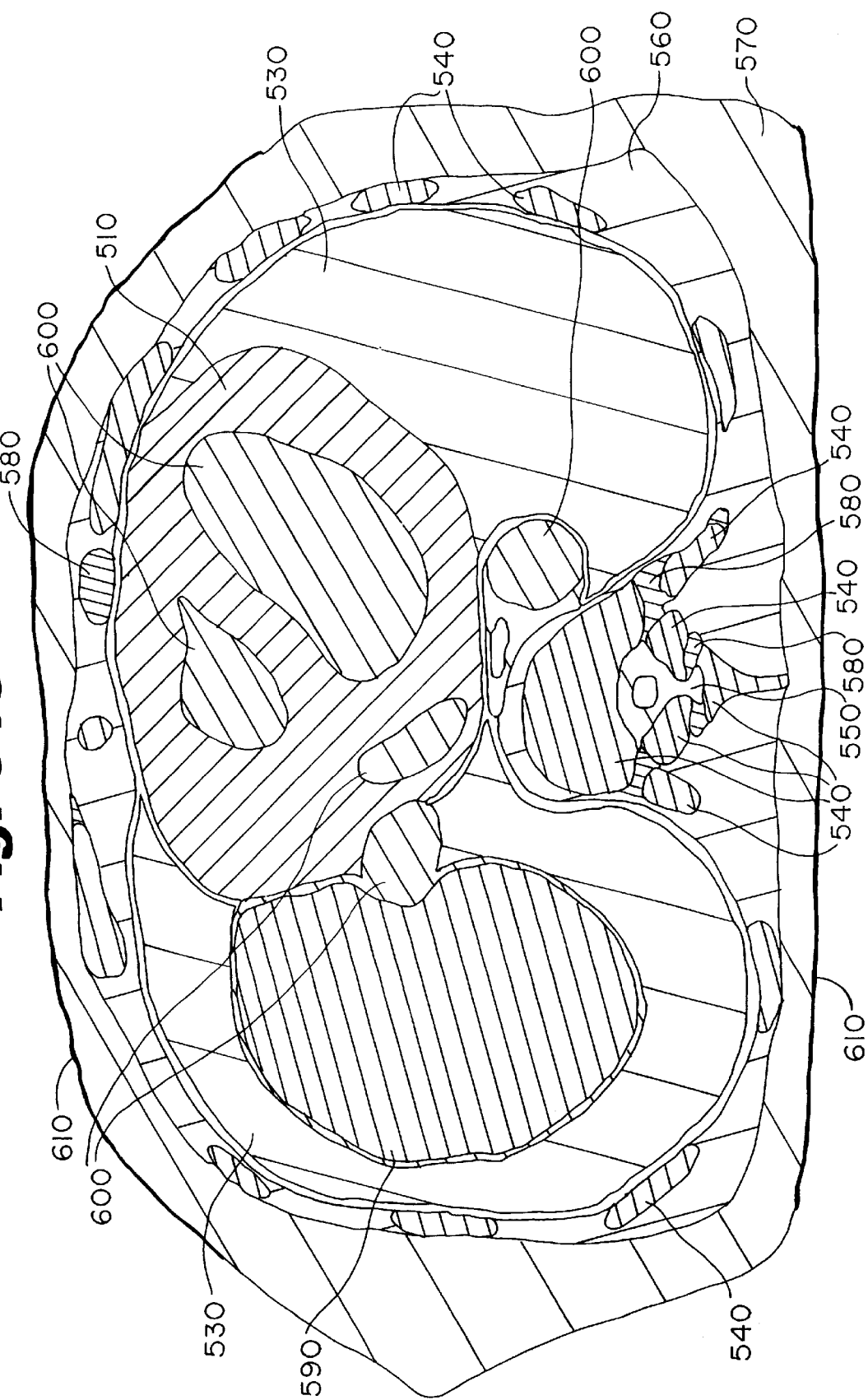

Fig. 65

| TISSUE | RESISTIVITY ($\Omega$ CM) |
|---|---|
| MYOCARDIUM | 400 |
| BLOOD | 150 |
| BONE | 15000 |
| CARTILAGE | 7000 |
| FAT | 2000 |
| LIVER | 450 |
| LUNGS | 1200 |
| SKELETON MUSCLE | 700 |
| OESOPHAGUS | 600 |
| PLEURA | 200 |
| SPINAL CHORD | 300 |

Fig. 66

| ELECTRODE | SEGMENT 1 | SEGMENT 2 | SEGMENT 3 | SEGMENT 4 | SEGMENT 5 |
|---|---|---|---|---|---|
| 1 | 000 - 059 | | | | |
| 2 | 000 - 089 | | | | |
| 3 | 000 - 119 | | | | |
| 4 | 000 - 149 | | | | |
| 5 | 000 - 179 | | | | |
| 6 | 000 - 209 | | | | |
| 7 | 000 - 239 | | | | |
| 8 | 000 - 039 | 060 - 099 | | | |
| 9 | 000 - 039 | 080 - 119 | | | |
| 10 | 000 - 039 | 100 - 139 | | | |
| 11 | 000 - 039 | 120 - 159 | | | |
| 12 | 000 - 059 | 080 - 119 | | | |
| 13 | 000 - 059 | 100 - 159 | | | |
| 14 | 000 - 059 | 120 - 189 | | | |
| 15 | 000 - 059 | 140 - 199 | | | |
| 16 | 000 - 079 | 100 - 179 | | | |
| 17 | 000 - 079 | 120 - 199 | | | |
| 18 | 000 - 079 | 140 - 219 | | | |
| 19 | 000 - 079 | 160 - 239 | | | |
| 20 | 000 - 099 | 120 - 219 | | | |
| 21 | 000 - 099 | 140 - 239 | | | |
| 22 | 000 - 039 | 060 - 099 | 120 - 159 | | |
| 23 | 000 - 039 | 080 - 119 | 160 - 199 | | |
| 24 | 000 - 039 | 100 - 139 | 200 - 239 | | |
| 25 | 000 - 059 | 080 - 119 | 140 - 209 | | |
| 26 | 000 - 069 | 090 - 159 | 180 - 239 | | |
| 27 | 000 - 029 | 060 - 089 | 120 - 149 | 180 - 209 | |
| 28 | 000 - 029 | 070 - 099 | 140 - 169 | 210 - 239 | |
| 29 | 000 - 039 | 060 - 099 | 120 - 159 | 180 - 219 | |
| 30 | 000 - 029 | 050 - 079 | 100 - 129 | 150 - 179 | 200 - 229 |

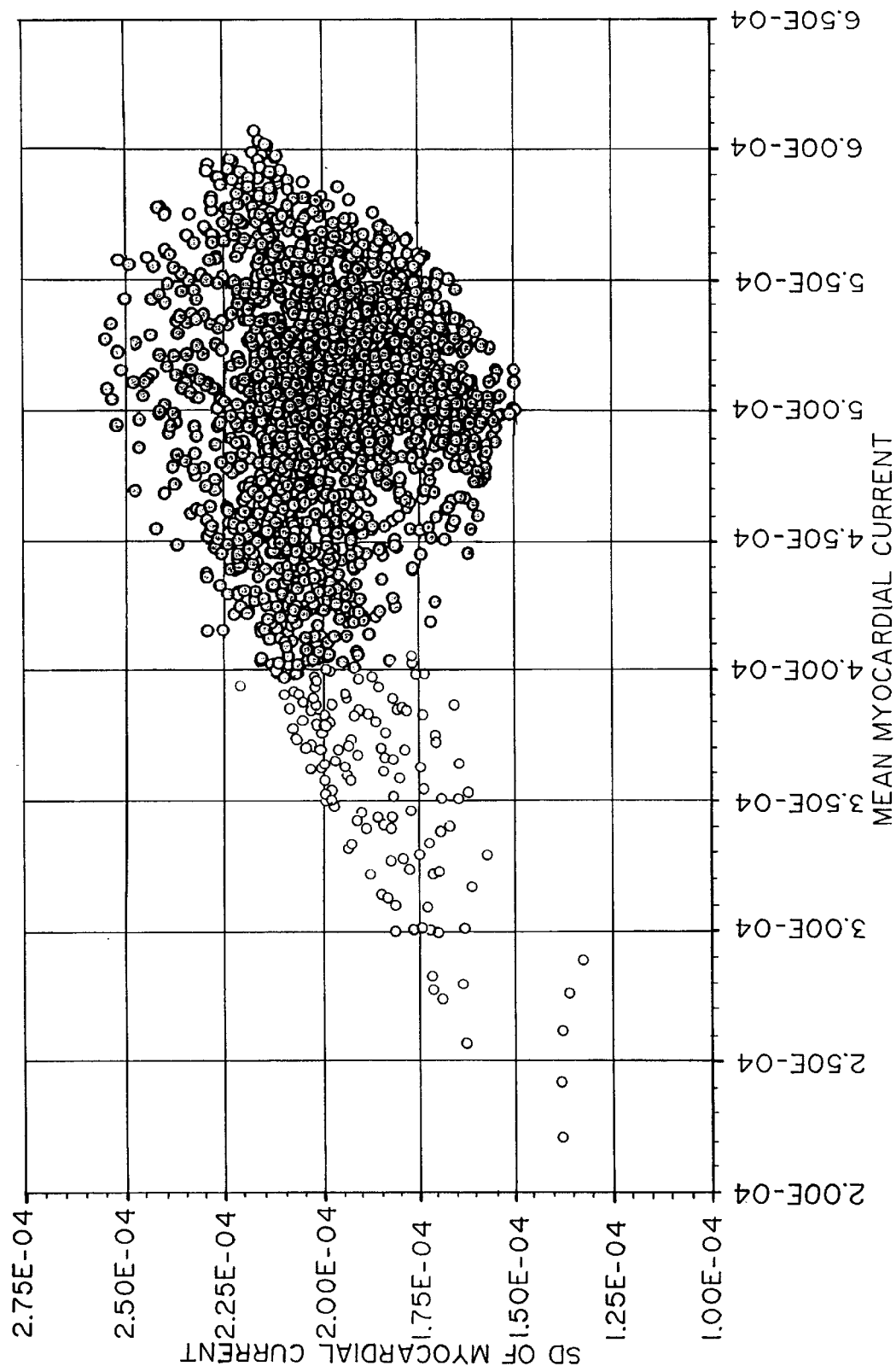

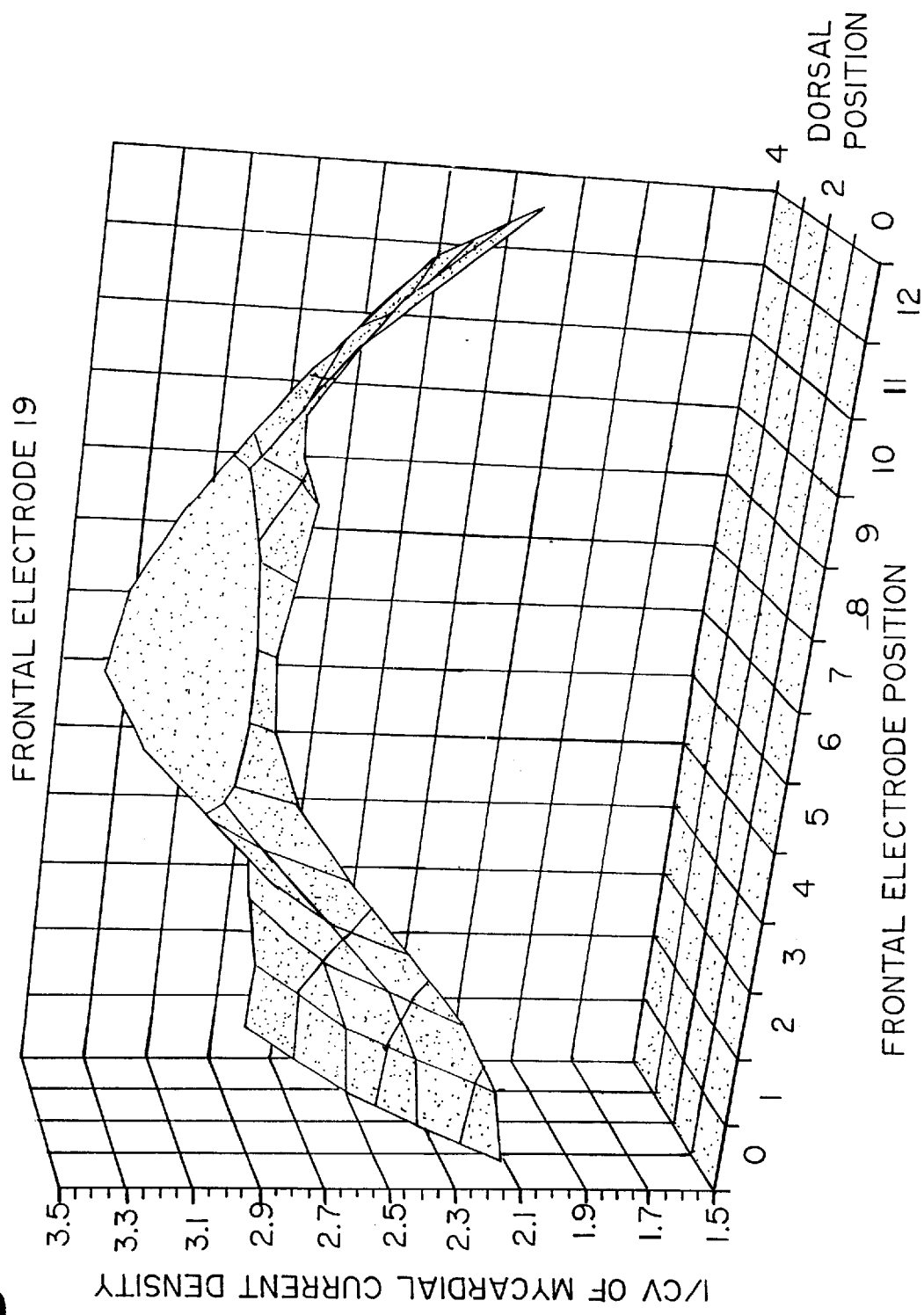

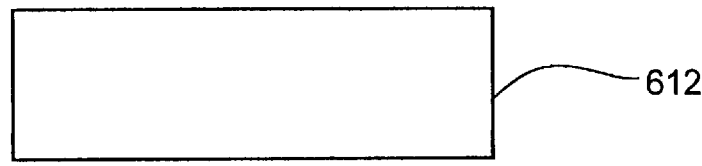
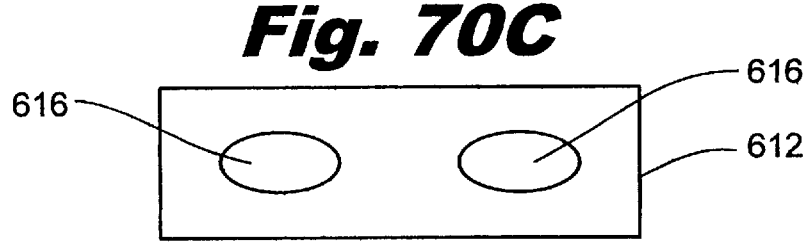
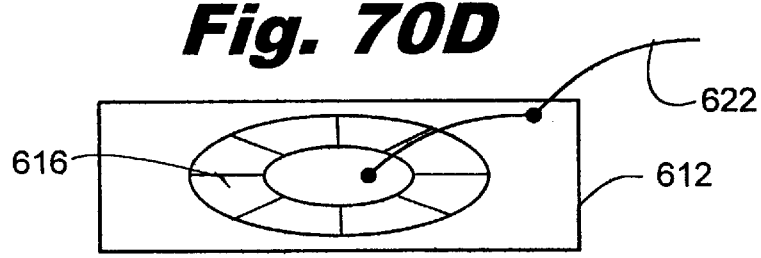
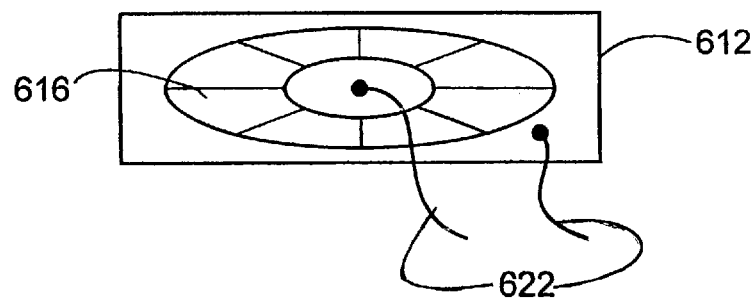

METHOD OF NONINVASIVELY DETERMINING A PATIENT'S SUSCEPTIBILITY TO ARRHYTHMIA

Provisional Applications No. 60/191,029 filed Mar. 21, 2000 which is a provisional Application No. 60/138,497, filed Jun. 10, 1999 also No. 60/138,439.

FIELD OF THE INVENTION

The invention relates to the detection of patients' susceptibility to arrhythmias and, more particularly, to various techniques for improving the detection of signals to achieve this goal.

BACKGROUND OF THE INVENTION

There are various devices known in the art for monitoring heart function. Many of these devices typically function by analyzing signals such as an electrocardiogram signal, which can be representative of heart function.

There is a need to identify patients at high risk for life-threatening arrhythmias.

Various means have been proposed for detecting patient susceptibility to arrhythmias. U.S. Pat. No. 5,117,834 discloses one method by which pulses of electromagnetic energy are injected into a patient and the changes; in the patient's electrocardiographic signals caused by the injection are recorded. U.S. Pat. No. 5,351,687 is similar in concept to U.S. Pat. No. 5,117,834, but it describes use of a magnetic sensor for use in detecting the cardiographic signals. U.S. Pat. No. 5,555,888 discloses various means for adapting and automatically facilitating the assessment techniques and means similar to that shown in the above patents for determining patient susceptibility to arrhythmias.

Other techniques which are used to analyze cardiac signals for somewhat similar purposes include those known as t-wave alternans and signal-averaged electrocardiograms. Each of these techniques is limited in its application and utility by various factors which are overcome through use of the below described inventions.

SUMMARY OF THE INVENTION

The present invention provides a system and method of determining, through noninvasive means, a patient's susceptibility to arrhythmia. More specifically, this invention comprises various improvements to known innovations for optimizing detection of a patient's susceptibility to arrhythmias. This invention embodies numerous software and sequence improvements for applying this basic technology.

Another purpose of this invention is to provide hardware and software analysis means for detecting and amplifying relevant signals.

Another purpose of this invention is to provide for improved performance lead sets and the software to promote ease of attachment and removal from the patient and ease of connection of the lead system to the hardware.

A further object of this invention is to provide new combinations of electrode placement and use to promote better arrhythmia susceptibility diagnosis.

A further object of this invention is to provide a reduction in the size of necessary components to allow for hand-held system dimensions.

A further object of this invention is to provide a means for distinguishing between the signals from the X, Y, and Z directions as well as previously unused directional components of very low-level signal data.

Another object of this invention is to supply means for displaying of patient's waveforms and other data derived from the detected signals, as well as to provide various interfaces to communicate the data between the patient and physician or health care professional.

It is a further object of this invention to provide signal artifact reduction, and to provide a single point connector for the set of leads.

Another object of this invention is to provide improved lead materials for improved performance, as well as an improved lead effect modeling (LEM).

It is yet another object of this invention to provide amplifier circuitry that minimizes amplifier saturation and optimizes fast recovery.

BRIEF DESCRIPTION OF THE DRAWINGS

FIG. 44 is a lower-level flow chart of the test control and acquisition portion of the software.

FIGS. 45 and 45a–b is a lower-level flow chart of the post-processing software operation.

FIG. 54 is a table of interdependence of time-domain and wavelet decomposition indices.

FIG. 55 is a table that depicts a comparison of signal-averaged ECG indices in patients with and without follow-up events.

FIG. 56 is a table that depicts an association of positive SAECG findings with follow-up events.

FIG. 57 is a table that depicts a comparison of positive accuracy of predicting follow-up events.

FIGS. 64A–C depict bit maps of three representative cross-sections of the human thorax within the lower mediastinum.

FIG. 65 depicts a table of individual tissue types and the assigned electrical resistances.

FIG. 66 depicts electrode segment data and electrode configuration.

FIGS. 67A–H depict graphical summaries of individual results obtained in an entire set of 1,950 experiments.

FIGS. 68A–G depict individual values of the coefficient of variance of myocardial current density obtained for individual electrode configuration and positioning.

FIGS. 70A–E depict various embodiments of the present invention comprising stimulation leads or electrodes.

DETAILED DESCRIPTION OF THE INVENTION

Figure 1:
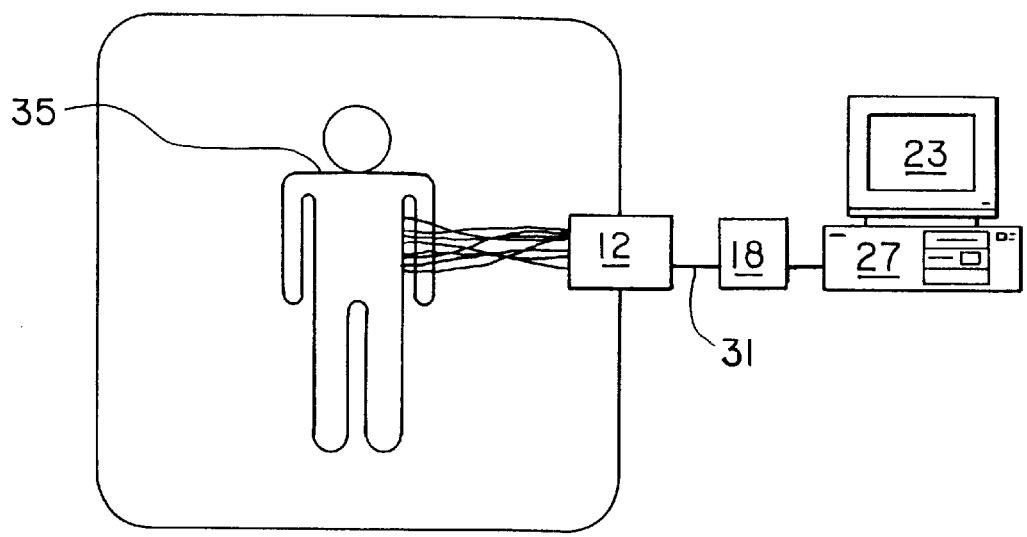
FIG. 1 depicts the broad overview of the invention, showing the patient electronic interface computer.

The invention provided is an improved; method and system for detecting patients' susceptibility to arrhythmia and cardiac tissue abnormality in a noninvasive fashion. In FIG. 1, computer 27 is operably coupled to monitor 23, which is further closely coupled with electronic interface 18 via wire 31. Lead system 12 is connected between patient 35 and electronic interface 18.

Figure 2:
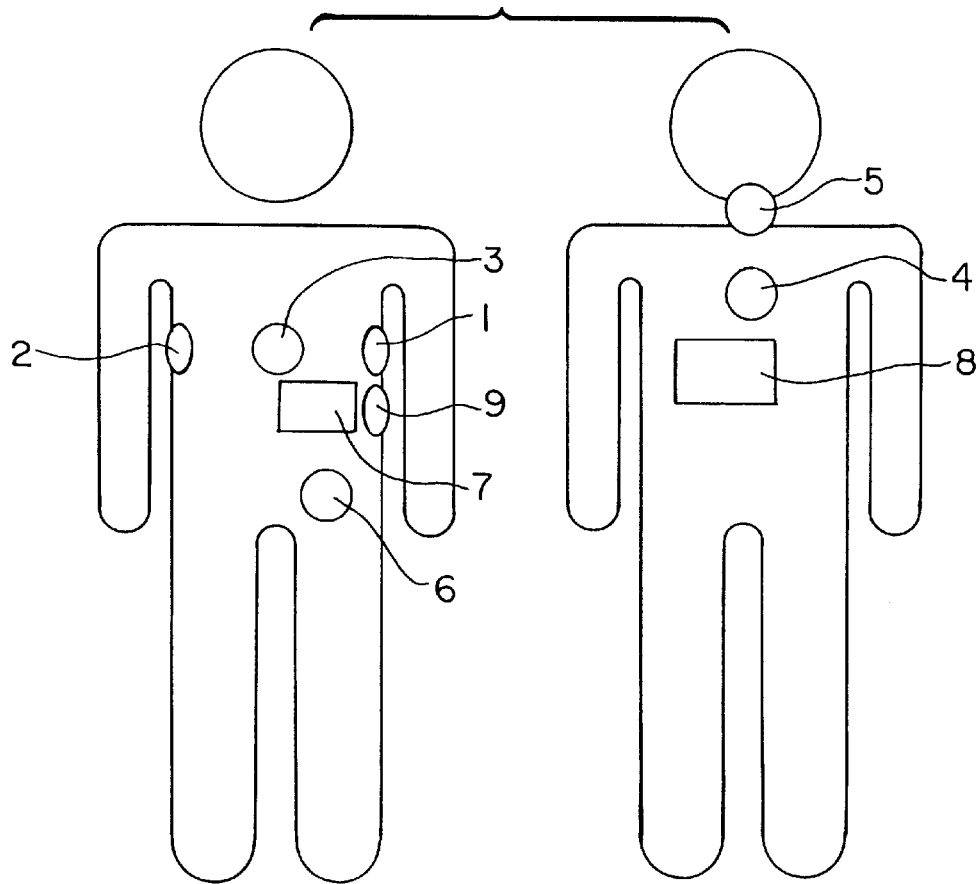
FIG. 2 is an exemplary depiction of a patient showing possible electrode patient locations.

FIG. 2 is a front and rear view of patient 35. In one preferred embodiment, lead system 12 consists of 9 lead wires. Advantageously, the lead system can be connected as shown in FIG. 2 for efficient and consistent setup of the invention. Typically, the lead system is preassembled with a predetermined number of leads having predetermined lengths. Although it is contemplated by this invention that the lead system can be preassembled with leads of different lengths to accommodate different room sizes and patent locations, among other factors, a general consideration is that the sensing leads and energy delivery leads are less than 9 feet in length to reduce possible induced noise. Further, the leads in lead system 12 are constructed from a low-impedance material, such as tin, sodium, silver, silver chloride, or other low-impedance material recognized as such by those skilled in the art. This construction assists in efficient delivery of subpacing energy for stimulation leads and increased sensitivity for sensing leads. The electrodes involved with energy delivery are advantageously shaped and sized for placement on the patient's body habitus to minimize signal quality reduction by avoiding muscle tissue.

Figure 3:
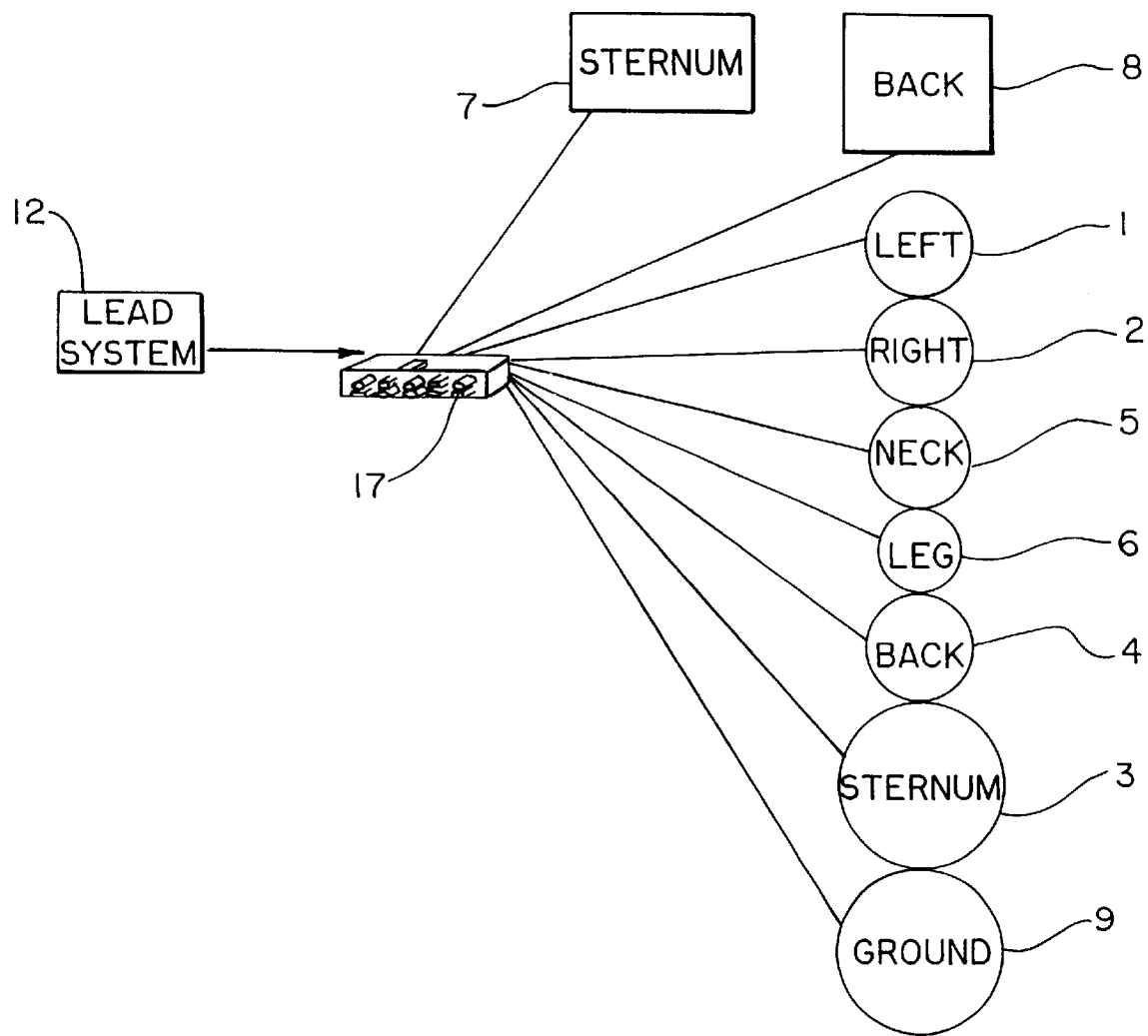
FIG. 3 is a more close-up view of the lead system, showing the connector and attached electrodes.

FIG. 3 shows a more detailed view of one preferred embodiment of single-point connector 15 with 9 lead wires electronically coupled thereto. In this embodiment, each of the 9 lead wires is connected to one of 9 self-adhesive electrodes. The adhesive used on any specific electrode can differ depending on various factors, including where on patient 35 the electrode or patch is to be affixed and whether the electrode is reusable or disposable. In one preferred embodiment, electrode 1 is to be connected in the correspondingly-numbered position indicated in FIG. 2. Thus, for example, electrodes 1 and 2 are connected on patient 35 at the corresponding left and right mid-axillary lines, on a horizontal plane, at the level where the fifth intercostal space intersects the sternum. Electrode 3 is placed on the sternum. intercostal space intersects the sternum. Electrode 3 is placed on the sternum. In this embodiment of the invention, electrode 4 is placed on patient 35 at the fifth intercostal space. Electrode 5 is a neck electrode and is attached generally at the back of the neck, as indicated on the back view [2.2] of FIG. 2. Lead 6 is a left leg lead that will attach generally in the location on patient 35, as shown on the front view [2.1] of FIG. 2. The larger, rectangular electrodes, electrodes 7 and 8, are attached in the pectoral area and back, respectively, as shown in FIG. 2. In one preferred embodiment, the generally pectorally-placed electrode 7 or patch has a skin contact surface area of at least 20 $cm^2$, and typically less than about 70 $cm^2$. The patches of lead system 12 can be constructed with different electrical characteristics to facilitate energy transfer and sensing. In this embodiment of the invention, electrode 4 is placed on patient 35 at the fifth intercostal space. Electrode 5 is a neck electrode and is attached generally at the back of the neck, as indicated on back view 2.2 of FIG. 2. Lead 6 is a left leg lead that will attach generally in the location on patient 35, as shown on front view 2.1 of FIG. 2. The larger, rectangular electrodes, electrodes 7 and 8, are attached in the pectoral area and back, respectively, as shown in FIG. 2. In one preferred embodiment, the generally pectorally-placed electrode 7 or patch has a skin contact surface area of at least 20 $cm^2$, and typically less than about 70 $cm^2$. The patches of lead system 12 can be constructed with different electrical characteristics to facilitate energy transfer and sensing.

Figure 37:
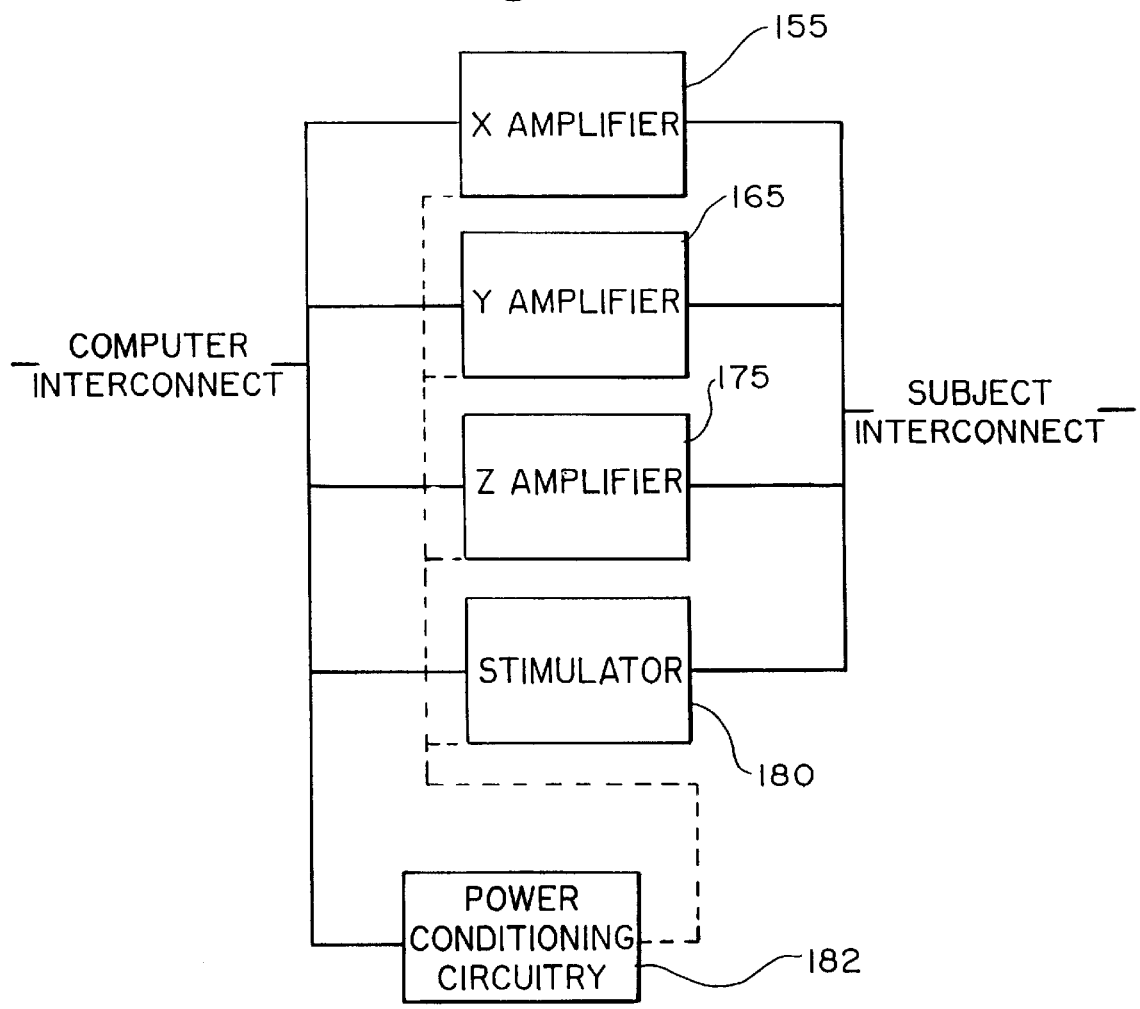
FIG. 37 is a high-level block diagram of the electronics interface.

Single-point connector 17 is configured to electronically mate with electronic interface 18. A top-level block diagram of electronic interface 18 is shown in FIG. 37. In one embodiment, single-point connector 17 advantageously couples 9 electroleads into one plug assembly. As can be seen in FIG. 3, one preferred embodiment is a stacked lead receptacle having at least two rows of lead connections that are identified with respect to each lead (also see FIGS. 42 a–b). This advantageously provides for a more compact connector, and provides for rapid and efficient coupling and decoupling to electronics interface 18. In one preferred embodiment, the connector 17 is designed to be easily and rapidly coupled and decoupled with the electronics interface 18 by the use of only one hand. Advantageously, this allows for efficient setup and takedown of the invention. Patches 1 through 9 are premarked, as indicated on FIG. 3, to provide for simpler and more convenient placement on patient 35. Further, the lead system 12 comprises a reference lead 9. It is anticipated that the lead system 12 can be a single-use system or a disposable system to provide for a safe and sterile means by which to perform the tests provided by this invention. Further, reusing the lead system may create a higher impedance in the system, which may make the lead system 12 more susceptible to noise. In one preferred embodiment of the invention, a means is provided for determining whether the lead system has been previously used. This can be done by using a single-use-type adhesive. Another means for detecting previous use is creating a deformable tab on connector 17 that deforms on its first mating with electronic interface 18, and thereafter is not usable. Creating fusible links or breakable tabs to indicate the lead system has been previously used are an additional means, among others.

The electronics interface 18, by coupling with computer 27, allows for the injection of low-level electromagnetic energy into patient 35 to alter at least one cardiac signal. The energy is delivered at a subpacing threshold and is typically introduced externally, through patient 35's chest and into cardiac tissue. The subpacing energy is delivered just before a QRS complex event, as determined by the data gathered by the hardware and electronic interface 18, and as analyzed by the software. Electronic interface 18 and attached computer 27 function to process received signals, among other functions. The energy delivery leads are typically leads 7 and 8; however, it is anticipated that circumstances may arise where more or the more-or-less flat signal, or absence of signal, subsequent to recovery of the S 121 portion of QRS complex 130, prior to commencement: of t-wave 146. The QT interval is typically defined as the portion of the signals commencing at the beginning of QRS complex 130 and ending after t-wave 146. J Joint 137 is typically defined as the end of the QRS complex and the beginning of the ST segment 133. The T-P interval (not indicated) is the time period from the end of the T-wave to the beginning of the next P-Wave. The entire cardiac cycle is P-Q-R-S-T.

The slight transcutaneous biosync or subpacing current is typically introduced by the invention at odd numbers of QRS complex normal sinus beats. Resulting QRS complexes are then compared to the even-numbered unbiased beats. By computer-implemented software, the distinguishable signal differences can then be calculated and displayed. Generally, differences are found between the biased and unbiased QRS complexes in patients with ventricular tachycardia and other indices of arrhythmia or cardiac tissue abnormality. It is anticipated that these input potentials would be extremely small, for example, less than 100 uV, and typically of a duration of less than about 100 mS. Such a current might involve visualization of a possible analog of late potentials throughout the QRS complex. In similar fashion it is within the scope of this invention to apply the biased and unbiased signal analysis to various other types of test methods and signals. The application of external subthreshold stimulation delivered through the ski n surface affects the ECG signals which may be evaluated in a myriad of ways, including Heart Rate Variability (HRV), ST segment elevation, QRST Timing Changes, and T-wave alternans. These methods are currently in use today but have never been used in combination with the novel features of this invention. The combination of external sub-threshold stimulation delivered through the skin surface to change or modulate these measurements is further described herein.

Heart Rate Variability is commonly measured by taking a sampling of R-wave to R-wave intervals from a subject and computing the standard deviation of these intervals. Other methods include the evaluation of modes of distribution of these intervals. For the purposes of this description, HRV shall generally be defined as the evaluation of the intervals between re-occurring activity in the heart. When external sub-threshold stimulation is delivered through the skin surface, these intervals can change. The changes vary from individual to individual. These changes (or lack thereof): can be used to identify an individual's cardiovascular and autonomic condition.

QRST Timing Changes are commonly measured by assessing the variability in spacing between the Q-wave and T-wave of the heart. Other methods include the evaluation of variability between Q-R, Q-S and R-S waves. For the purposes of these claims, QRST Timing Changes may be generally defined as any evaluation of variability in relative timing of any combination of Q-wave, R-wave, S-wave, or T-wave. When external sub-threshold stimulation is delivered through the skin surface, these timings can change. The changes vary from individual to individual. These changes (or lack thereof) can be used to identify an individual's cardiovascular and autonomic condition.

ST Segment Elevation is commonly measured by assessing the amplitude of the heart beat between the S-wave and the T-wave. Other methods include the evaluation of frequency content, amplitude variability and frequency variability. For the purposes of this description, ST Segment Elevation may be generally defined as any evaluation of signals occurring between the S-wave and T-wave. When external sub-threshold stimulation is delivered through the skin surface, these signals can change. She changes vary from individual to individual. These changes (or lack thereof can be used to identify an individual's cardiovascular and autonomic condition.

T-Wave Changes are currently measured by evaluating sequential T-wave amplitudes for alternans behavior. Other methods include the evaluation of frequency content, and frequency variability. For the purposes of these claims, T-Wave Changes may be generally defined as any variation of signals occurring between the S-wave and the subsequent heart beat. When external sub-threshold stimulation is delivered through the skin surface, these signals can change. The changes vary from individual to individual. These changes (or lack thereof) can be used to identify an individual's cardiovascular and autonomic condition. Use of these techniques include, in one or more combinations:

a. The use of HRV changes induced by sub-threshold (Oma-pacing threshold) stimulation delivered through the skin surface as an indicator of cardiovascular and autonomic condition;

b. The use of QRST timing changes induced by sub-threshold (Oma-pacing threshold) stimulation delivered through the skin surface as an indicator of cardiovascular and autonomic condition;:

c. The use of ST segment changes induced by sub-threshold (Oma-pacing threshold) stimulation delivered through the skin surface as an indicator of cardiovascular and autonomic condition; and d. The use of T-wave changes induced by sub-threshold (Oma-pacing threshold) stimulation delivered through the skin surface as an indicator of cardiovascular and autonomic condition.

In summary, it is possible to use any of the above cardiac evaluation techniques with the induced signals of the invention to measure variability of the resulting signals. This variability can be compared to the variability of signals or intervals without stimulation. The relationships and mechanisms for the changes are discernible in these combinations, and provide considerable diagnostic value for the patient and the investigating caregiver.

Figure 4:
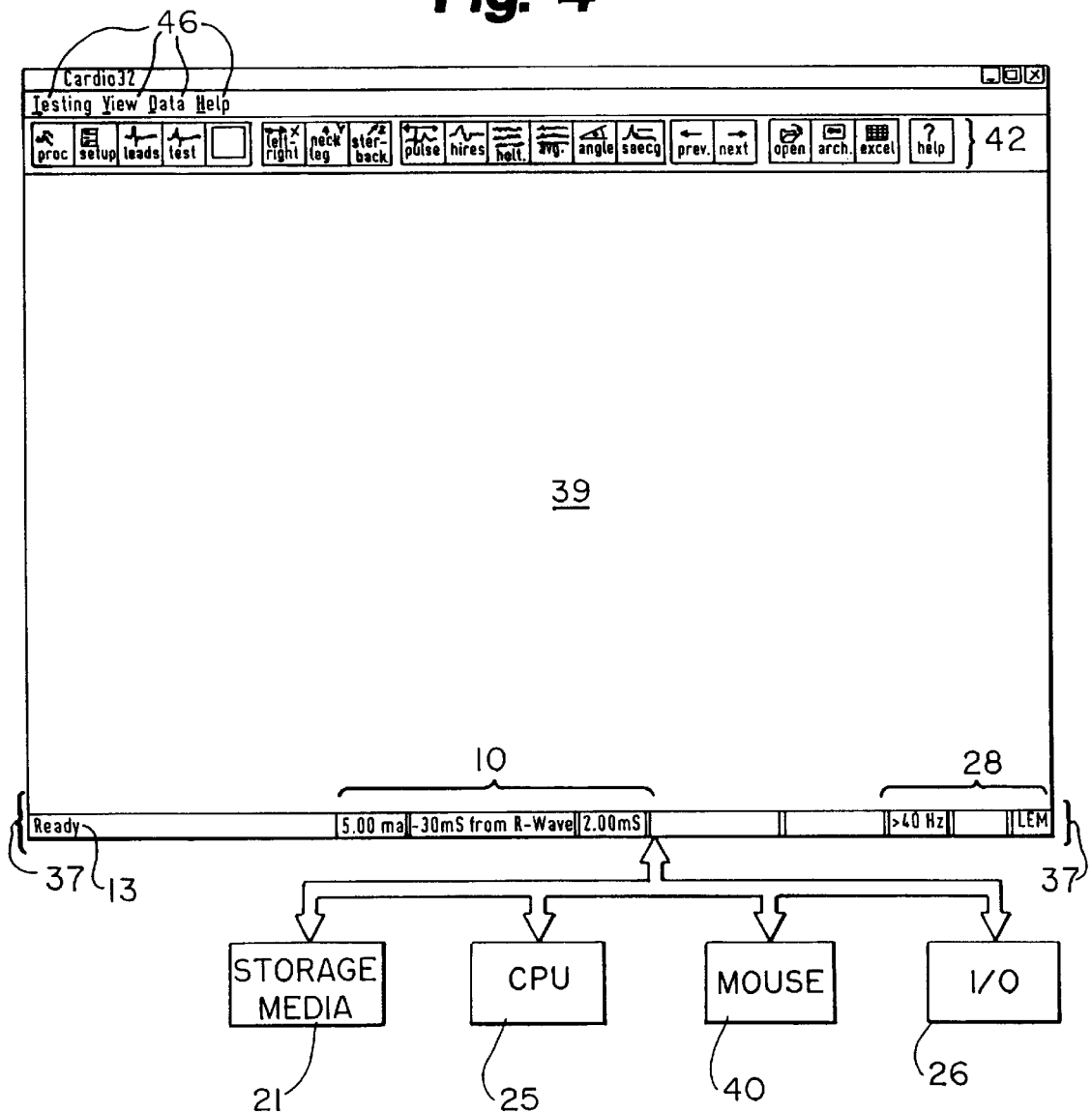
FIG. 4 depicts the principal graphical user interface (GUI) generated by the computer and the software portion of the invention.

Computer 27 operates a graphical user interface (GUI) based software, which generally includes a tool bar, a status bar, a display area, and various drop-down menus. The principal GUI is depicted in FIG. 4. The GUI consists of display area 39, status bar 37, tool bar 42, and drop-down menus 46. Tool bar 42 contains button icons that represent shortcuts to many of the functions described below in association with drop-down means 46. Status bar 37 depicts the general status 13 of the software on the left-hand side, technical data 10 regarding the lead sensors and input current in the middle section, and frequency and protocol information 28 generally on the right-hand side. FIG. 4 illustrates a GUI in Microsoft Corporation's Windows 95™ operating system format. The GUI is generated by computer 27, which typically consists of mouse 40, CPU 25, display 23, a keyboard (not shown) operably attached to computer 27, and peripheral input/output devices 26, as well as storage media 21.

Figure 5:
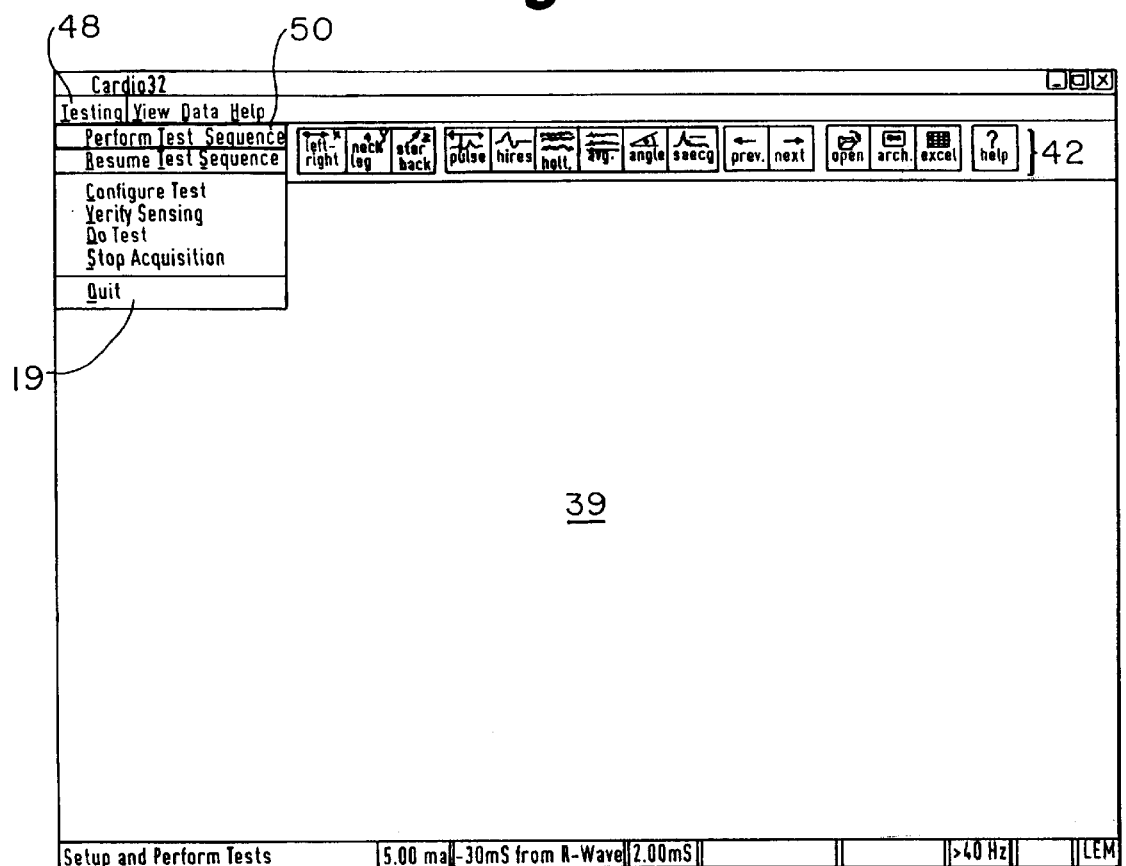
FIG. 5 is the principal GUI generated by the computer and software portion of the invention, with the testing menu engaged.
Figure 6:
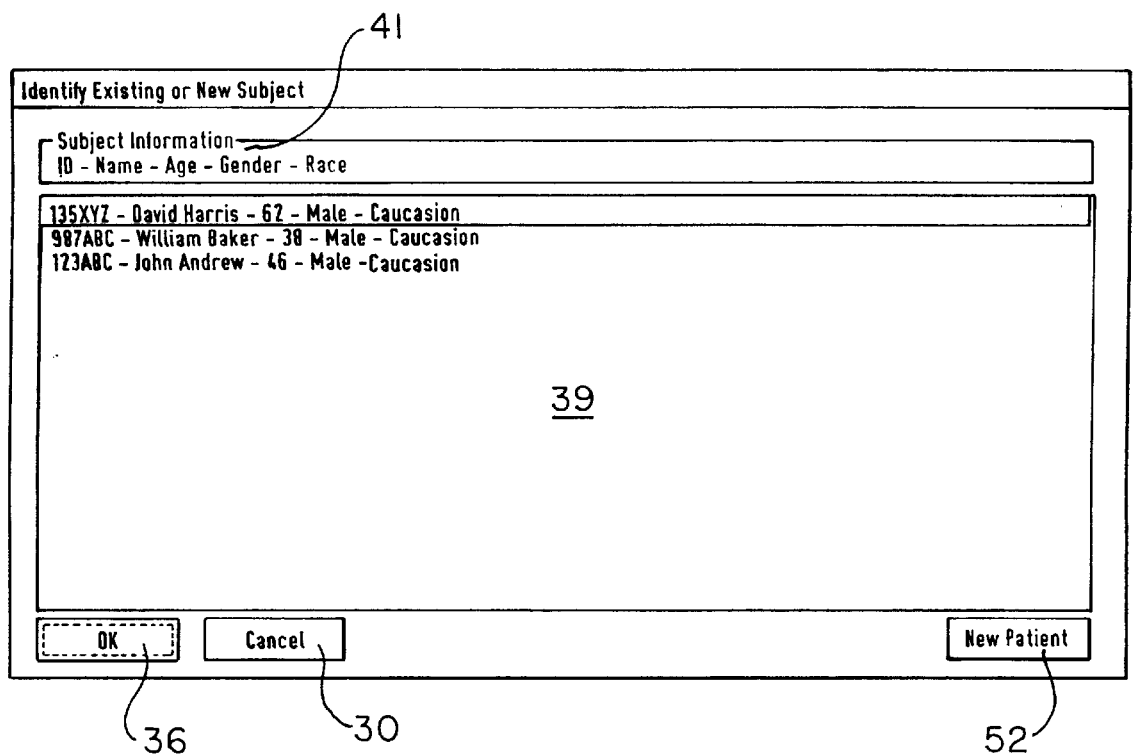
FIG. 6 is the "New Subject" GUI.

FIG. 5 depicts "Testing" drop-down menu 48 engaged. As revealed in FIG. 5, "Testing" drop-down menu 48 provides a series of options to perform testing provided for by this invention. If the "Performed Test Sequence" 50 is selected, the GUI of FIG. 6 is generated on display 23. Using mouse 40 or keyboard input, a preexisting patient may be selected from display area 39 of this GCI, or "New Patient" button 52 may be selected. Mouse 40 or keyboard input may be used to select all operable functions of the GUIs involved in this invention. If "OK" 36 is selected from the GUI of FIG. 6, subject information 41 is retrieved for the highlighted subject. "Cancel" 30 returns the operator to the view of the GUI of FIG. 4.

Figure 7:
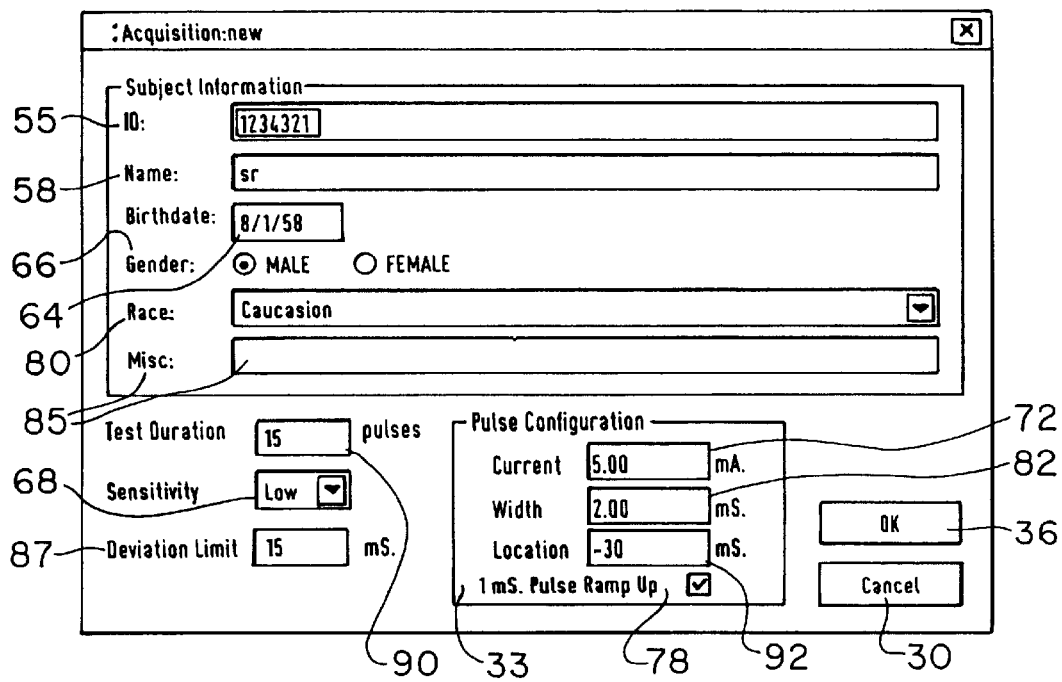
FIG. 7 is the "Acquisition" GUI.

FIG. 7 depicts the informational GUI that appears if "New Patient" button 52 is selected. In the upper portion of the GUI represented in FIG. 7, subject information may be entered in box 44 which includes identification number (ID) 55 to associate with the patient, patient's Name 58, patient's Birthdate 64, Gender 66 of the patient, Race 80 of the patient, and any miscellaneous notes 85 that might be helpful during or after the patient's diagnostic sessions.

The lower portion of the GUI depicted in FIG. 7 includes six boxes where testing parameters are entered. The test duration box 90 is configured by the medical professional to indicate how many QRS complex signals will comprise the test. The options under the sensitivity input box 68 are low, medium, and high. This advantageously allows the sensitivity to be adjusted to correct over- or under-sensing caused by subject-to-subject variation in QRS amplitude and morphology. The next variable parameter is the deviation limit 87, which is entered in milliseconds in the correspondingly marked box. Deviation limit 87 allows the operator to eliminate inaccurately-positioned stimulations from post-processing. This can happen due to the predictive nature of pre-R-wave stimulation and the normal R-R interval variation (see FIG. 36). The operator identifies the allowable tolerance. Any pulses that are greater than: this tolerance are eliminated from further processing. Also in FIG. 7 is pulse configuration box 33. In pulse configuration box 33, the low-current pulse can be configured to account for the different circumstances of the patient to be tested. The parameters or variables are current strength 72, width of the pulse 82 (in milliseconds), and temporal location 92 of the pulse with respect to the QRS complex. A one-millisecond Pulse Ramp Up 78 option is also available by checking the corresponding box on the GUI.

Figure 8:
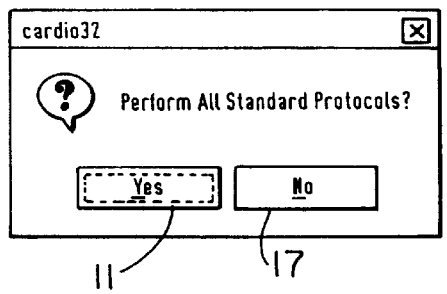
FIG. 8 is the "Perform All Standard Protocols" GUI.

FIG. 8 depicts a GUI option screen where a simplified selection can be made for all available testing standard protocols. There, selection of "Yes" 11 invokes all currently defined standard protocols. These protocols are set up initially and invoke from this screen. This option advantageously allows testing without requiring the operator to set the specific parameters for each subject being tested. "No" 17 returns the user to the previously displayed GUI.

Figure 9:
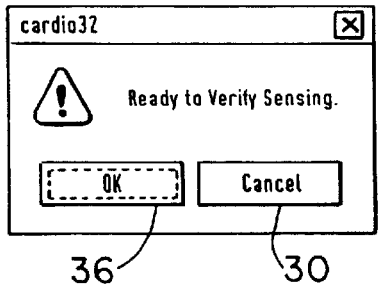
FIG. 9 is the "Ready to Verify Sensing"GUI.

FIG. 9 is a GUI that appears on screen 23 to determine whether the professional is ready to verify the sensing of the electrodes attached to patient 35. "Yes" 36 will commence the sensor verification. "Cancel" 30 will return the operator to the previous screen. If default protocols are to be used on the patient, then the operator need not define the test parameters. The system will get these standard parameters from the internal disk (not shown) of computer 27.

If "Cancel" 30 is selected on the GUI of FIG. 7, any changes will be discarded and the performed test function will cease. If "OK" 36 is selected on the GUI of FIG. 7, the GUI of FIG. 8 will appear. The medical professional will select "Yes" 11 if the system is to use the standard protocol stored internally.

Figure 10:
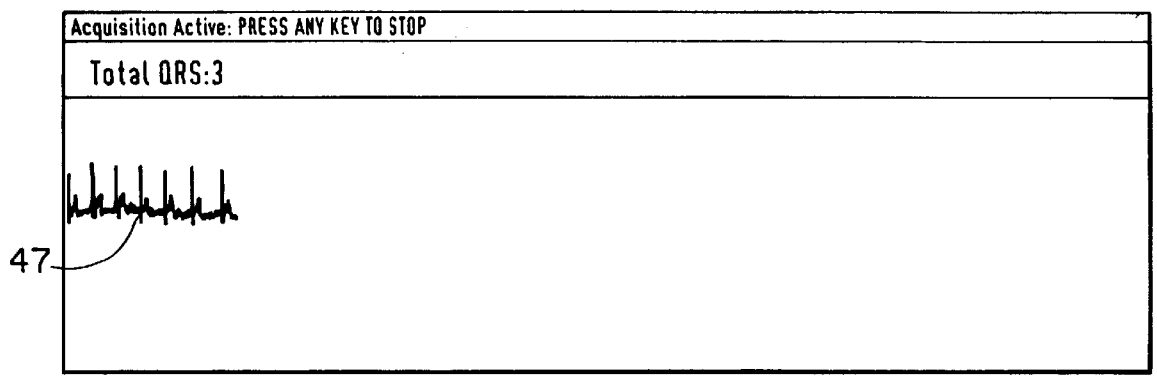
FIG. 10 is the "Acquisition Active" GUI generated by the computer and software portion of the invention.
Figure 11:
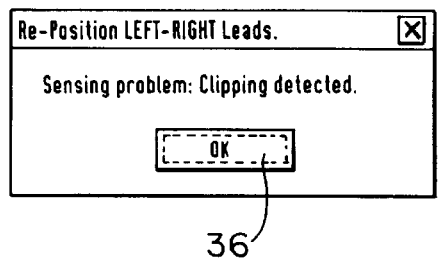
FIG. 11 is the "Sensing Problem" GUI generated by the computer and software portion of the invention.
Figure 12:
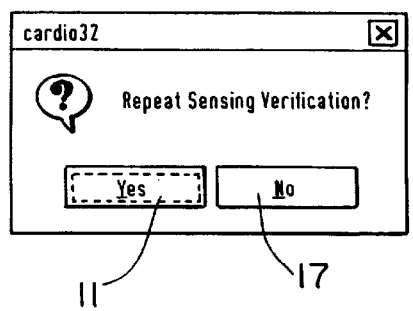
FIG. 12 is the "Repeat Sensing Verification" GUI generated by the computer and software portion of the invention.
Figure 31:
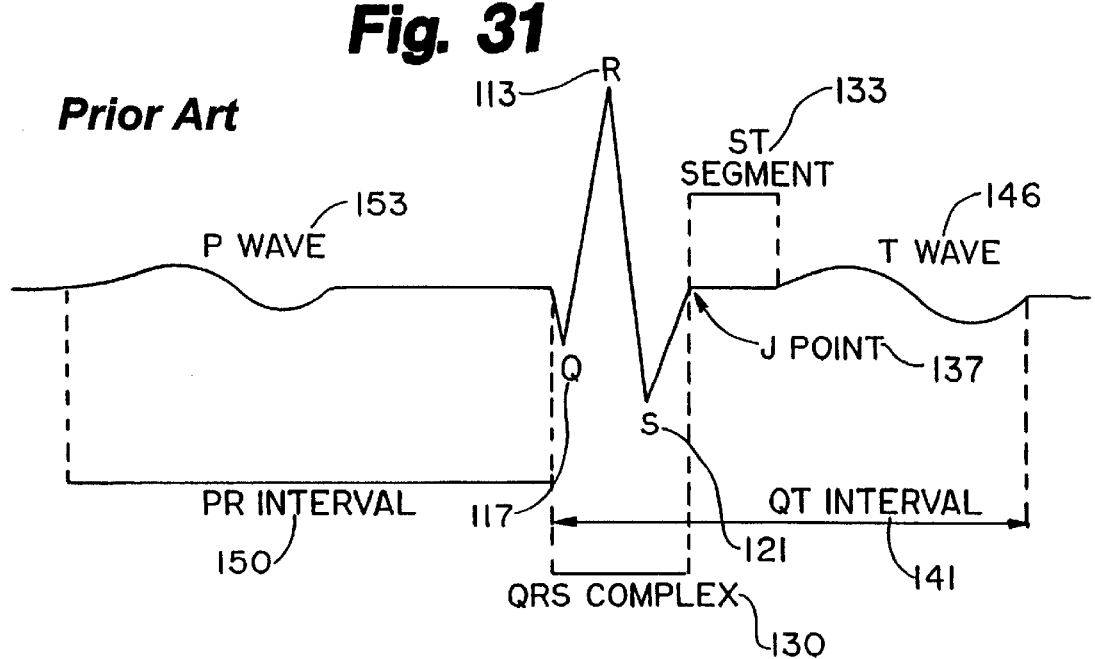
FIG. 31 is an exemplary EKG signal.

In a particular embodiment of the subject invention, prior to acquiring test data for a particular test, the computer-implemented software will acquire data for a 10-second interval, displaying and indicating detected R-waves or QRS complexes (see FIG. 31). This process allows the operator to confine the placement of lead system 12, and the sensitivity settings that appear in the GUI of figure 7. If the test data is not completely satisfactory to the operator, the steps represented in FIGS. 7, 8, 9, and 10 may be iterated to allow the medical professional to reposition the leads, if necessary, to provide for optimal sensing and signal amplitude. During data acquisition, a window depicting the data being acquired appears. An exemplary display of this graphical depiction of acquired signal 47 appears in FIG. 10. After the typical 10-second acquisition time, the GUI of FIG. 11 or FIG. 12 may appear. The GUI of FIG. 12 gives the operator the opportunity for another approximately 10-second data acquisition period. If software-detected problems occur during data acquisition, a GUI such as the one displayed in FIG. 11 may appear, notifying the operator of potential problems. These features give the operator more control over the testing procedure, and advantageously provide for error control.

Typically, in one preferred embodiment of the invention, an auditory beeping occurs with R-wave acquisition. If no R-wave beeping occurs or if poor signal amplitude is noted, adjustments in the leads may again be required, and sensing verification should be repeated via the GUI of FIG. 12.

Figure 13:
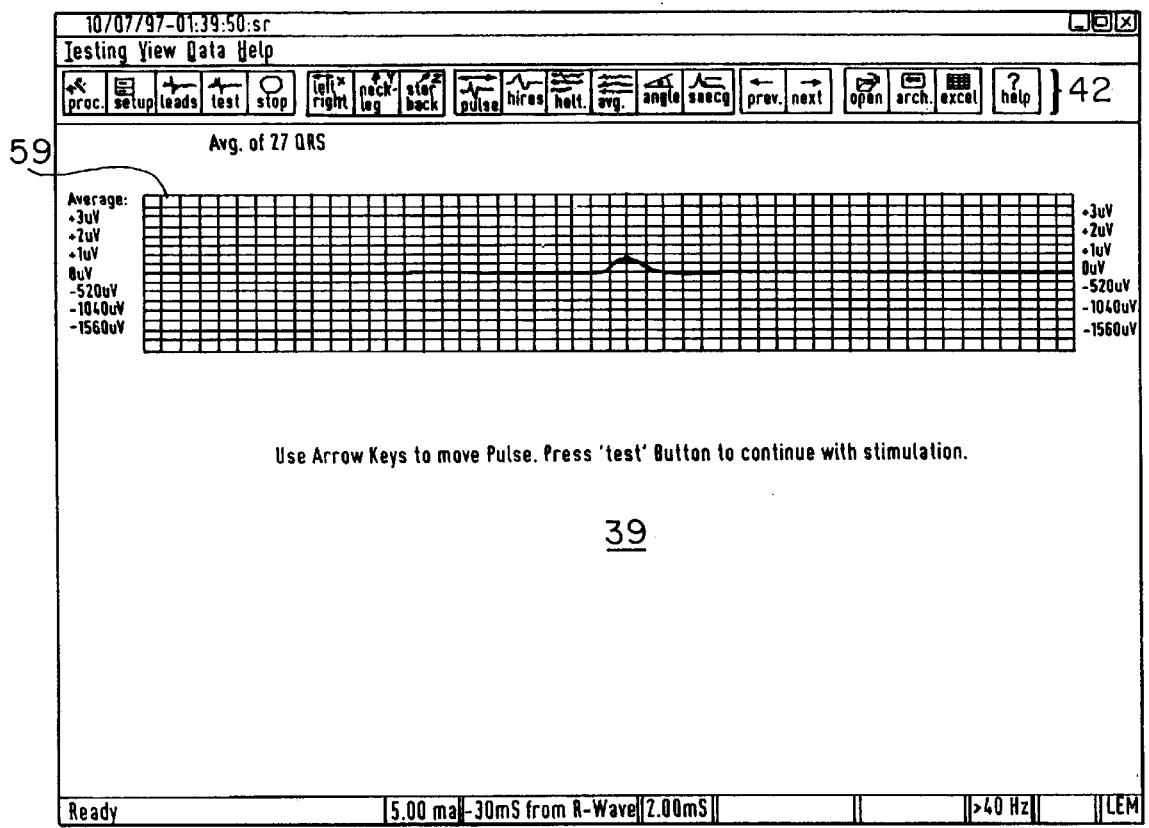
FIG. 13 is the principal GUI generated by the computer and software portion of the invention, depicting a pulse graph.

In situations where the operator is not performing standard protocols, the system will allow the operator to interactively set the pulse position. FIG. 13 is a graphical depiction of pulse 59 on display area 39. Under these circumstances, the operator may use the cursor keys on the keyboard (not shown), coupled to computer 27 (not shown in FIG. 13), to position the pulse location using an average of the QRS complex signals received during sensing verification.

In one preferred embodiment, the final step in the performance of the test sequence function involves performing and recording the test. Prior to performing and recording the test, the software will represent the GUI prompt of FIG. 14. This will allow the operator to control the timing of the test to ensure that both patient 35 and the operator are ready to proceed.

Figure 14:
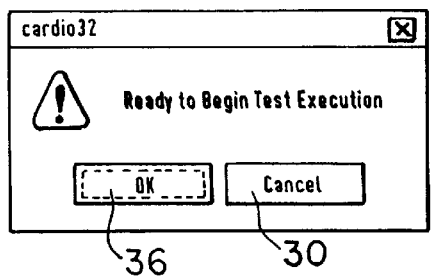
FIG. 14 is the "Ready to Begin Testing Execution" GUI generated by the computer and software portion of the invention.
Figure 15:
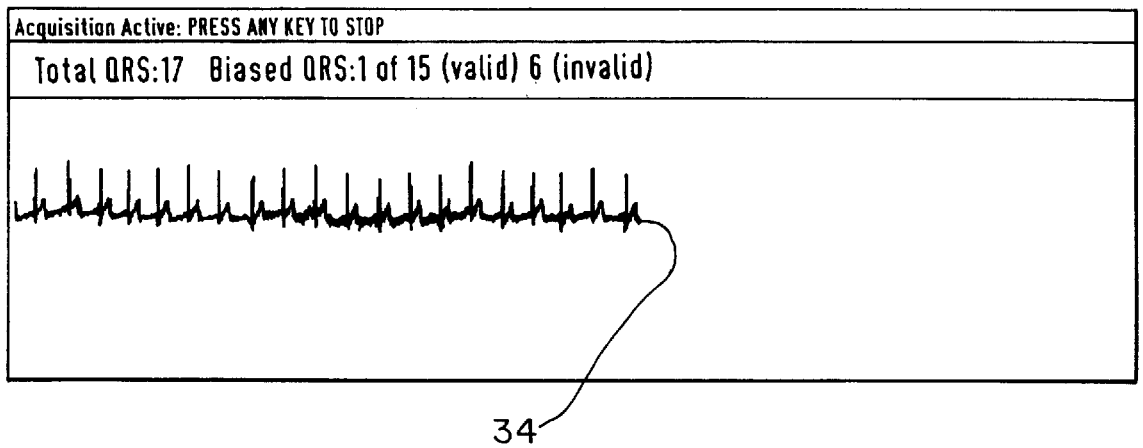
FIG. 15 is the "Acquisition Active" GUI generated by the computer and software portion of the invention, depicting realtime R-wave acquisition.

When the "OK" 36 selection is made from the GUI of FIG. 14, the GUI of FIG. 15 is generated, graphically depicting the R-wave 34 in real time. If "Cancel" 30 is selected, the operator is returned to the previous screen. The system is configured to emit an audible beep synchronously with each R-wave sensed. As indicated on the GUI of FIG. 15, pressing any key of the computer keyboard will halt the performance test sequence. If a key is depressed during the test sequence, the GUI notification screen of FIG. 16 appears, notifying the operator what has occurred.

Figure 16:
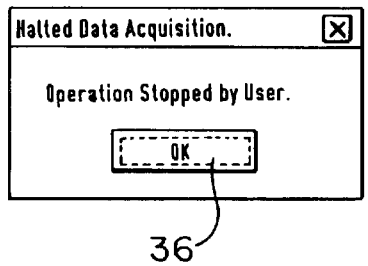
FIG. 16 is the "Halted Data Acquisition" GUI generated by the computer and software portion of the invention.
Figure 17:
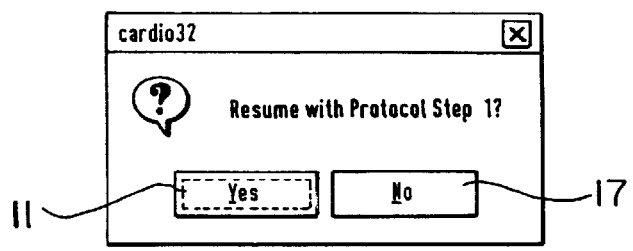
FIG. 17 is the "Resume with Protocol" GUI generated by the computer and software portion of the invention.

This invention anticipates that several other events may occur that would halt acquisition, and similar GUIs to the GUI depicted in FIG. 16 will report such termination of the test procedure. For example, if R-wave sensing is indicated at a rate greater than 180 beats per minute, the test will automatically be halted. Further, if the invention is having difficulty sensing the R-wave, or the R-wave is in any way irregular, the test will be halted. If the test is interrupted during the execution of a test sequence, the sequence may be restarted at the beginning of the interrupted test by selecting "Yes" 11 from the GUI notification screen of FIG. 17, which will be displayed after the test sequence is halted. Selecting "No" 17 from the GUI of FIG. 17 causes the system to return to the main menu screen of FIG. 4. If any of the remaining menu items in drop-down menu 48 are selected, a shortcut to a previously-described procedure is executed. If "Quit" 19 (see FIG. 5) from Testing drop-down menu 48 is selected, the software program is closed.

Figure 18:
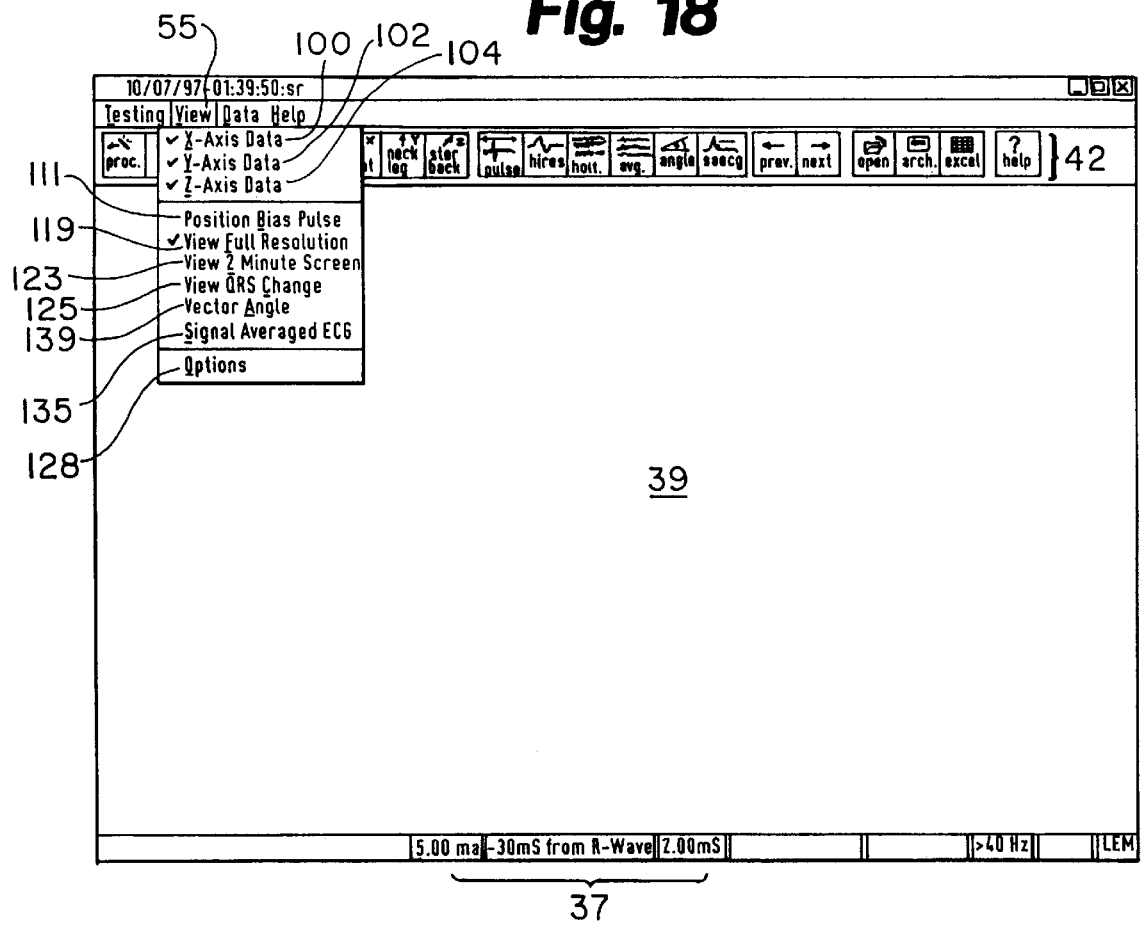
FIG. 18 is the principal GUI generated by the computer and software portion of the invention, depicting the "View" drop-down menu engaged.

FIG. 18 shows the View drop-down menu 55 engaged. View drop-down menu 55 provides access to functions required to select viewing options for data acquired or loaded from disk. Each test performed by the subject of the invention records 3 channels of data. The placement of electrodes (see FIG. 2) allows these signals to record far-field ECG in roughly orthogonal directions. This advantageously provides for a data representation that defines the signal in three dimensions. Axes have been labeled X, Y, and Z. The X signal is recorded, for example, from left lead 1 to right lead 2, with left lead 1 being the positive direction. The Y signal may be recorded from neck lead 5 to leg lead 6, with neck lead 5 being the positive direction. The Z signal may be recorded from back lead 4 to sternum lead 3, with back lead 4 being the positive direction. Other configurations may be possible, depending upon the judgment and needs of the patient and operator. In addition to the three required signals, at least two additional signals are preferably calculated. The X, Y, and Z signals are combined to produce a magnitude and direction signal. A magnitude signal can be used to detect signal variation independent of direction. A direction signal can be used to detect signal variation independent of magnitude. The upper portion of View drop-down menu 55 contains selectable options for each of the signals X 100, Y 102, and Z 104. The options appear checked on the GUI when they are selected. These selections allow the medical professional to select which signals are displayed during certain viewing modes. The lower portion of the pull-down menu contains the viewing modes. Each mode allows the user to view the current data set in a different way. The viewing modes, as they appear on drop-down menu 55, are "View Full Resolution," 119, which displays the X, Y, and Z signals at high resolution on monitor 23; "View 2 Minute Screen" 123, which displays a selected signal compressed into two minutes per screen; and "View QRS Change" 125, which displays the selected signals with normal average, biased average, and difference depictions. Selection of "Vector Angle" 139 displays the angular velocity and direction change of the average signal. "Position Bias Pulse" 111 displays the average of the selected signals, along with an indicator of pulse position. This advantageously allows interactive positioning of stimulation by the medical professional performing the diagnostics.

"Signal Averaged ECG" 135 displays signal-averaged ECG information for normal, biased, and difference signals.

Typically, in the application of signal-averaged ECG 135, of primary importance to the medical professional is the flat area immediately following the QRS complex, ST segment 133. ST Segment 133 is targeted because of its lack of signal in normal people (see FIG. 31). This lack of signal allows the recognition of the presence of very small-amplitude signals that can occur in people with conduction problems indicative of a susceptibility to arrhythmia or other cardiac tissue abnormality. Further abnormal signals may also exist within the QRS and be masked by the higher-amplitude signal present there. Since this invention has the ability to perform comparative analysis between stimulated and non-stimulated beats, a much greater sensitivity may be achieved in areas where a higher natural signal is also present. Additionally, by examining various areas of the QRS complex, information regarding size and position of conduction alteration may also be evident.

Figure 19:
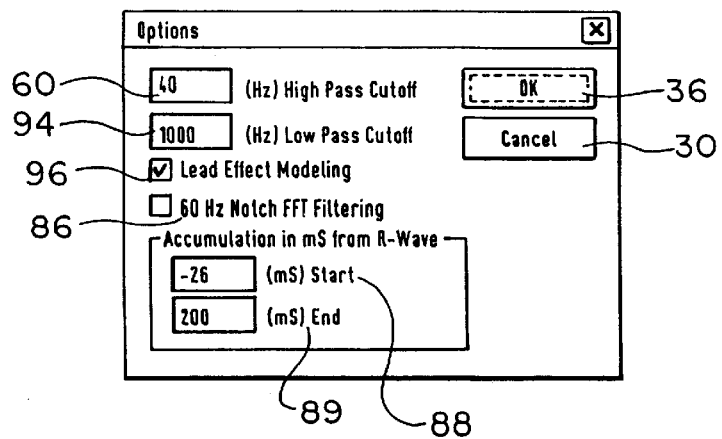
FIG. 19 is the "Options" GUI generated by the computer and software portion of the invention.
Figure 20:
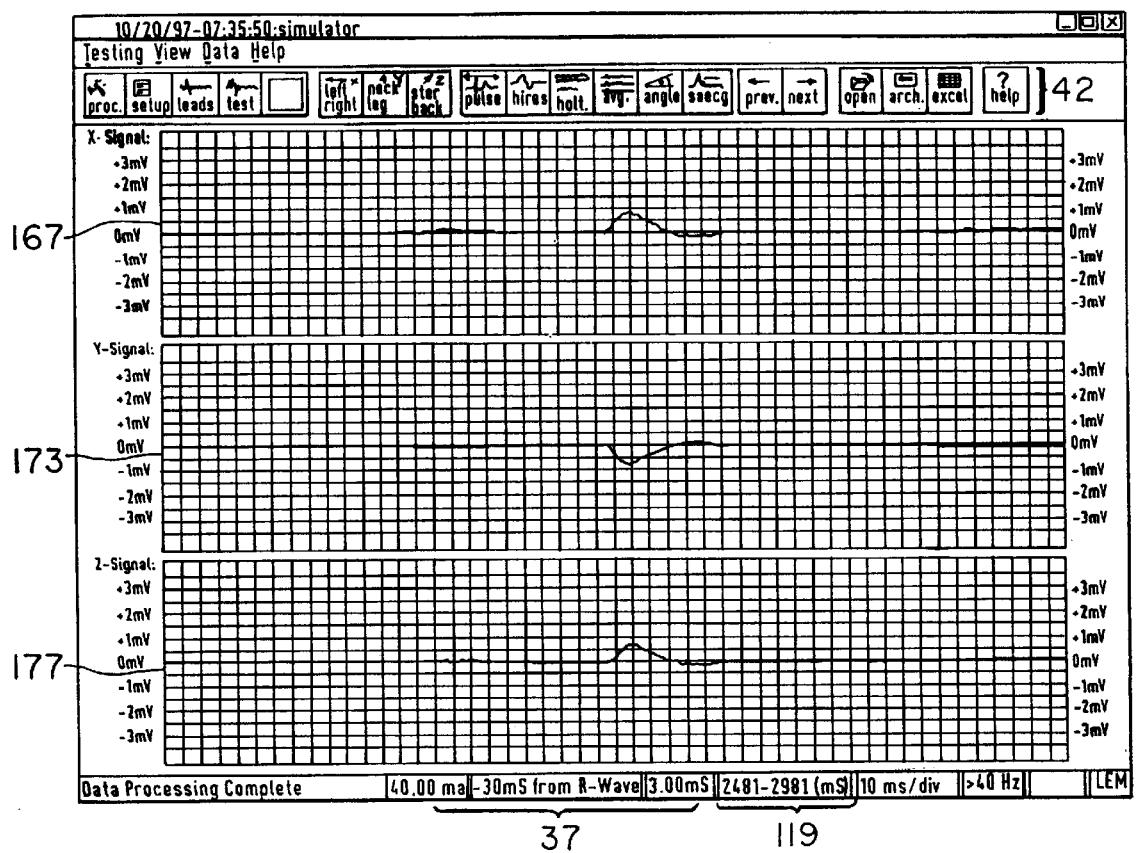
FIG. 20 is the "Simulator" GUI generated by the computer and software portion of the invention.

If "Options" 128 menu selection is made from View drop-down menu 55, the GUI of FIG. 19 is displayed. "Option" 128, which is selectable by the GUI, is represented in FIG. 19. This function allows for better interpretation of the data accumulated. The "High-Pass Cutoff" option 60 of the GUI in FIG. 19 can be set to use a fast-fourier transform (FFT), to filter out frequencies lower than those indicated prior to averaging. A zero setting disables high-pass filtering altogether. Low-pass cutoff 94 uses an FFT to filter out frequencies higher than those indicated prior to averaging. A setting of 1,000 disables low-pass filtering. Advantageously, lead effective modeling (LEM) can be selected in the GUI represented in FIG. 19. If LEM box 96 is checked, in a preferred embodiment, a 20-millisecond model of the impulse artifact is constructed, based on the first four simulations. This model is subtracted from subsequent simulations to reduce artifact in the displayed information. Any voltage shifts created during stimulation are also modeled and removed. LEM and this correction algorithm greatly reduce artifact created by stimulation. A muscle response correction algorithm may also be implemented by the invention to advantageously correct for signal artifacts during stimulation and acquisition cycles. Using this technique stimulation is provided to the patient within an LEM time period between the T and P waves, at the beginning and periodically throughout the stimulation and acquisition process. Response to the stimulations is determined up to about 50 milliseconds for each stimulation. LEM is then created by combining the response of the stimulations during this period to generate a response signal, whereafter the signal is used to mathematically attribute noise generated by electrical artifact and muscle activity. Also GUI selectable is a "60-Hz Notch FFT Filtering" 86 option, which advantageously filters out frequencies at the 60-Hz rate prior to averaging. Accumulation Start time 88 and End time 89 can also be input on the GUI indicated in FIG. 19. Accumulation Start time 88 controls the starting range for the accumulated difference measurement on the average screen. The Accumulation End setting 89 controls the ending range for the accumulated difference on the average screen. An exemplary result of selecting "View Full Resolution" mode 119 is depicted in FIG. 20. Signal characteristics X 167. Y 173 and Z 177 are graphed independently. Again, status bar 37 indicates the various selected parameters previously discussed.

Figure 21:
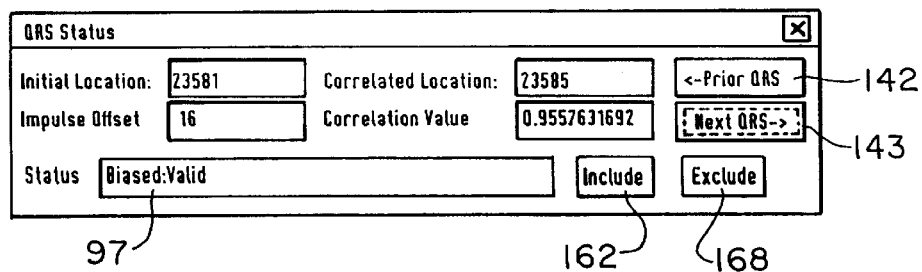
FIG. 21 is the "QRS Status" GUI generated by the computer and software portion of the invention.

Individual QRS status may be determined from the GUI of FIG. 21. The various options in the QRS Status window 97 are as follows: if the status indicated is "Biased," that means that the QRS complex has a stimulation associated with it. If it is "Normal," the QRS does not have an associated stimulation. The parameter "Valid" in status window 97 means that the QRS has past selection criteria which is included in the averaging. If the LEM stimulation is indicated (not shown), this means that the QRS complex is used for LEM. If "low correlation" is indicated (not shown) in status window 97, the QRS complex was too low and, therefore, was not used in the averaging. If there is a "Bad Interval" indication (not shown), then the preceding or following interval changed by greater than 300 milliseconds. If a "high-rate" status indication is indicated (not shown), the pulse rate exceeded 180 beats per minute and the QRS complex was not used in the averaging. If "manual exclusion" is indicated (not shown), that means that the QRS complex was manually excluded by the operator. If "Bad pulse Positioning" is indicated (not shown), the pulse position exceeded the tolerance set by the medical professional or the default tolerance. Further, it is possible to manually include or exclude a particular QRS from the averaging statistics by using the "Include" 1.62 and "Exclude" 168 selection buttons on the GUI of FIG. 21. A previous QRS complex may be viewed by selecting the "prior QRS" button 142. The next QRS complex can be viewed by the selection of the "Next QRS" button 143.

Figure 22:
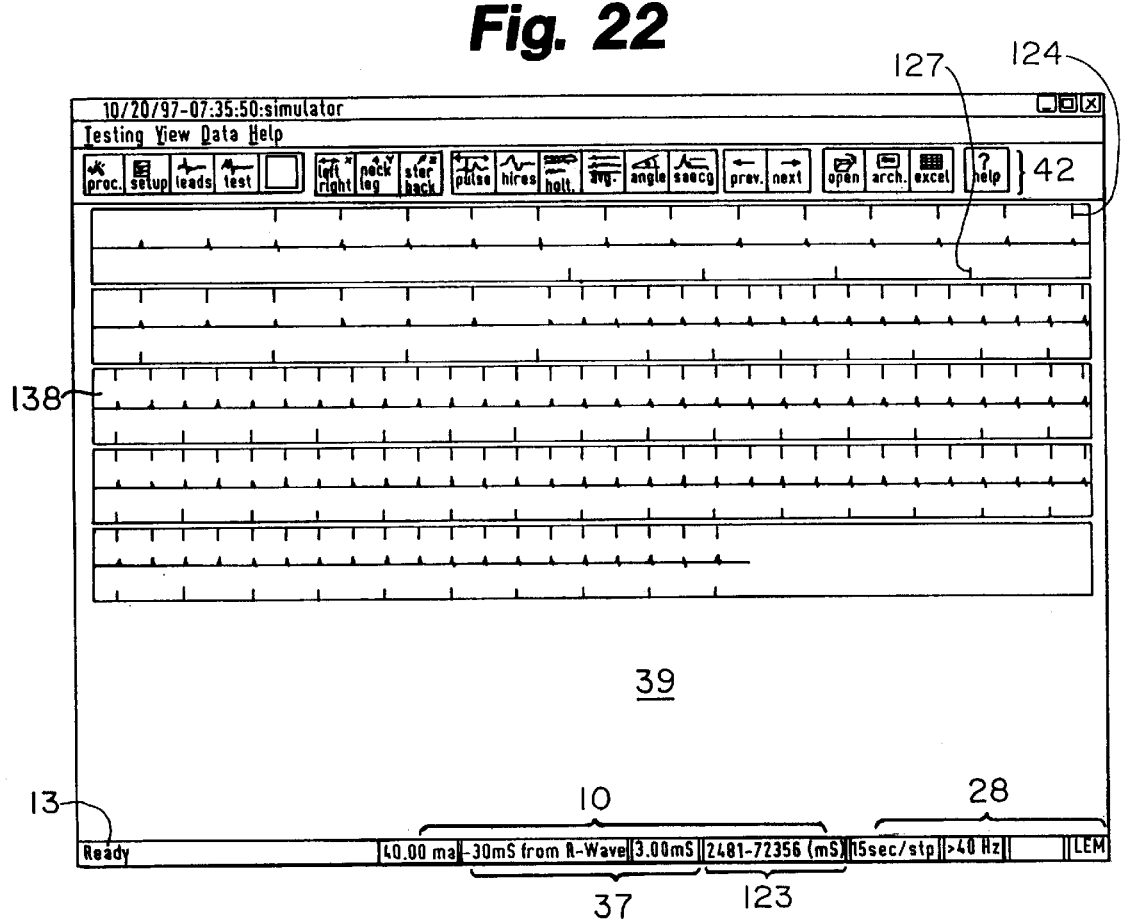
FIG. 22 is the "Simulator" GUI generated by the computer and software portion of the invention, depicting a further display option.

An exemplary result of selecting "View 2 Minute Screen" 123 is depicted in FIG. 22. The 2 Minute Screen mode allows the medical professional to view a selected channel in an overview mode. In this mode, a two-minute portion of the selected channel 138 is displayed on display area 39. R-wave correlation points 124 and stimulation points 127 are indicated on the display area of FIG. 22. R-wave correlation points 124 are longer, white indications (not shown) above the waveform. Stimulation points 127 are red indications (now shown) below the waveform. Note that both Full Resolution 119 and View 2 Minute Screen 123 modes display the current start and end time for the displayed portion of the test on status bar. 37 at the bottom of the relevant GUI. Advantageously, as the operator scrolls through the data, these values change to indicate the portion of data currently being displayed.

Figure 23:
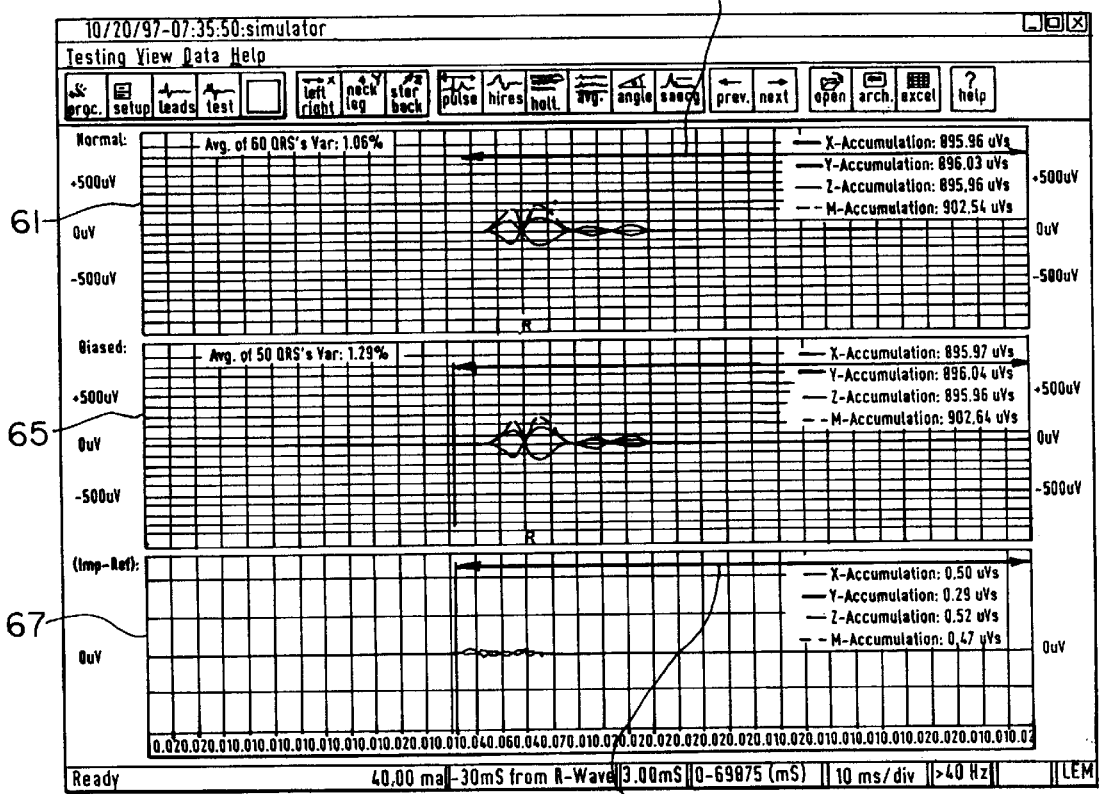
FIG. 23 is the "Simulator" GUI generated by the computer and software portion of the invention, depicting a further display option.
Figure 24:
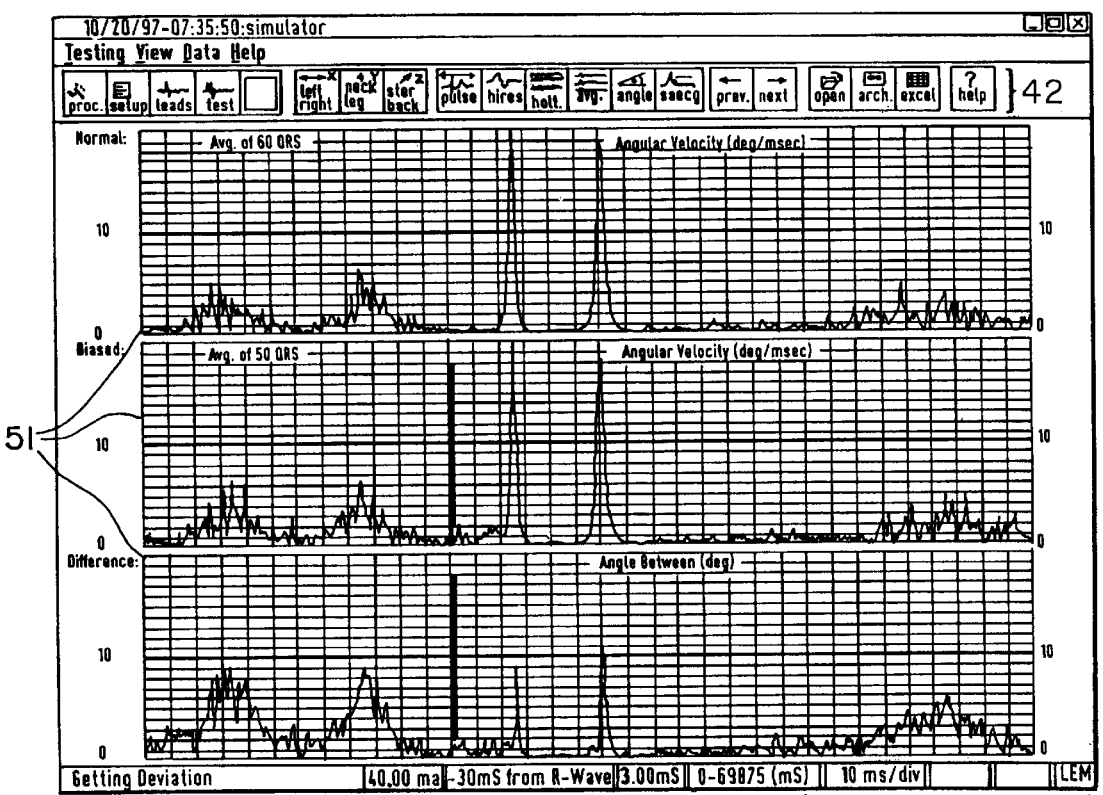
FIG. 24 is the "Simulator" GUI generated by the computer and software portion of the invention.

An exemplary result of selecting "View QRS Change" 125 mode is depicted in FIG. 23. In FIG. 23, the upper graph 61 shows the average of all nonbiased QRS complexes. The middle graph 65 shows the average of all biased or stimulated QRS complexes. The lower graph 67 is the difference graph that shows the difference between the normal and biased waveforms. Statistics identifying the accumulated area under each curve are displayed on the right. A double-end arrow 33 on the lower graph indicates the range over which the statistics were generated. The end points can be adjusted in the view options window. The Difference graph contains cumulative Difference results along the bottom of each 10-millisecond region, based on the magnitude signal. FIG. 24 depicts the Vector Angle GUI. Vector Angle mode displays angular information 151 not reflected in the magnitude signal. The Vector angle mode displays changes in the direction of the electrical signal, whereas the Magnitude mode displays changes in the amount of electrical signal.

Figure 25:
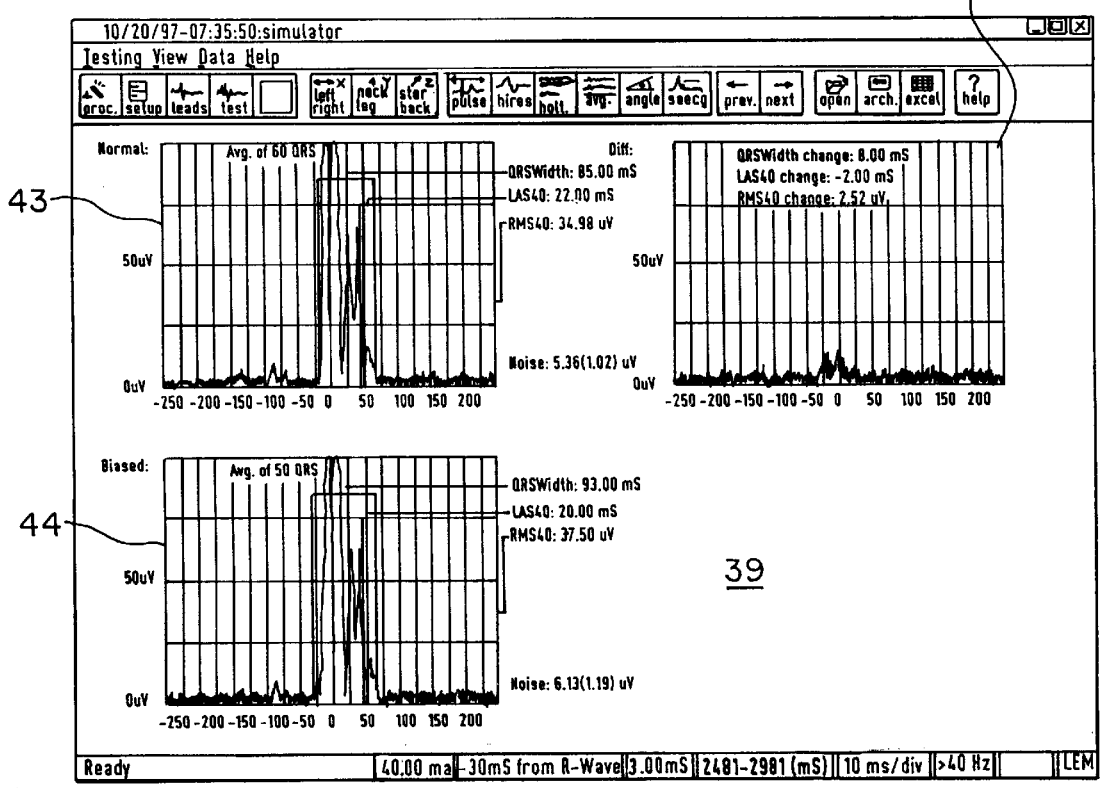
FIG. 25 is the "Simulator" GUI generated by the computer and software portion of the invention.
Figure 26:
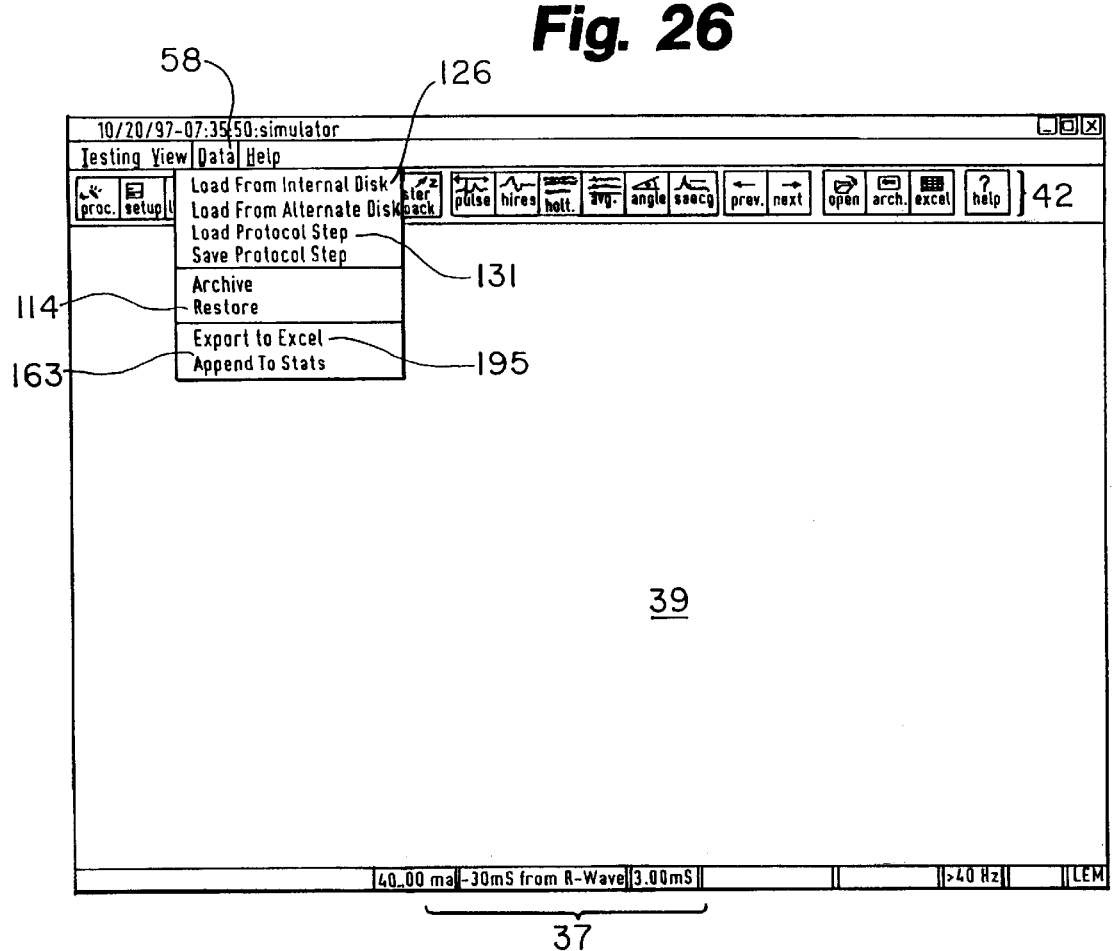
FIG. 26 is the principal GUI generated by the computer and software portion of the invention, depicting the "Data" drop-down menu engaged.

When the Signal Averaged ECG menu selection is made from View drop-down menu 55, the GUI of FIG. 25 is displayed on computer screen 23. The various graphs represent the Signal Averaged information for the Normal 43 and Biased 44 QRS complexes, along with the Difference 45 between the two. Standard QRS, LAS 40 and RMS 40 calculations can be made. Noise threshold is displayed along with the standard deviation of the noise, as can be seen on the GUI of FIG. 25.

Another drop-down menu 46 is the Data drop-down menu 58. Data drop-down menu 58 provides access to functions required for loading previously acquired data from storage, such as a hard disk located in computer 27, or from removable storage, such as a Zip™ disk or other removable storage media. Configuration of protocol steps is also supported here, along with typical backup and restore functions.

Figure 27:
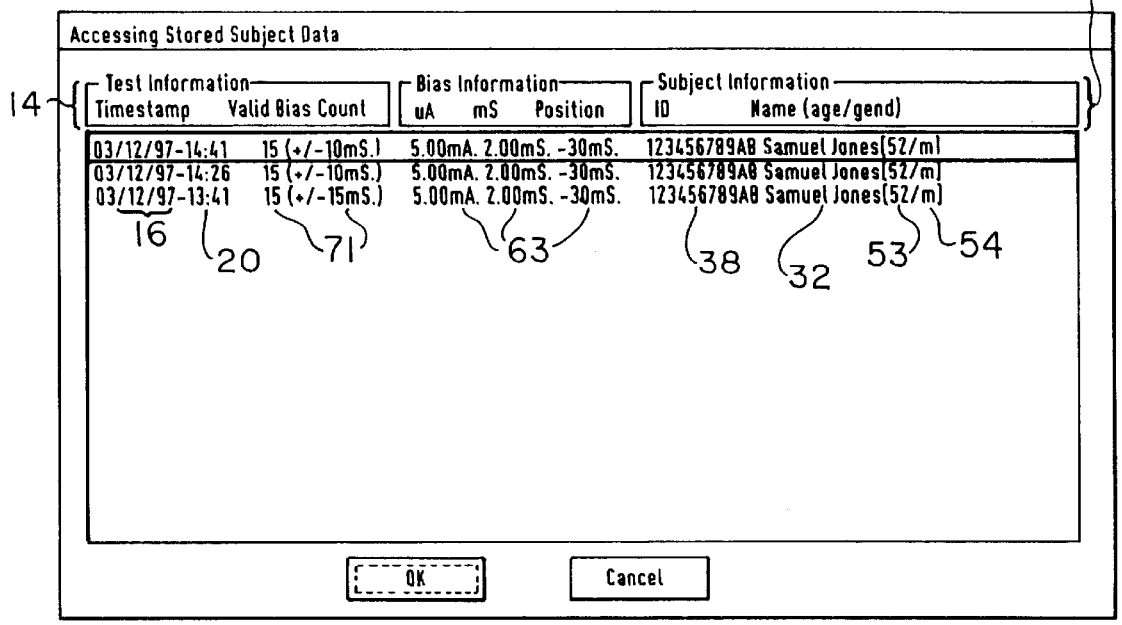
FIG. 27 is the "Accessing Stored Subject Data" GUI generated by the computer and software portion of the invention.
Figure 28:
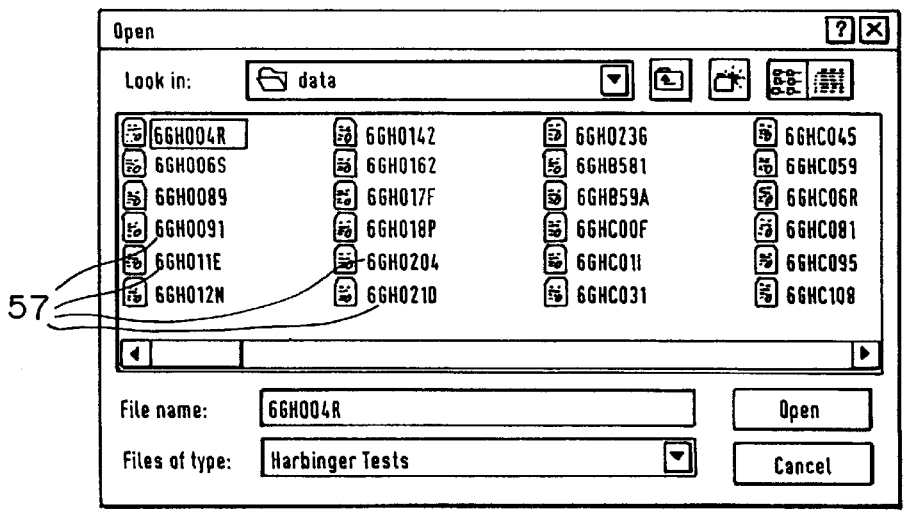
FIG. 28 is the "Open" GUI generated by the computer and software portion of the invention.

FIG. 27 is a GUI depiction of an exemplary menu for stored data. The date 16 and time 20 of acquisition, the identification 38 name 32, age 53, gender 54, bias information 63, R-wave sensitivity, and valid count 71 are all identified for reference, as can be noted in the upper area 14 as depicted in FIG. 27. Selecting "Load From Internal Disk" option 126 from drop-down menu 58 reveals the GUI depicted in FIG. 28. The GUI of FIG. 28 depicts a variety of test data 57 that can be selected.

Figures 29, 30:
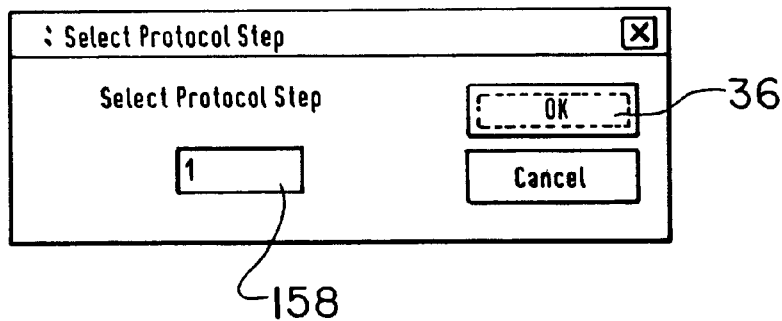
FIG. 29 is the "Protocol Steps" GUI generated by the computer and software portion of the invention.
FIG. 30 is the "Select Protocol Step" GUI generated by the computer and software portion of the invention.

If "Load Protocol Step" 131 is selected from the drop-down menu, the GUI of FIG. 29 is displayed. This function loads an identified protocol step 69 into the current test configuration. The GUI dialog box allows the operator to identify the protocol step to load. Current patient information is not changed. To select a test configuration as a protocol step, the GUI of FIG. 30 is used. The protocol step is entered into "Select Protocol Step" window 158 of the GUI, and "OK" 36 is selected to save the step.

Selection of "Restore" 114 from Data drop-down menu 58 restores data from an external media, such as a Zip™ disk, back to the internal hard drive of computer 27. Further, using the "Export" 195 command, data can be exported to certain spreadsheet software programs.

The "Append To Stats" option 163 can be selected to append the statistics of the current configuration parameters to the file. Advantageously, this option allows all test data sets in the current drive and directory to be processed using the current processing parameters and appended to the selected text or TXT, file. This useful option allows for batch processing and results based on altered settings.

Another menu 46 is Help drop-down menu 60. Full index and search capabilities of Help information is available. Further, on-line help, such as information gatherable through the Internet, is also anticipated.

Figure 43:
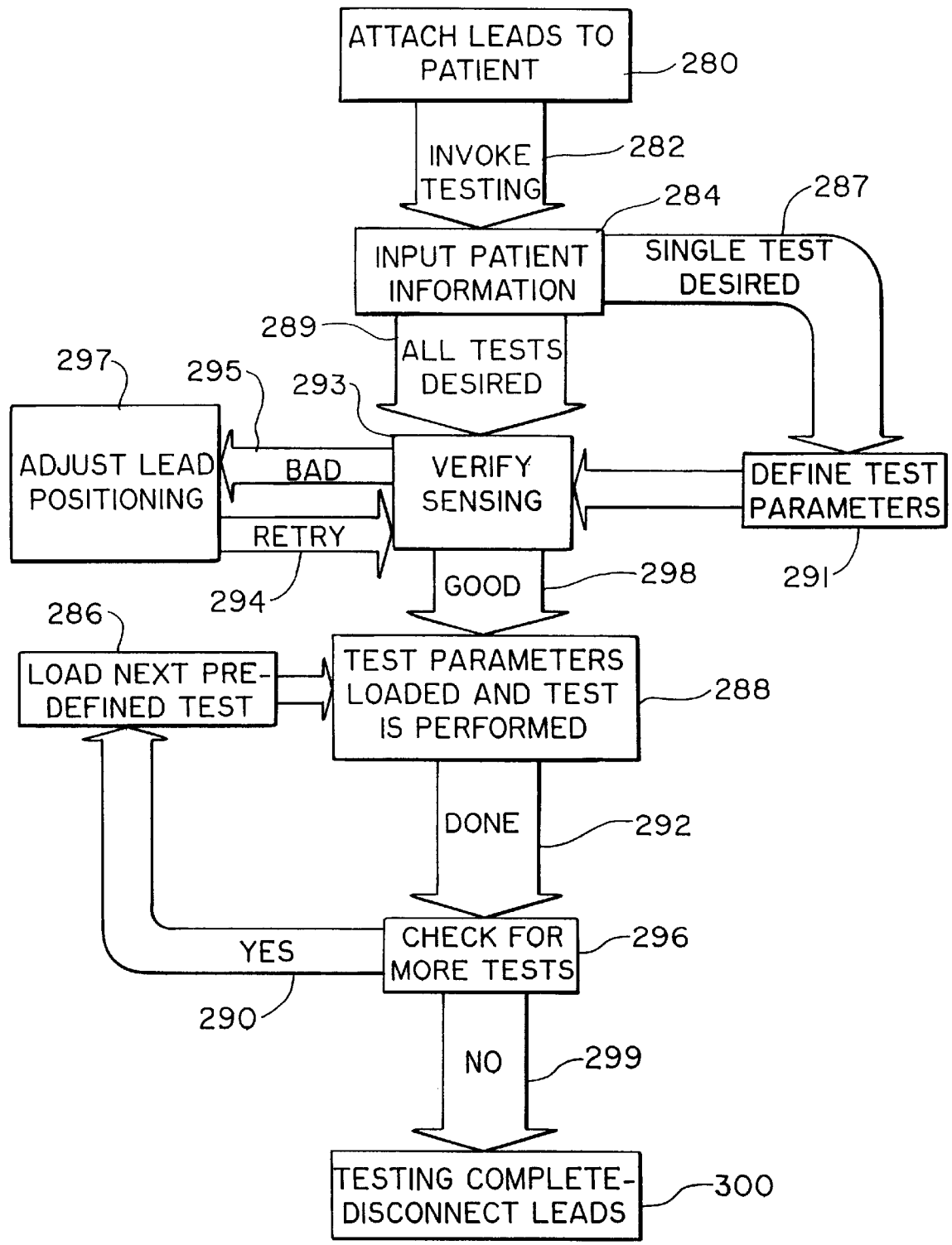
FIG. 43 is a high-level flow chart of the operation of the software.

A high-level operator flow chart for the software described above appears in FIG. 43. A typical embodiment of the method of using the software begins at the Attach Leads lo Patient stage 280. As described above the operator will then Invoke Testing 282 and Input Patient Information 284. If only a single test is desired, path 287 is taken, wherein the operator has a chance to Define Test Parameters 291. Otherwise, the operator has the choice of selecting All Tests Desired 289 and proceeding directly to Verify Sensing 293. If Verify Sensing 293 is Bad 295 then the lead positioning can be adjusted 297, and the verified sensing retried 294. Once the sensing is Good 198, the test parameters are loaded and the test is performed 288. Once the test is completed 292, there is a chance for the operator to see if more tests need to be performed 296. If "Yes" 290, then the next predefined tests are loaded 286, and the operator is returned to Test Parameters Loaded and Test is Performed 288. If no further tests are to be formed at the 296 state, the "No" path 299 is selected and the test is completed and leads arc disconnected 300.

FIG. 44 is a depiction of the test control and data acquisition software flow chart. Raw data received from lead system 12 is received at the Realtime Test Control and Monitor Software 310, along with Realtime R-Wave Indicators 306. Realtime Test Control and Monitor Software 310 then controls and relays this information to generate GUIs to make a realtime display 312 on monitor 23. Inputs from the control system can control other test features, as well, such as User Abort Control 304 and the user's ability to perform Test Configuration 308. Realtime Test Control and Monitor Software 310 can also send the Raw Data 303 to storage 313, and save Subject & Test Information 315.

Figure 45A:
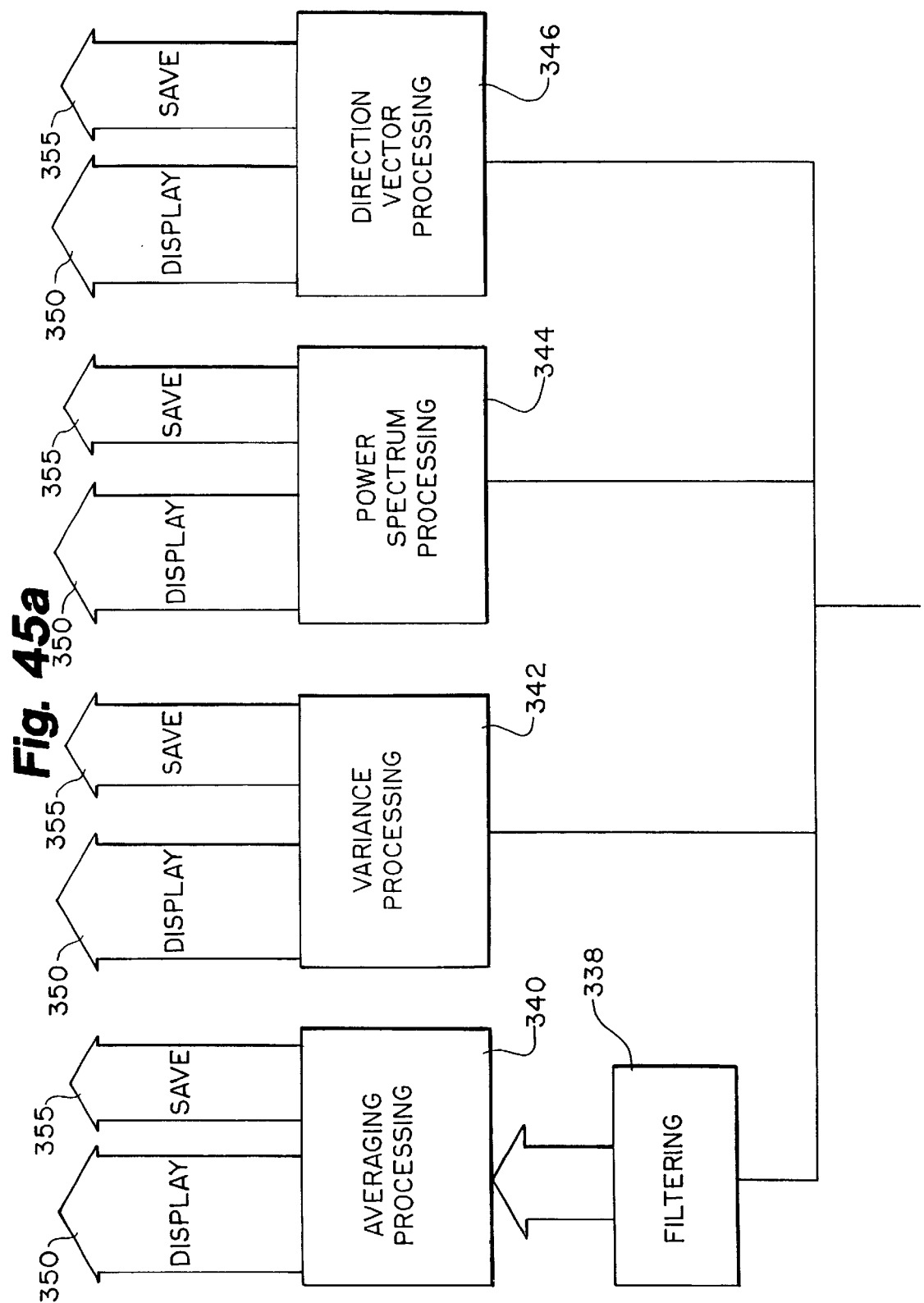
Figure 45B:
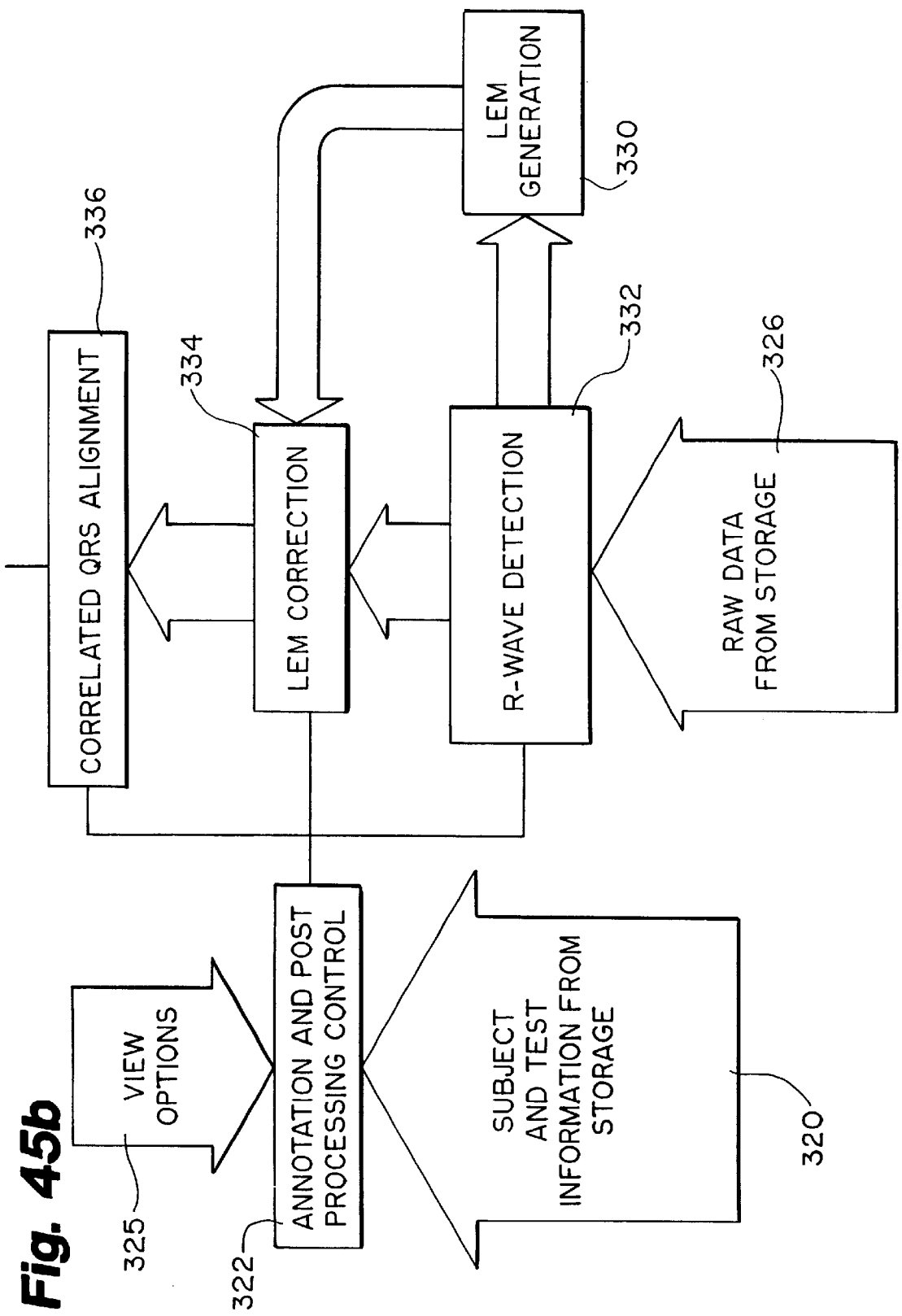

FIG. 45 depicts the software flow charts of the post-processing software. Annotation and post-processing control 332 controls View Options 325 as described above, and subject and test information retrieval from storage 320. Raw data from storage 326 is retrieved and analyzed for R-wave detection 332. If LEM generation 330 is requested, then LEM Correction 334 will be performed, and Correlated QRS Alignment 336 performed. Then, one to typically four processing options may be selected. Average Processing 340 can be selected for the data to be analyzed after being filtered through filtering process 338. Then the options of displaying 350 or saving 355 the data are available. If variance processing 342 is selected, the results may be displayed 350 or saved 355. Similarly, if Power Spectrum Processing 344 is selected, the results may be displayed 350 and/or saved 355. Also, Direction Vector Processing 346 may be selected and, again, the resulting information can be displayed 350 and/or saved 355.

Figure 46:
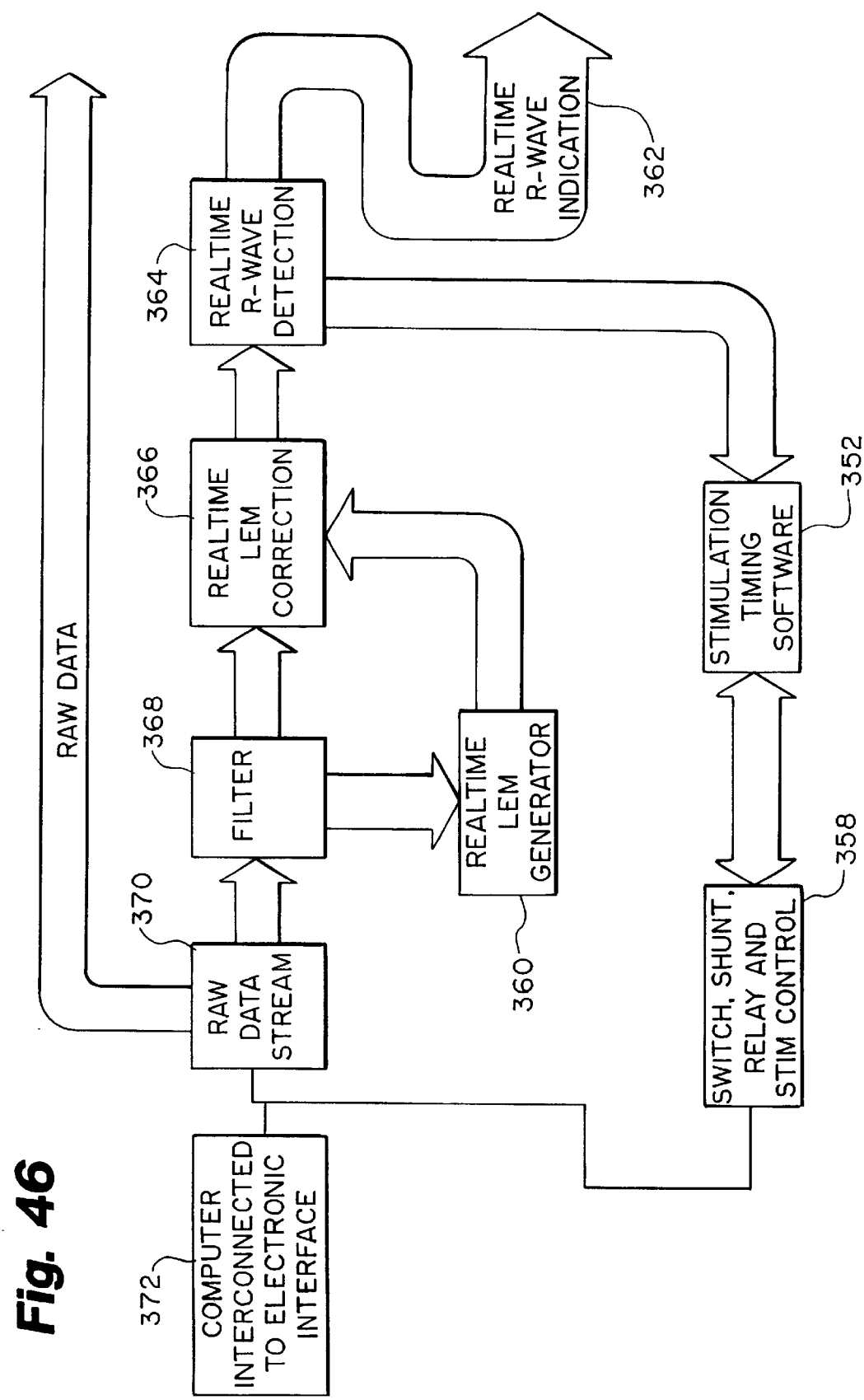
FIG. 46 is a lower-level flow chart of the realtime enter of controls implemented by the software.

FIG. 46 displays the lower-level flow diagram, more particularly, the stimulation timing software and the switch, shunt, relay, and stimulation control features that allow for efficient subpacing stimulation signals to be timely and efficiently administered, as well as to facilitate the ability of the invention to make fast recovery to prepare for the next QRS complex event. Raw Data Stream 370 is filtered by Filters 368 and is sent to Realtime LEM Generator 360, and any realtime LEM correction is made at 366. Realtime R-wave detection is determined at step 364; and, if detected, the realtime r-wave indications are passed on at 362. Realtime R-Wave Detection 364 is also linked with the Stimulation Timing Software 352 that determines the timing of the subpacing electrical pulse. Stimulation Timing Software 352 interacts with the switch on the relay and the stimulation control portion of the software 358. The computer interconnects to the electronic interface as shown at 372.

Figure 36:
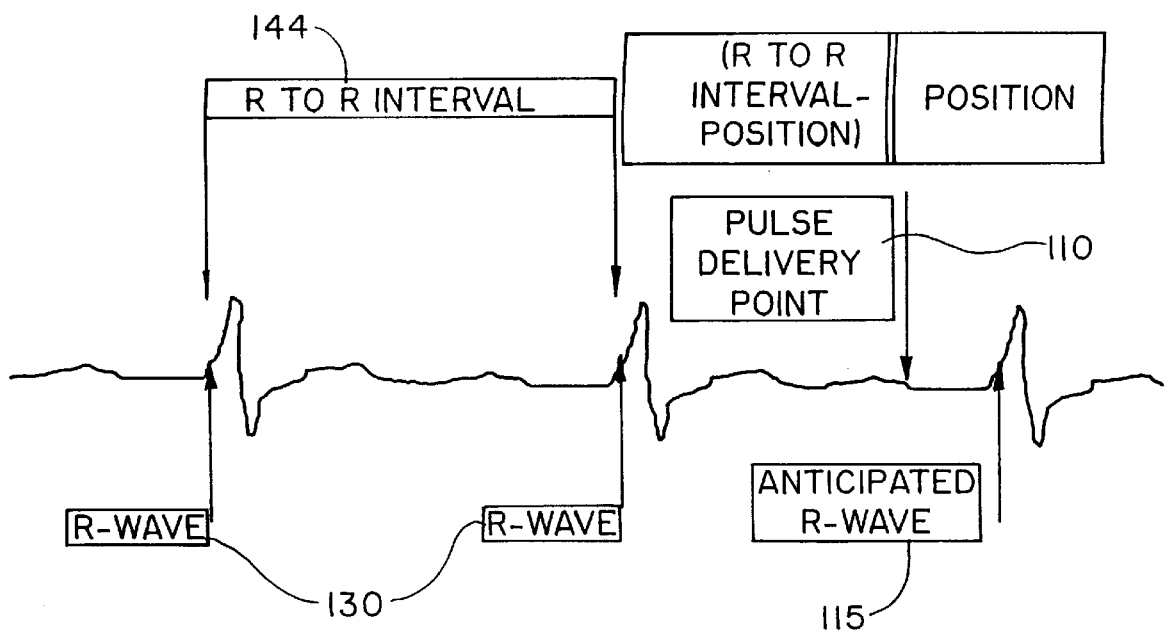
FIG. 36 is an exemplary series of QRS complexes.

FIG. 36 depicts an exemplary series of QRS complexes 130, or R-wave events. As can be seen, interval 144 is defined by that interval from the beginning of one QRS complex to the beginning of the next QRS complex. During the testing provided by this invention, a Pulse-Delivery Point 110 is determined by the invention and a subpacing current is delivered, typically as shown in FIG. 36. There is then the anticipated R-wave 115, based upon two previous R-waves. In one preferred embodiment, the response to the stimulation is determined for a period of up to about 50 ms after the stimulation. Any change in the characteristics of the QRS complex 130 following delivery of the subpacing pulse at delivery point 110 can be used in the diagnosis of a patient's susceptibility for arrhythmia and cardiac tissue abnormality. A desired pulse position with respect to a detected R-wave is configured by the operator. When the intended position and time with respect to a detected R-wave is at or following the R-wave, then the device delivers a pulse after an appropriate-length delay following the most recently detected R-wave. When the intended position and time with respect to a detected R-wave are before the R-wave, then the device uses the previous R-interval 144 to determine an estimated time for delay by subtracting the desired amount from the R to R interval 144. The device then delivers the pulse after the determined delay following the most recently detected R-wave. The computer software is controlled with simulation and data acquisition during testing. During each test, the software delivers stimulation to alternating QRS complexes, based on realtime R-wave detection. Signals are recorded from lead system 12, along with the stimulation and R-wave detection locations. This is monitored and is terminated when the appropriate number of pulses have been delivered in the region identified in the test parameters.

Another process for arrhythmia detection is that of t-wave alternan analysis. This process involves looking for alternations from beat to beat in the signal produced during the t-wave portion of the heart signal. The t-wave is the portion of the heart signal that follows the QRS "contraction" (see FIG. 31) of the heart. The QRS area is called depolarization. The t-wave is called repolarization because the cells are electrically preparing for the next depolarization. T-wave analysis involves computing the "power" of each t-wave and looking for alternations in this power from beat to beat. This phenomenon tends to increase in people prone to arrhythmia. The use of t-wave alternan analysis with the previously-described technique of subthreshold stimulation is anticipated by this invention.

Figure 33:
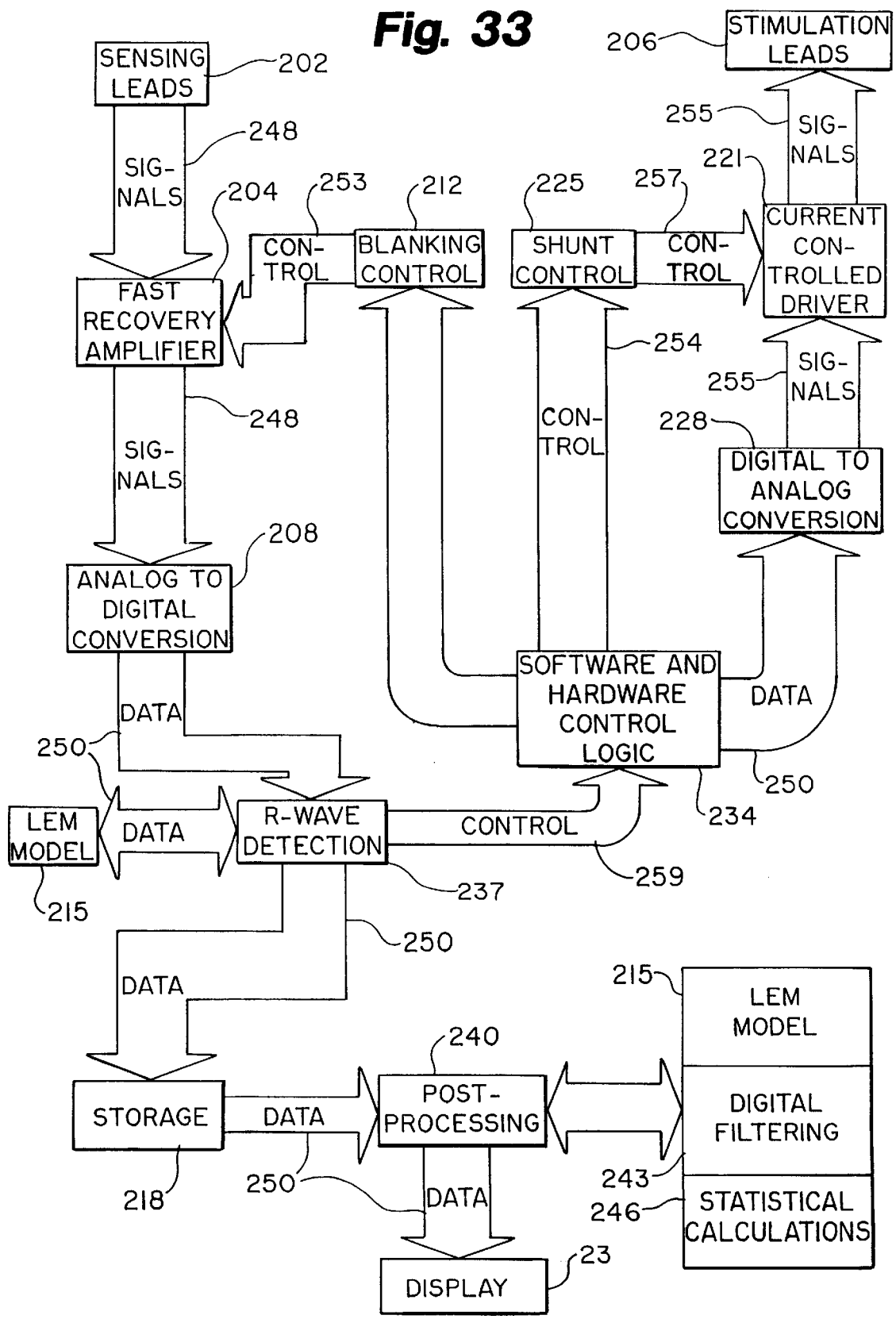
FIG. 33 is a flow chart showing the overall interaction of the invention.
Figure 34:
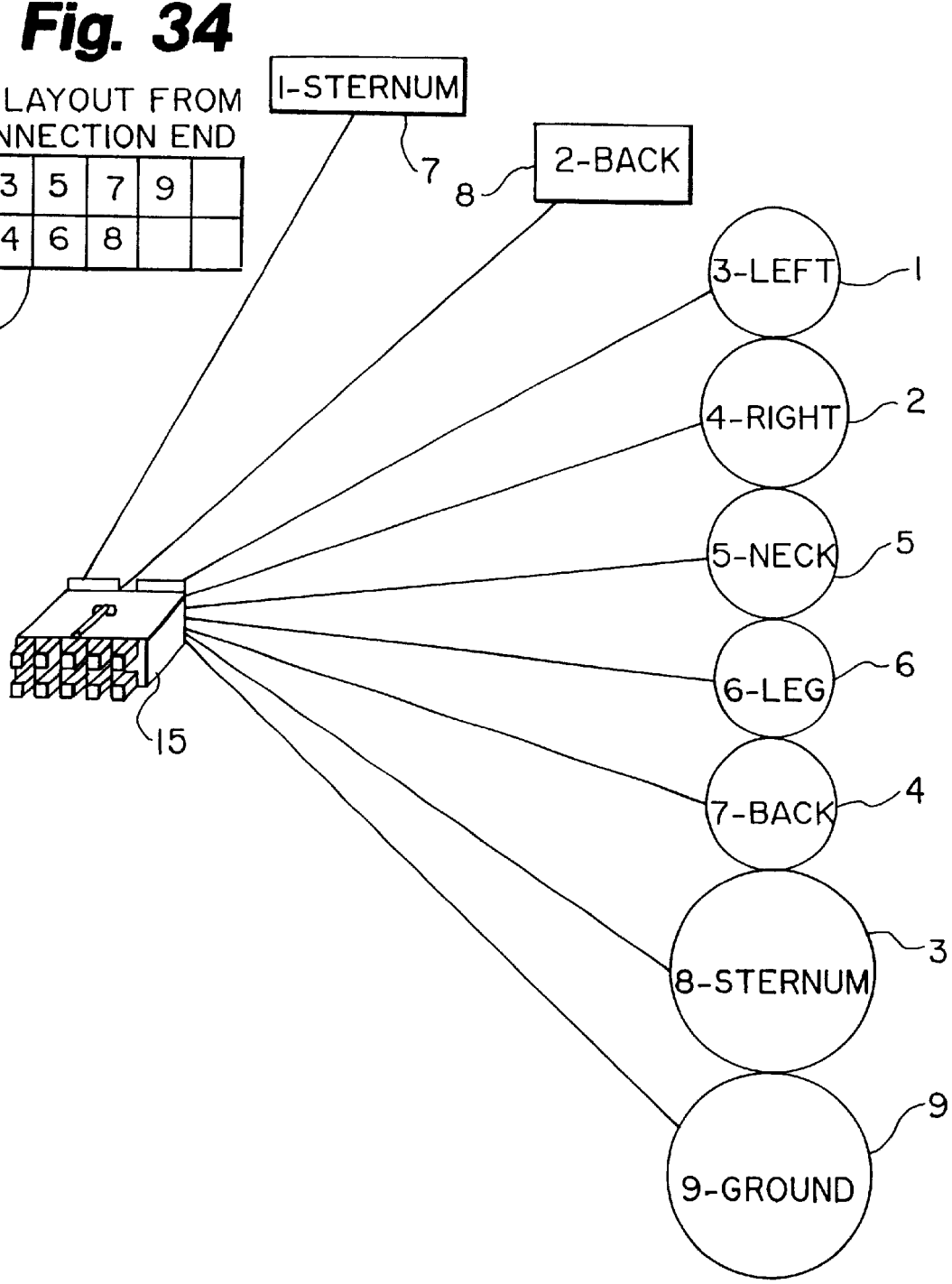
FIG. 34 is a more detailed view of the connector and attached leads, showing pin layout.
Figure 35:
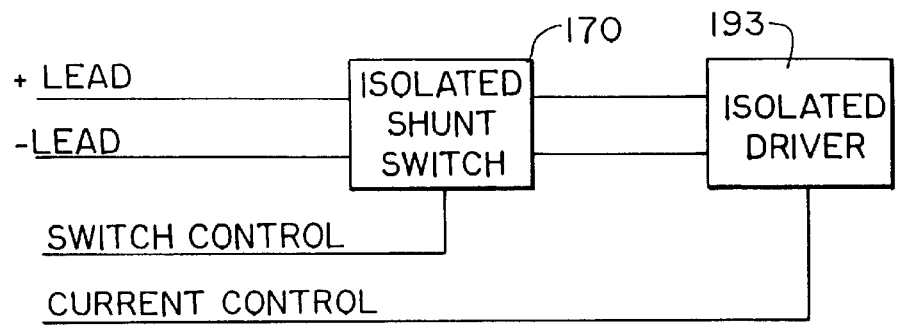
FIG. 35 is a block diagram of the isolated driver and shunting switch, a portion of the electronics interface.

An overview of the operation of this invention can be seen in FIG. 33. Sensing Leads 202 pass received Signals 248 to the fast-recovery amplifier, at which time the Signals 248 are passed to the Analog to Digital converter 208. Thereafter, Data 250 is used to determine R-wave Detection 237 and for LEM modeling 215. Data 250 is also capable of going to Storage 218, and is further used for Post-Processing 240, where data 250 is eventually displayed to computer monitor 23. During the fast-recovery amplifier stage 254, Blanking Control 212, through Control 253, is used to compensate for blanking. This blanking control is initiated through the Software and Hardware Control Logic 234 via Control 253. Control 259 controls the R-wave detection 235 as it is passed to the Software and Hardware Control Logic 234. Software and Hardware Control Logic 234 further controls a Shunt Control 225 via Control 254; and Control 257 controls Current Controlled Driver 221. Hardware and Software Control Logic 234 passes Data 250 to the Digital to Analog Conversion 228, thereafter passing those Signals 255 to the Current Controlled Driver 221. At the appropriate time, Signal 255 is delivered to Stimulation Leads 206. Post-Processing 240 also performs LEM modeling 215, Digital Filtering 243, and Statistical Calculations 246, described in more detail below.

Figure 38:
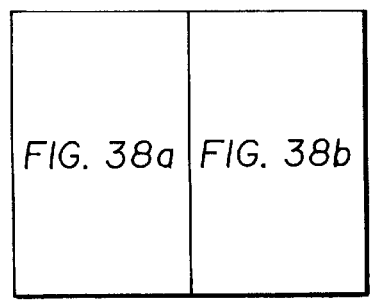
FIGS. 38 and 38a–b is a wire-level depiction of the electronics interface.
Figure 38A:
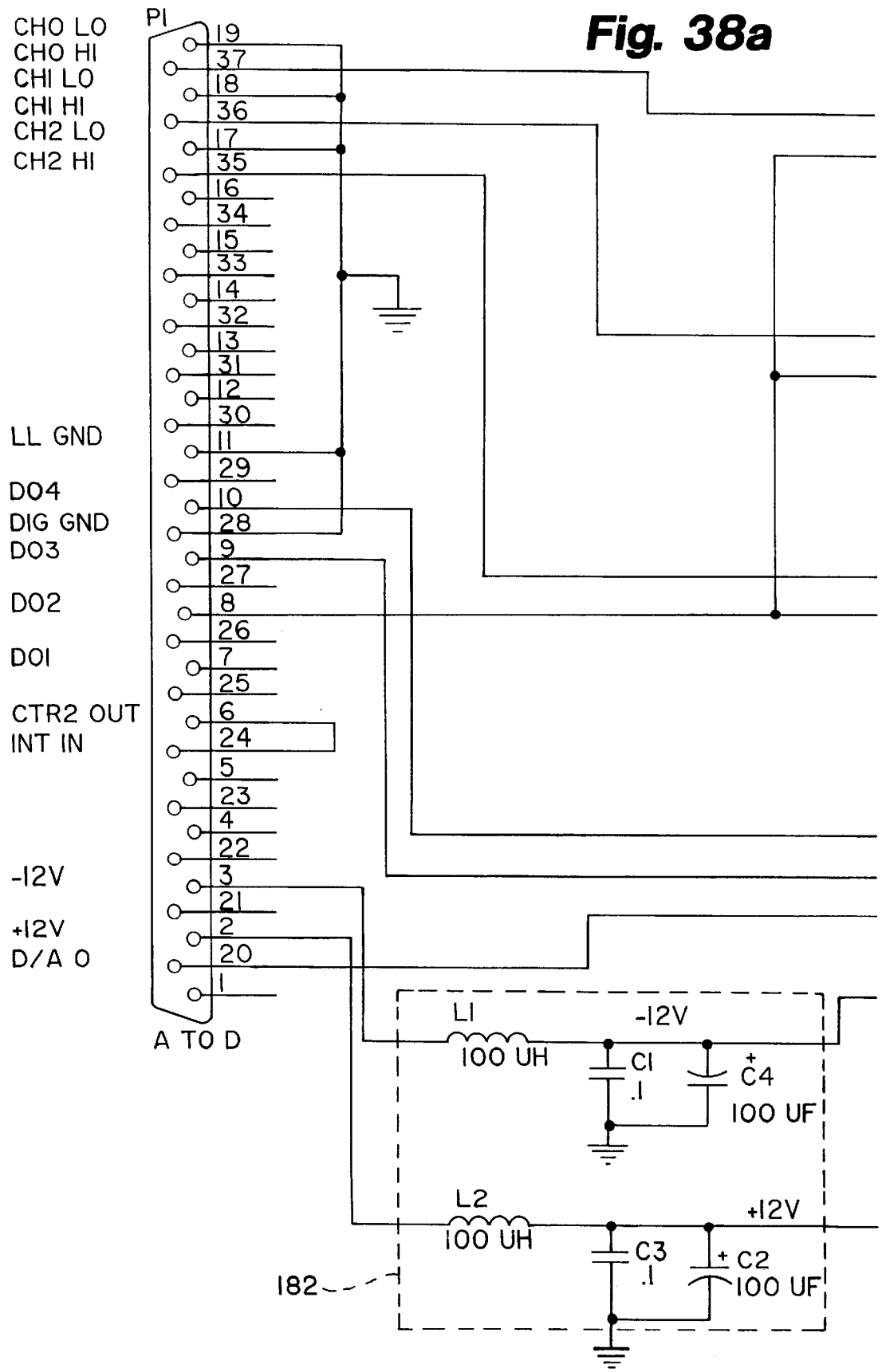
Figure 38B:
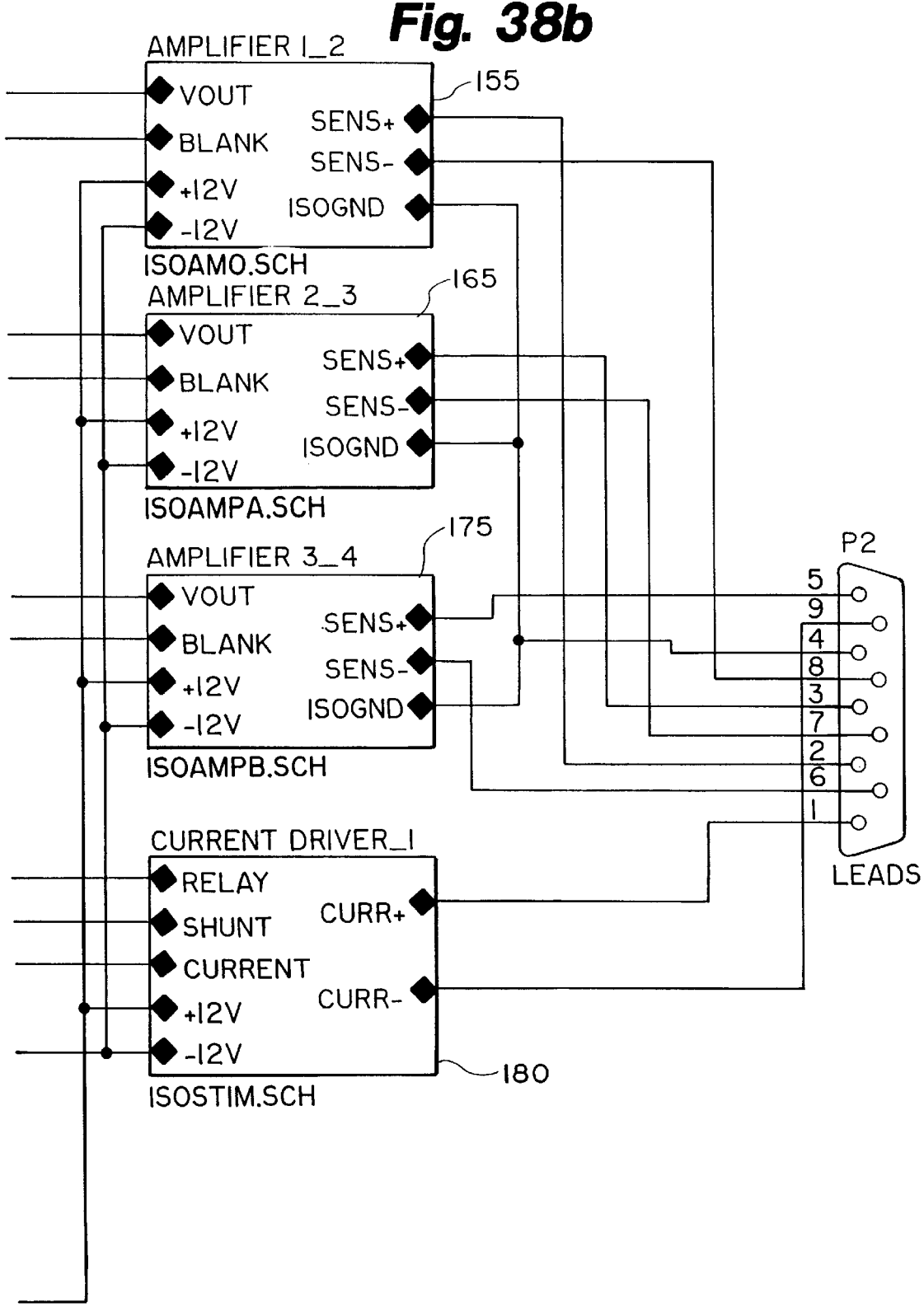

A significant part of the subject invention is the amplifier and driver circuitry located in electronic interface 18. Electronic interface 18 provides amplification of signals received from lead system 12 and amplifies those signals to a level of impedance readable by the computerized data acquisition/control system, such as computer 27. Electronic interface 18 also takes control signals from the computerized data acquisition/control system, such as computer 27, and provides stimulation into lead system 12, as described above. The amplifier circuitry is designed to record lead signals that occur immediately following the injection of energy into the lead system. The recording typically occurs within only several milliseconds of the injection of energy. Fast recovery is important to the system because of the need to sense electrical information very shortly after a stimulation. In one preferred embodiment shown in FIG. 37, each vector X, Y, and Z has its own amplifier, X amplifier 155, Y amplifier 165, and Z amplifier 175. Stimulator 180 controls subpacing pulse delivery in conjunction with computer 27; and the software Power Conditioning Circuit 18 2 powers amplifiers 155, 165, and 175 supplying Stimulator 180 with subpacing current. FIG. 38 is a wire-level diagram of FIG. 37, illustrating this advantageous design.

To provide for such fast recovery, several methods are employed. The sensing leads are comprised of fast-recovery material, such as tin, sodium, silver and silver chloride, or other such material know to those skilled in the art to facilitate rapid dissipation of any energy induced by the system. Further, electronics interface 18 uses a multistage amplification scheme as known to those persons skilled in the implementation of amplifiers, with improvements for fast recovery. FIG. 38 shows a wire-level block diagram of this embodiment of electronic interface 18. In one preferred embodiment, electronic switches are placed between amplification stages, which are used to decouple stages within the amplifier. The amplifier must be switched into its high-impedance mode, with appropriate time allowances for all electrical switching to be completed prior to the application of any energy to the stimulation leads. Similarly when switching back to normal impedance mode, appropriate timings must be used to ensure that all stimulation energy is completely terminated prior to lowering the amplifier impedance. This timing must account for any engaging or disengaging delay in both the amplifier and energy delivery circuits. When the amplifier is in its normal- or low-impedance mode, it has a capacity to store up charge in a very short period of time. Therefore, application of stimulation energy, however short, in this mode will greatly increase undesirable artifact. Therefore, timing is critical in decoupling the amplifier to reduce artifact. Advantageously, switch timing is software-controlled in one preferred embodiment of this invention. Other timing means are known to those skilled in the art. Filtering is implemented by this invention to filter the acquired signal to eliminate possible high frequency, switch-related artifacts.

Figure 39:
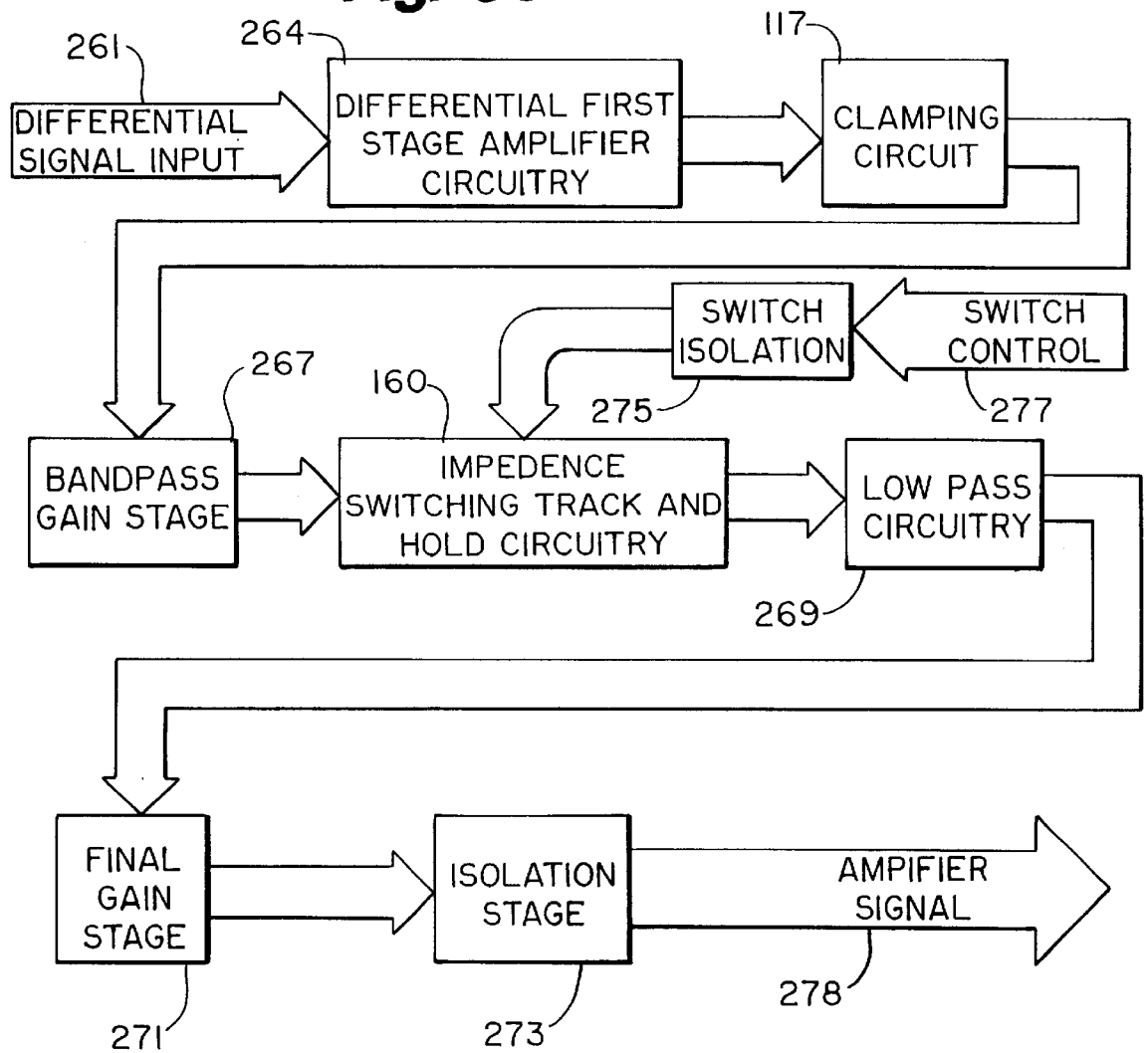
FIG. 39 is a flow chart/block diagram of the isolated fast recovery EKG amplifier.

An additional clamping circuit is also employed to aid in the reduced recovery time during stimulation. As can be seen in FIG. 39, an electronic track and hold switch 160 is placed between two stages of the amplifier. Track and hold switch 160 remains closed during stimulation, and in a preferred embodiment, a blanking period following stimulation. FIG. 39 is a block diagram/flow chart of the operation of the isolated fast-recovery EKG amplifier. Differential input signal 261 enters the Differential First Stage Amplifier Circuitry 264. Thereafter, it is controlled by Clamping Circuit 117. The signal is thereafter controlled by Clamping Circuit 117. The signal is then conditioned by Bandpass Gain Stage 267 and is regulated by Impedance Switching Track and Hold Circuitry 160. As depicted in FIG. 39, Switch Control 277 and Switch Isolation circuitry 275 control the timing of the signal. At the appropriate time, signals pass to Low Pass circuitry 269 and then to Final Gain Stage 271 and Isolation Stage 273. Finally, the amplified signal leaves the fast-recovery EKG amplifier as Amplified Signal 278.

Figure 40:
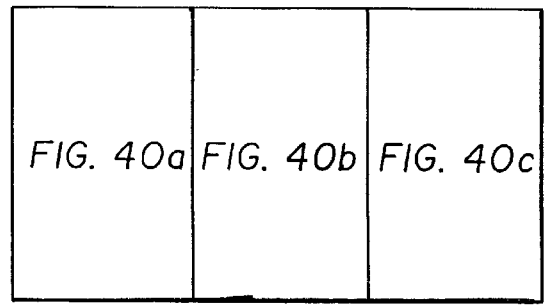
FIGS. 40 and 40a–c is a schematic of the fast-recovery EKG amplifier.
Figure 40A:
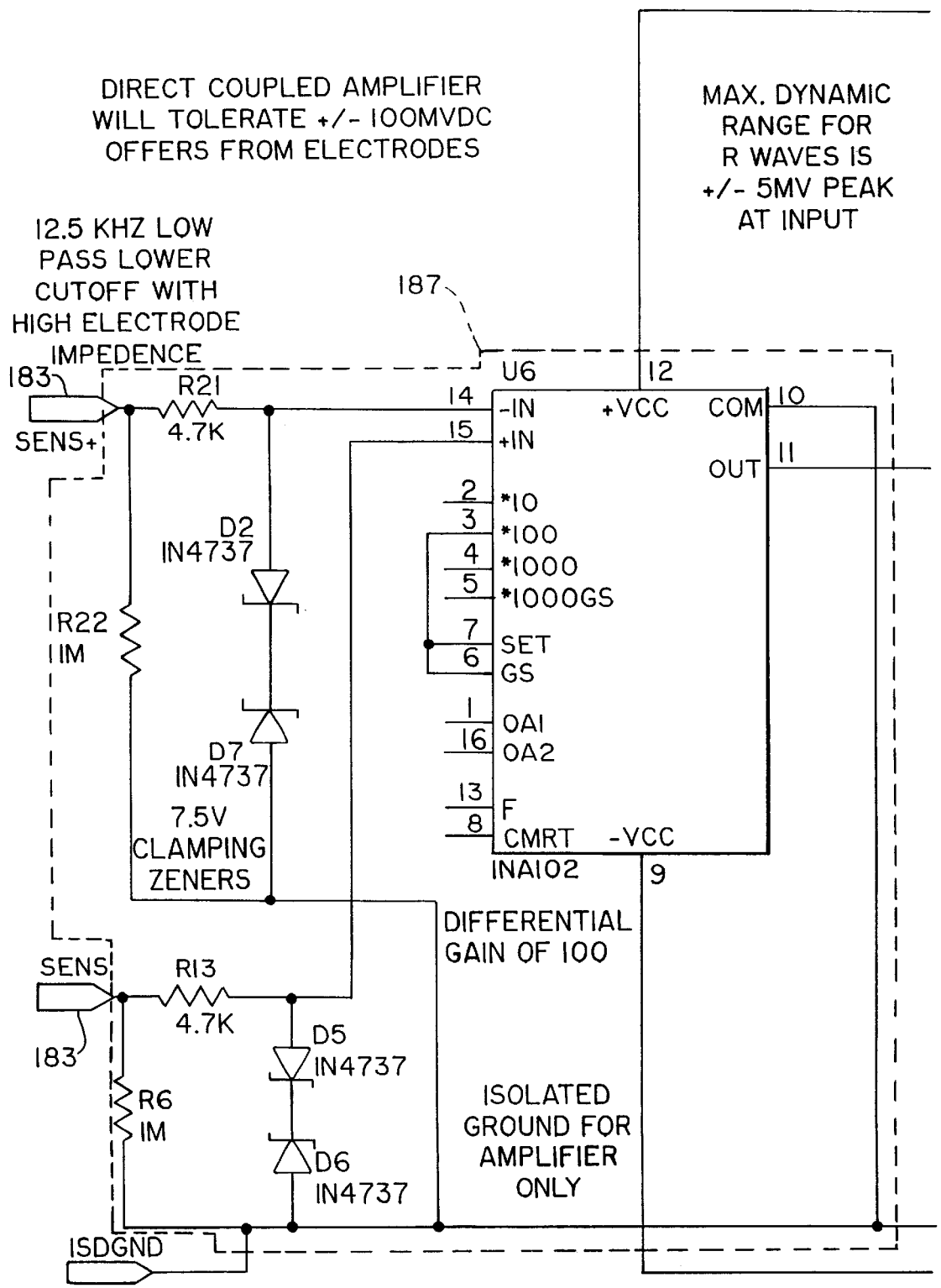
Figure 40B:
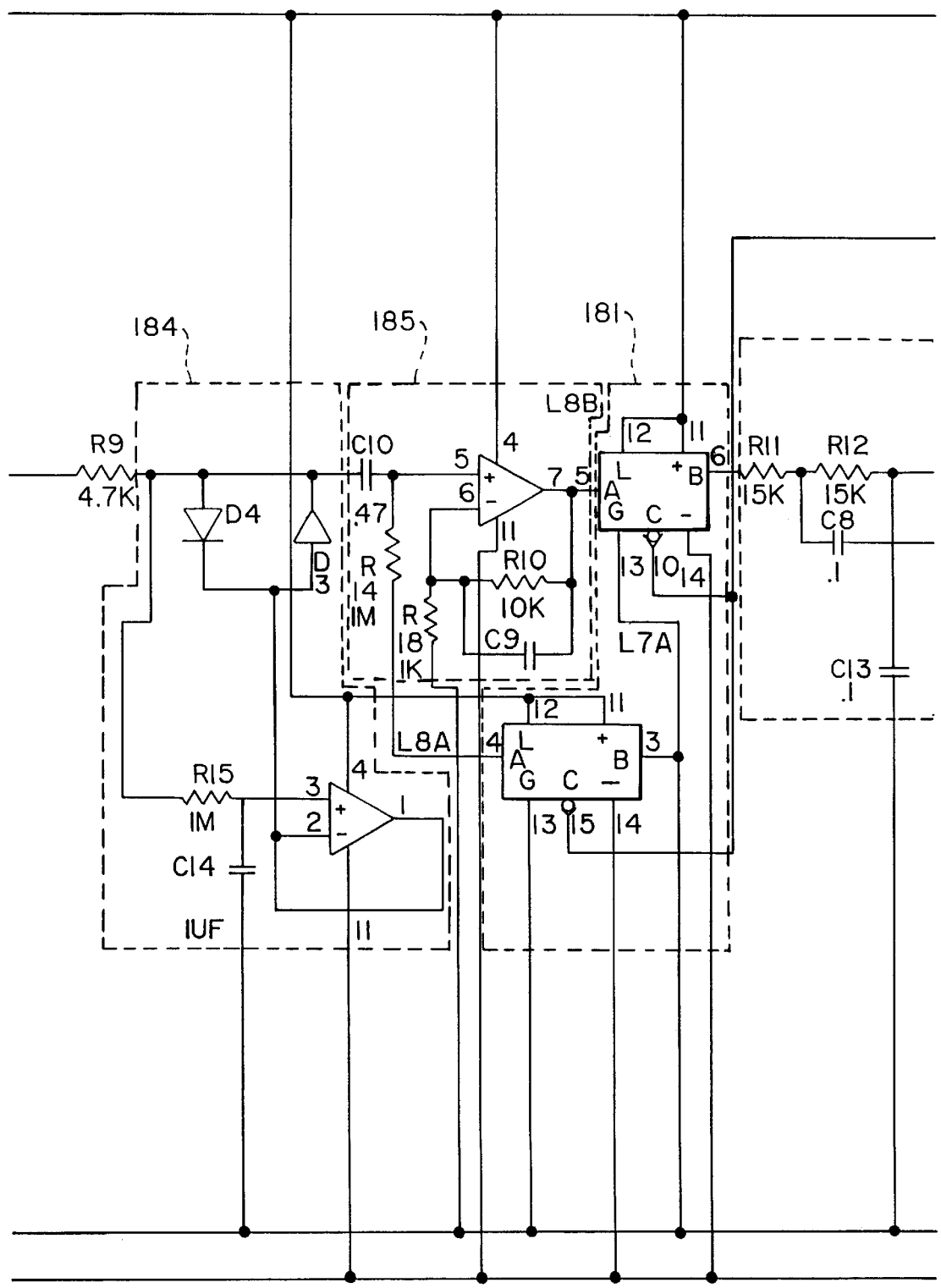
Figure 40C:
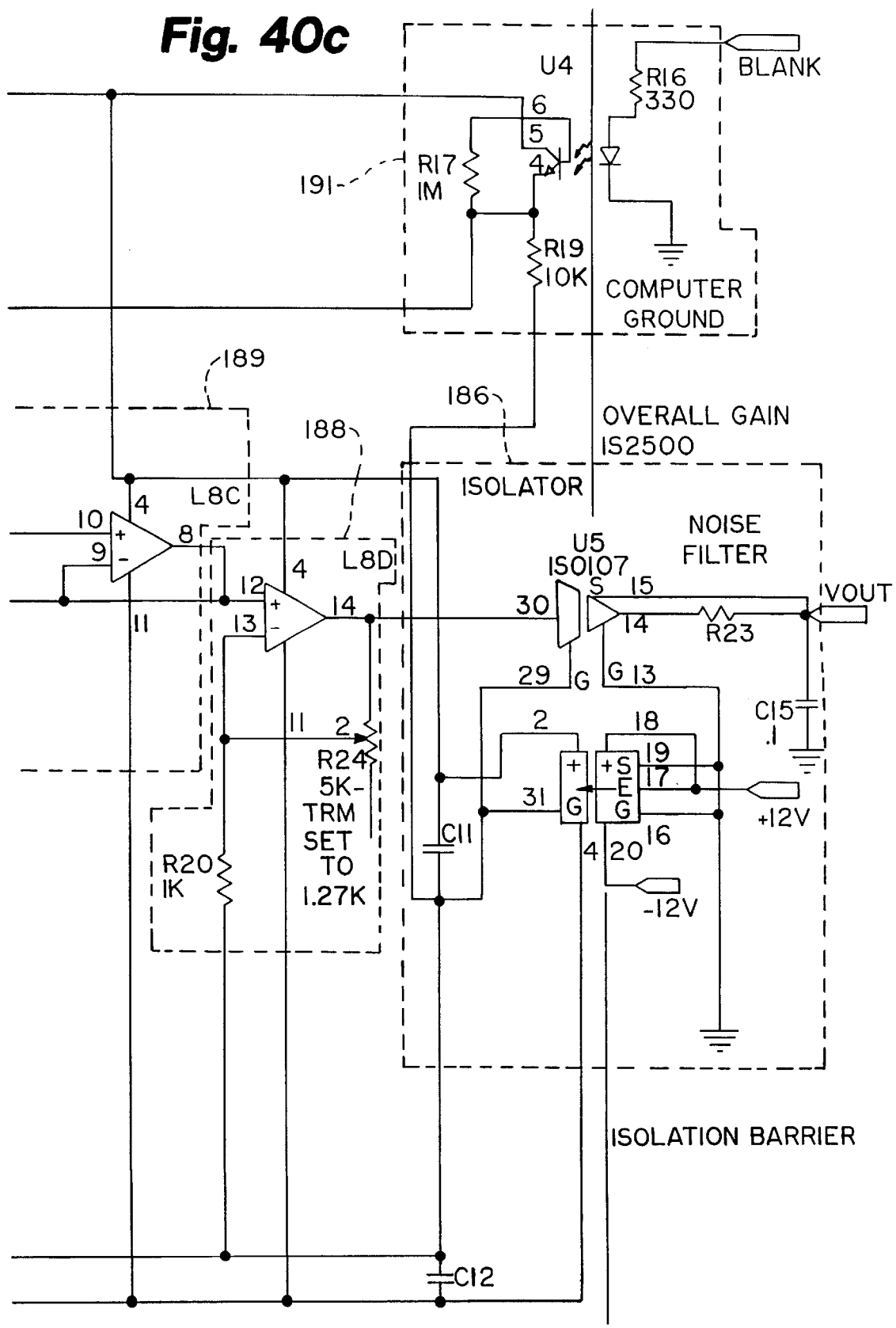

FIG. 40 is a schematic of the fast-recovery EKG amplifier. FIG. 40 depicts the circuitry implementing the flow chart of FIG. 39. As can be seen, differential inputs 183 connect to the differential first-stage amplifier circuitry 187. The next stage is clamping circuitry 184, which is in electrical communication with the bandpass gain stage 185. Next are the switch-and-hold circuitry 181, low-pass filter stage 189, and final gain stage 188. Isolated circuitry 186 and switching circuitry 181 are also depicted in FIG. 40.

Figure 32:
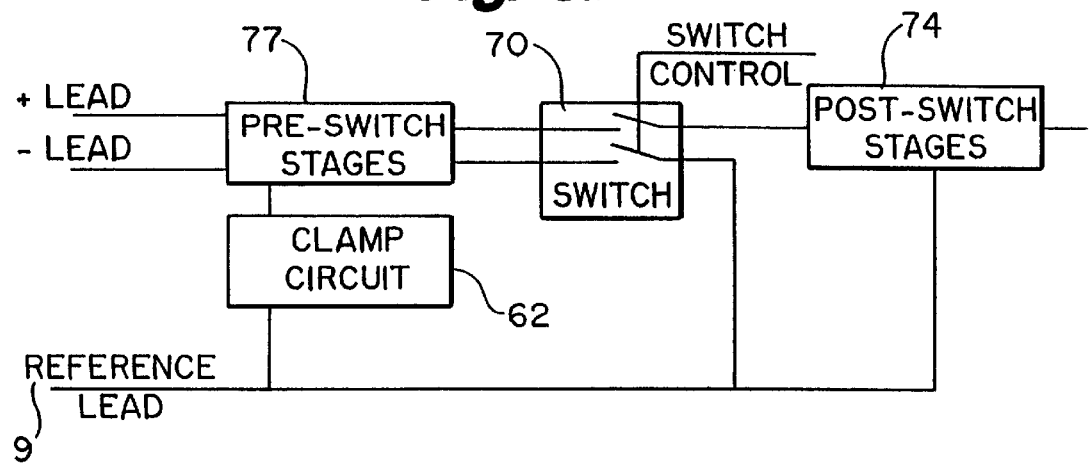
FIG. 32 is a block diagram of switching and planting circuit of the electronic interface.

FIG. 32 is a block diagram of the switching circuit. A clamping circuit is also added within the preswitch stages. The clamping circuit is designed to engage when the input signal is greater than about plus or minus 5 mV. When switch 70 is closed, the circuit behaves as a typical amplifier, using the reference lead as a body surface reference point for amplification of the differential signal between the positive and negative leads. Advantageously, this reference point is utilized during periods of blanking of the input signals. The clamping circuit remains inactive for input signals of plus or minus 5 mV. This allows amplification of normal skin surface ECG signals. During stimulation, the switch electronically disengages the amplification stages from each other. While open, switch 70 itself provides a hold function that holds constant the signal level for all postswitch stages 74. Switch 70 also decouples the reference signal from the preswitch stage 77. This decoupling advantageously prevents the preswitch stage from accepting any transient energy present during stimulation. In addition to switch 70 clamping circuit 62 engages when the input signal of greater than plus or minus 5 mV occurs. This clamping circuit 62 uses reference lead 9 to measure a baseline. A baseline shift is caused by the remnant charge left in the patient's body following the stimulation, shunting and modeling cycles performed by a preferred embodiment of the invention. This remnant charge equalizes over time at an exponential rate referred to as baseline decay. Compensation for baseline effects can be done by subtracting a non-stimulated waveform from a stimulated wave form. Further, a baseline shift with a time constant decay may also be utilized. The decay rate may be modeled by sampling the decay rate over a predetermined interval, for example, about 10 ms. The decaying baseline shift can then be mathematically removed from the acquired data. Advantageously, the decaying baseline shift may be removed for predetermined intervals, for example, intervals up to about 300 ms. Baseline noise can advantageously be reduced by filtering and statistical noise reduction by this invention, Whenever the input signal deviates from this baseline by more than 5 mV, the internal amplification stage is held at that level. This further reduces the effect of transient voltages generated during stimulation. These two features work together to keep the amplifier stages as close as possible to their prestimulation values, advantageously providing a very fast recovery time. An additional circuit in postswitch stage 74 provides a filter that eliminates any possible high-frequency, switch-related artifact that may occur. This is required because of the nature of the switch employed. This recovery technique is incorporated within the amplifier in one preferred embodiment of this invention.

Figure 41:
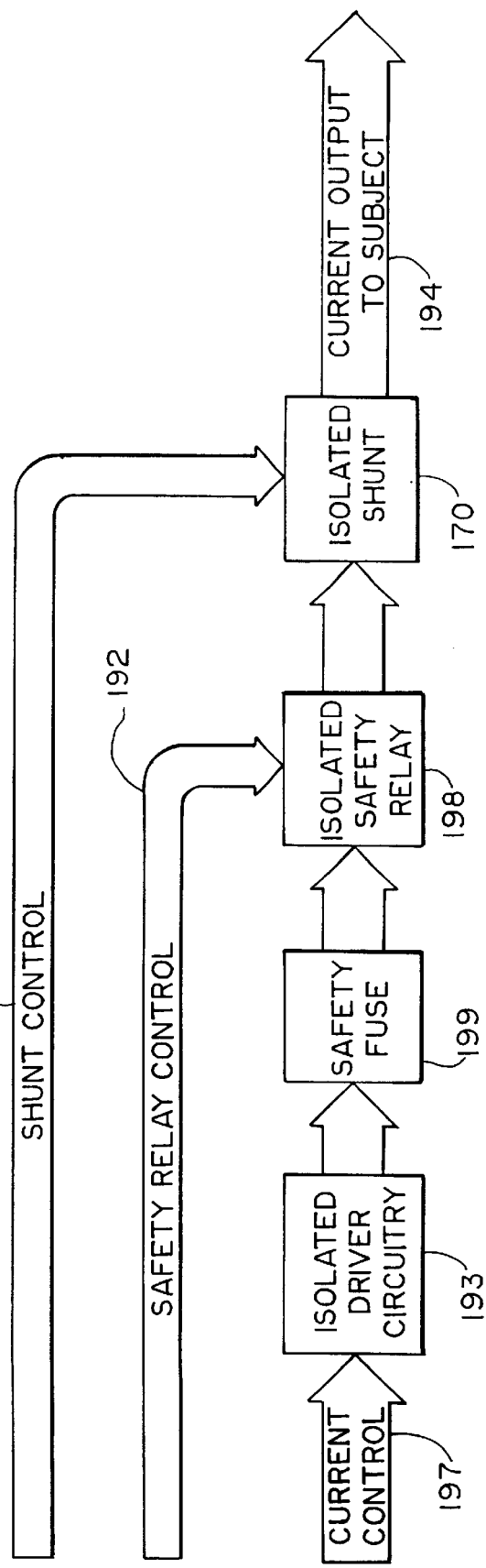
FIG. 41 is a block diagram/flow chart of the isolated driver section of the electronics interface.

FIG. 41 is a flow chart/block diagram of the isolated driver section of the subject invention. This is additional circuitry located within electronic interface 18. This driver section depicted in FIG. 41 has the characteristics to shape the energy delivery pulse to reduce rise-and-fall slopes, thereby reducing induced artifact signals. Further, the isolated driver depicted in FIG. 41 provides for shunting of any charges built up as a result of energy delivery. Shunting means may include switching from a high-impedance path to a low-impedance path for a short period of time to dissipate unwanted voltage that is present. The switching between high and low impedances is designed to occur within a time of less than 1 ms. Typically, high impedance is greater than about 5,000 Ohms, and low impedance is less than about 500 Ohms. This shunting means can be connected between more than one energy delivery lead. Further, the driver employs a constant current circuit thereby allowing control over energy delivery and varying lead or physiological impedances. As can be seen from FIG. 41, the Current Control 197 communicates with Isolated Driver Circuitry 193. Advantageously, there is also safety circuitry, which includes Safety Fuse 199 and Isolated Safety Relay 198, controlled by Safety Relay Control 192. Shunt Control 196 then controls the Isolated Shunt Circuitry 170, which timely delivers the subpacing current output 194 to the subject.

Figure 42:
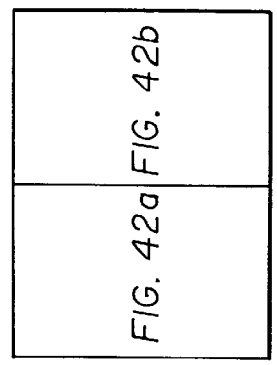
FIGS. 42 and 42a–b is a schematic of the isolated driver section of the electronics interface.
Figure 42A:
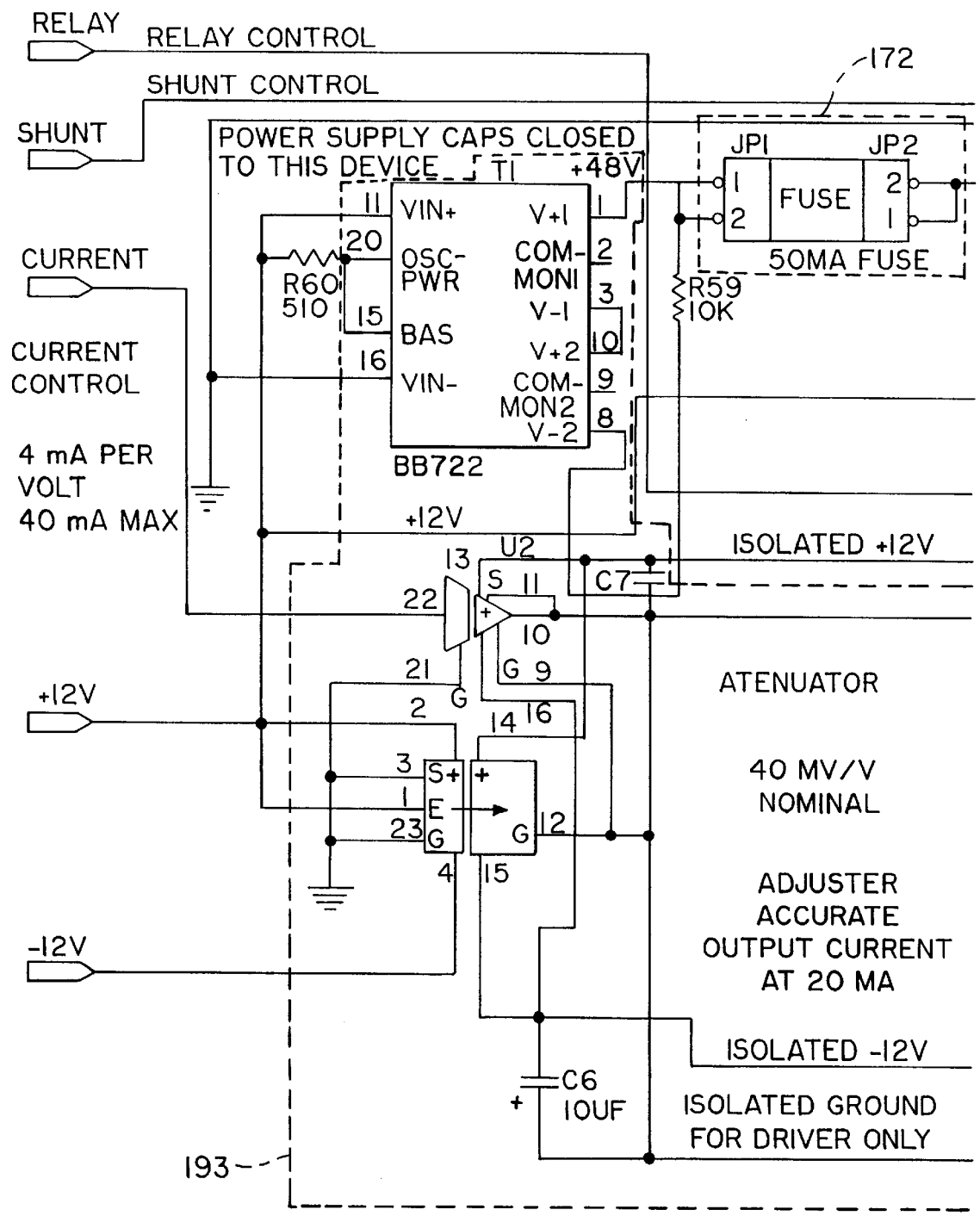
Figure 42B:
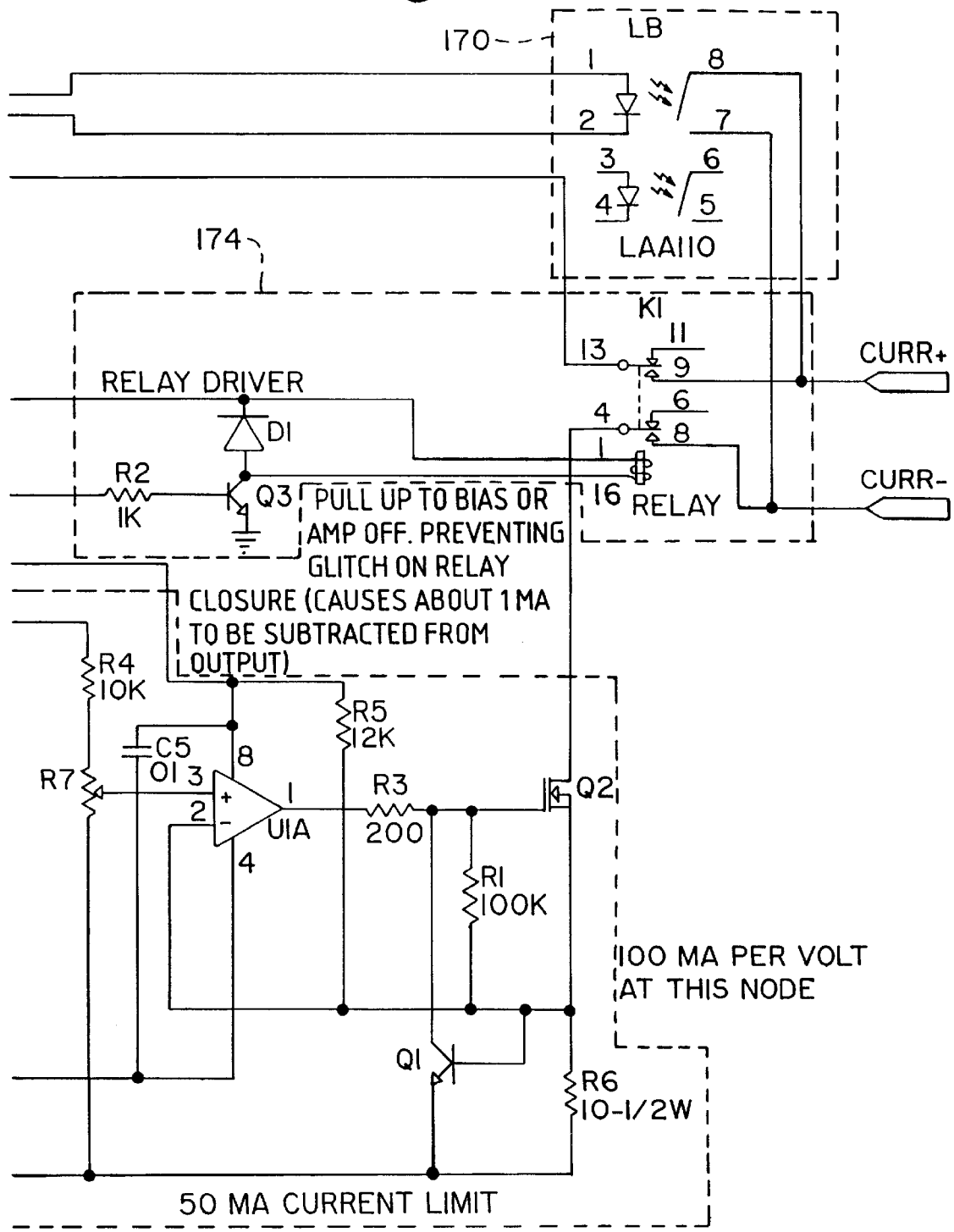

FIG. 42 is a schematic level of an exemplary isolated driver section. Blocked off on the schematic are Isolated Driver section 193, Safety Fuse 172, safety switch 174, and shunting circuitry 170.

Additional techniques and means for improving sensing and analysis of cardiac signals will now be discussed, including both stimulated as well as non-stimulated signals. Such techniques and means include: wavelet decomposition, alternative or passive shunting, detection of ECG alternans, stimulation of alternans behavior, detection of differences between natural and stimulation induced alternans behavior, cardiomyopathy detection techniques, body surface shunting synchronous with the R-Wave on Signal Averaged Electrocardiogram, subthreshold stimulation without capture to reduce the stimulation threshold causing changes to the action potential of a subsequent suprathreshold stimulation with capture, Wedensky transthoracic stimulation, Wedensky phenomenon within the late potential region, wavelet analysis of subthreshold stimulated and control Signal Averaged Electrocardiograms in healthy subjects and ventricular tachycardia patients, QRS complex alternans detected by wavelet decomposition of Signal Averaged Electrocardiograms, and QRS background noise differentiation. Each such means will now be discussed, including reference to FIGS. 47–57.

Wavelet Decomposition is a mathematical analysis allowing the study of a particular signal of interest in the presence of other signals. The analysis allows itself to be tuned towards higher sensitivity to one or more particular type(s) of waveforms while reducing sensitivity towards another. This type of analysis is particularly useful when used on ECG data. ECG data can contain specific environmentally present electrical noise, for example 50 Hz or 60 Hz. ECG data may also contain broadband constant or intermittent noise produced by local sources of electromagnetic interference. The dynamics of the ECG waveform itself (as it is produced by the heart) can be defined in both frequency and amplitude. Research has defined such an analyzing waveform for use with Wavelet Decomposition in studying ECG data. This application includes the use of such wavelet decomposition to analyze either the natural ECG or stimulated ECG data produced by an ECG device, including the devices disclosed herein. Also included is the use of wavelet decomposition to analyze combinations of natural ECG or stimulated ECG data produced by an ECG device including the devices disclosed herein.

This application discloses, inter alia, the methods and apparatus of using the stimulation electrodes (or any large area surface electrodes) in an ECG device, including the devices disclosed herein, as a method of enhancing sensing of cardiac condition. First, these electrodes can act as a shielding mechanism to enhance the sensing of ECG signal. The presence of a large area electrode acts as an electrical shield allowing better sensing of cardiac signal. The use of such an electrode is identified and claimed here.

Embodiments of the present invention also include an optimum electrode configuration to induce non-invasive Wedensky phenomenon in organisms. Wedensky phenomenon is the effect of subthreshold stimulation on the subsequent suprathreshold excitation. Recently, it has been shown that external transthoracic subthreshold stimulation synchronous with the R wave produces Wedensky phenomenon which differs in normal subjects and ventricular tachycardia patients. To produce non-invasive Wedensky phenomenon optimally, sufficient myocardial current density (MCD) has to be combined with minimum MCD variance. A computer model of transthoracic currents was used to study the effects of different electrode systems on mean MCD and its variance. Three 2D horizontal thorax cross-sections were considered with high middle, and lower sections of ventricular myocardium. Tissue characteristics were taken from an anatomical atlas and represented by conductivities within a rectangular grid of 460×700 nodes. Finite difference model of current flow investigated 30 different frontal electrodes used in 13 different positions against 5 different positions of a dorsal patch (1950 experiments with each cross-section). The current densities within the modeled myocardium of all three cross-sections were considered together (79956 nodes) and for each experiment, the mean MCD and its standard deviation were computed. Independent of the position, there is a positive relationship between the area of the frontal electrode with mean MCD (3.78, 4.29, 4.68, 4.98, 5.18 5.32, 5.39 (in technical units) for linearly increasing length of the frontal electrode of simulated sizes from 15 to 120 mm) while the coefficient of variance of MCD decreases with the increasing area of the frontal electrode (0.52, 0.49, 0.46, 0.43, 0.41, 0.38, 0.36). The coefficient of variance of MCD was further improved when introducing perforations into the largest size electrodes. However, this improvement was only marginal (lowest coefficient of variance of 0.31 and 0.29 was achieved with un-perforated and perforated electrode. respectively −7% reduction). Embodiments of the present invention provide that noninvasive induction of Wedensky phenomenon involves a large precordial electrode. Furthermore, embodiments of the present invention demonstrate that the variance of myocardial current density is slightly reduced by using perforated electrodes. These embodiments will be further described later in this disclosure.

Shunting is a technique of dissipating unwanted voltage. Use of the devices and methods disclosed herein involve the delivery, of energy followed by the shunting of the stimulation leads as a means of reducing the artifact caused by charge remaining on the lead system. This shunting process also has application when no energy is delivered through the leads, and is interchangeably referred to herein as alternative or passive shunting.

By passively changing (shunting) the potential of a large area of the body, an impedance modulation in the body can be realized. The generation of the surface ECG from the heart involves the current flow from cell to cell as depolarization recruitment progresses. This current vector multiplied times the local resistivity gives the local electrical field. The components of that on the skin are what is called the ECG. By pulsing the shunt across the chest it is possible to modulate that resistance (i.e. "impedance modulation"). This is similar to changing the angle of view of the cardiac signal. This altered measurement can also be compared against the non-shifted measurement.

Also disclosed here is the process of shunting these or any larger area surface electrodes together to effectively provide an isopotential at the skin surface. This action can be viewed as "passive stimulation." It can shift the body potentials and possibly alter conduction pathways to allow better sensing of the cardiac condition. This altered measurement can also be compared against the non-shifted measurement. The use of either "impedance modulation" or "passive stimulation" and its effect on the QRS signal is thus disclosed herein.

Alternan behavior consists of the changing of cardiac signal in a modal fashion. That is, one beat will have certain characteristics, the next will have different characteristics, and the following will have characteristics like the first. The process of averaging together alternate beats used in an ECG device, including the devices disclosed herein, allows the measurement of the natural ECG alternan behavior. The extent and change of this measurement can be a measure of cardiac condition. The use of this measurement as an indication of cardiac condition is disclosed and included in this application.

By averaging together alternate beats, the systems and methods disclosed herein allows the measurement of alternan behavior. This method can be useful in the determination of cardiac condition. Thus, this application discloses use of the systems and methods to achieve stimulation-related changes in alternan behavior, or shunting/impedance shifting-related changes (passive stimulation in alternan behavior as a method for detecting cardiac condition). Furthermore, the differences between natural alternan behavior and stimulated alternan behavior can also be useful in determining cardiac condition. This application discloses and includes the use of the differences between these behaviors as an indicator of cardiac condition.

A further use of the devices and methods disclosed herein is to assess conduction pathway changes within the heart by examining the changes in ECG while stimulating and not stimulating the myocardium. Another use disclosed herein is to detect non-conduction related abnormalities of the heart including, but not limited to, cardiomyopathy the changes invoked by the process of stimulating, shunting, or examining alternate beats could also be used to determine the extent of physical myocardial abnormality. Stimulation related changes shunting and impedance shifting related changes (passive stimulation), or changes due to average of alternate beats as a method of detecting non-conduction related abnormalities are disclosed and included herein, Applicants have further discovered improved means for signal analysis by analyzing the effect of body surface shunting synchronous with the R-wave on Signal Averaged Electrocardiograms by comparing the differences between normal subjects and patients with ventricular tachycardia. This study investigated the effects of creating a body surface short circuit synchronous with the R-wave on the spectral profile of signal averaged electrocardiograms.

In 35 patients with EP inducible ventricular tachycardia and in 30 healthy volunteers, 60 to 200 QRS complexes were digitally recorded: using orthogonal leads. Synchronous with on-line R-wave detection, two surface patches corresponding to the orthogonal Z lead (a precordial patch and a left dorsal subscapular patch) were electrically connected with negligible impedance for 2 ms. The QRS complexes recorded in this way were averaged and compared with the same number of averaged QRS complexes recorded without surface shunting. Both high-gain signals were decomposed with 53 scales of Morlet wavelets of central frequencies 40 to 250 Hz and vector magnitudes of wavelet decompositions were constructed. The differences between these decompositions were characterized by their surface areas in windows of 0 to 10 ms, 10 to 20 ms, and 20 to 30 ms, etc., after surface shunting.

Figure 47:
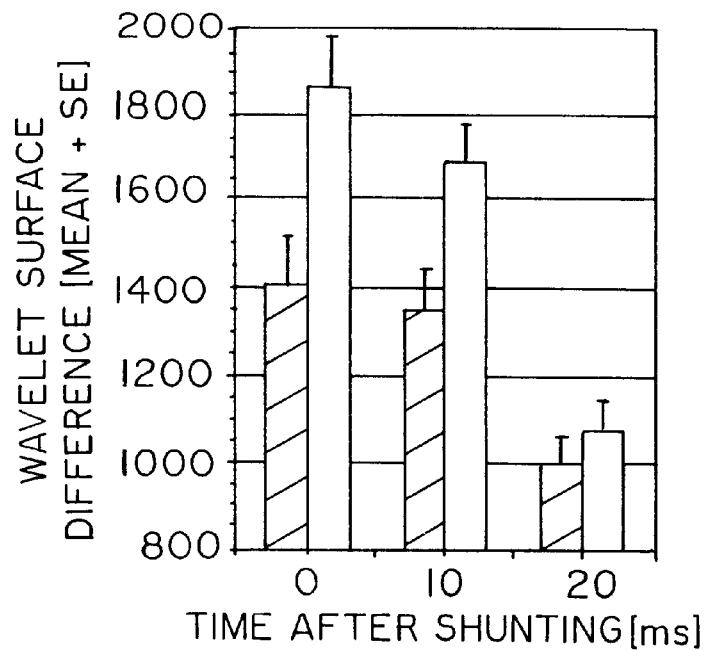
FIG. 47 is a data set of observed data.

The area difference was substantially greater in healthy volunteers, as shown by the light bars in FIG. 47, than in VT patients (dark bars) both immediately, i.e. 0–10 ms after surface shunting ($p<0.04$) and 10 ms later ($p<0.03$) but not later ($p=0.4$ at 20 ms later, and $p=0.5$ at 30 ms later). From this research data it may be concluded that short circuiting the body surface produces both recording artifact and physiological stimulus affecting the depolarization sequence. This stimulus is very short lived and is more marked in healthy hearts than in VT patients who are probably less susceptible to minor electrical provocations.

Applicants further compared high-gain electrocardiographic evidence of Wedensky Phenomenon in healthy subjects and ventricular tachycardia patients. Of course it is known that Wedensky Phenomenon is the effect of a subthreshold stimulation without capture that reduces the stimulation threshold and changes the action potential of a subsequent suprathreshold stimulation with capture.

To investigate whether this phenomenon can be documented after transthoracic subthreshold stimulation (2 ms. pulse of 5 to 40 MA between surface precordial and subscapular patches delivered synchronous with R-wave detection), 60 to 200 subthreshold stimulated QRS complexes were signal averaged and compared with the same number of average non-stimulated complexes recorded during the same experimental session. The electrocardiographic recordings were obtained with standard orthogonal leads. In order to detect even minor changes within the QRS complex, each lead of both stimulated and control averaged complexes were wavelet decomposed (53 scales of the Morlet wavelet with central frequencies of 40 to 250 Hz). The wavelet residuum corresponding to the Wedensky Phenomenon was obtained by subtracting the vector magnitude wavelet decomposition of the control QRS from the vector magnitude decomposition of the subthreshold stimulated QRS. The surface of the residuum was investigated in windows of 1 to 25 ms following the stimulation. The test was performed in 35 patients with EP inducible ventricular tachycardia and in 30 healthy controls.

Figure 48:
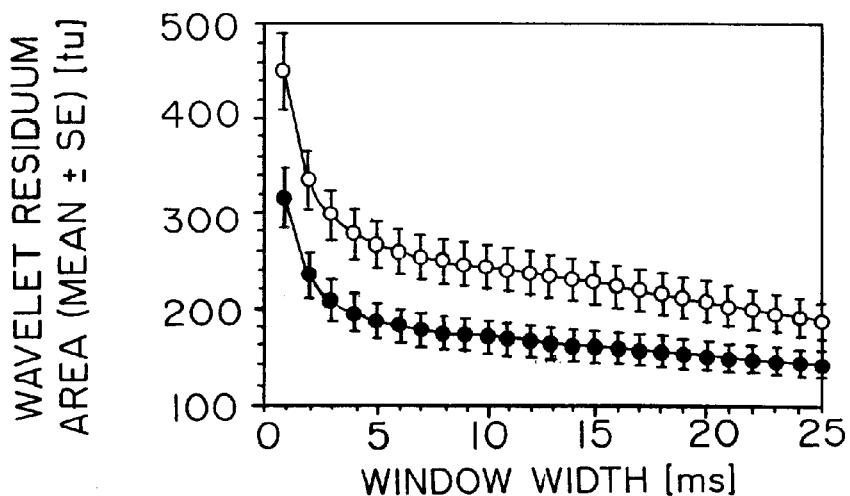
FIG. 48 is a data set of observed data.

The wavelet residuum showed sharp increase in the spectral power of the stimulated complex that was significantly more marked in healthy volunteers ($p<0.01$) than in VT patients. This is shown in FIG. 48 in which there is 20 ms stimulation, and in which full circles are VT patients, and empty circles are control patients. This shows that Wedensky phenomenon induced by an external transthoracic subthreshold stimulation can be documented in man and differentiates-VT patients from controls.

In further investigation, patients with electrophysiologic documented ventricular tachycardia (n=35) and healthy controls (n=30) were subjected to a subthreshold external stimulation between precordial and left subscapular patches. Stimuli of 5, 10, 20, and 40 ma were delivered for 2 ms synchronous with R-wave detection. 60 to 200 subthreshold stimulated QRS complexes were averaged and compared with the same number of non-stimulated complexes. Vector magnitude Wavelet decompositions (53 scales of central frequencies 40 to 250 Hz) were obtained for both stimulated and non-stimulated complexes and their difference characterized the Wedensky Phenomenon numerically. The surface area of the 3D envelope of the wavelet residuum was measured in a window ±5 ms from the R peak (stimulation moment) and in surrounding 10 ms windows.

Figure 49:
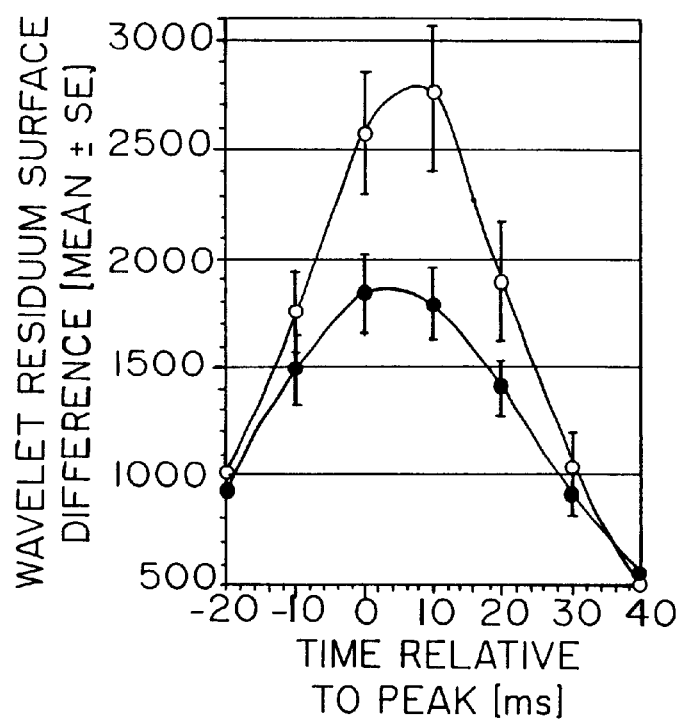
FIG. 49 is a data set of observed data.

The wavelet residuum showed a sharp increase of the surface of the 3D spectral envelope at and after the stimulation that was more marked in healthy volunteers than in VT patients, as shown in FIG. 49 in which 40 ma experiments were conducted, and full circles are VT patients, and open circles are control patients. The maximum changes in wavelet residuum increased with stimulation subthreshold energy: 5 ma: control 1993±181 technical units, VT patients 1488±159; 10 ma: control 2151±200. VT patients 1543±154. 40 ma: control 2746±332, VT patients 1842±177, i.e. all were statistically significant. Thus, externally induced Wedensky phenomenon shows a dose response that is more marked in healthy volunteers than in VT patients.

Wedensky Phenomenon within the late potential region was analyzed utilizing dose-related separation of patients with ventricular tachycardia from healthy controls. Patients with EP documented ventricular tachycardia (n=35) and healthy controls (n=30) were subjected to a subthreshold external stimulation between precordial and left subscapular patches. Stimuli of 5, 10, 20, and 40 ma were delivered by 2 ms after a 20 ms delay following a real-time R-wave detection. 60 to 200 subthreshold stimulated QRS complexes were averaged and compared with the same number of non-stimulated complexes. Vector magnitude wavelet decompositions (53 scales of central frequencies 40 to 250 Hz were obtained for both stimulated and non-stimulated complexes and their difference characterized the Wedensky Phenomenon numerically. The surface area of the 3D envelope of the wavelet residuum was measured in a window 20±5 ms after the R peak (a window centered around the stimulation moment) and the subsequent 10 ms windows (30±5 ms after the R peak). The areas of the residuum spectral 3D envelope in these windows were statistically compared in the VT patients and healthy controls.

Figure 50:
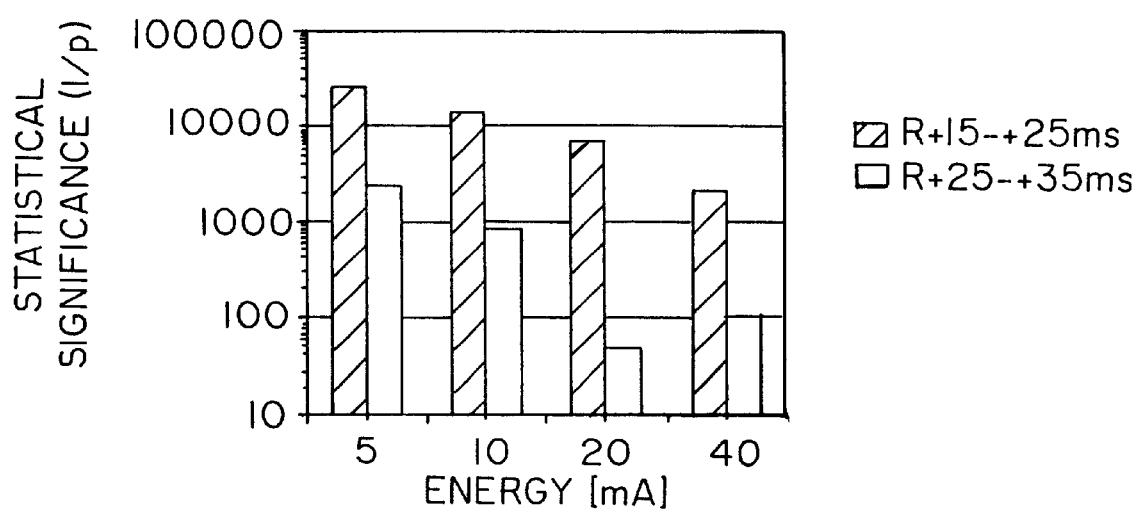
FIG. 50 is a data set of observed data.

All differences were highly statistically significant, as shown in FIG. 50 (up to $p<0.00005$), with the manifestation being more pronounced in the control group. The separation of the groups was more significant in the window around the stimulation moment that in the subsequent window and the significance decreased with increasing subthreshold stimulation energy. Accordingly, a Wedensky phenomenon in the late QRS part is brief, and VT patients are less sensitive to the phenomenon, especially at very low subthreshold energies.

In yet another assessment, patients with EP documented ventricular tachycardia (n=35) and healthy controls (n=30) were subjected to a subthreshold external stimulation between precordial and left subscapular patches. Stimuli of 5, 10, 20 and 40 ma were delivered for 2 ms either simultaneously with the R-wave or 20 ms after the R-wave. 60 to 200 subthreshold stimulated QRS complexes were averaged and compared with the same number of non-stimulated complexes (reference). Vector magnitude wavelet decompositions (53 scales of Morlet wavelet with central frequencies 40 to 250 Hz) were obtained for both stimulated and non-stimulated complexes. Local maxima of the 3D spectral envelopes were counted in 50 ms windows following the subthreshold stimulation and compared in VT patients and healthy controls.

Figure 51:
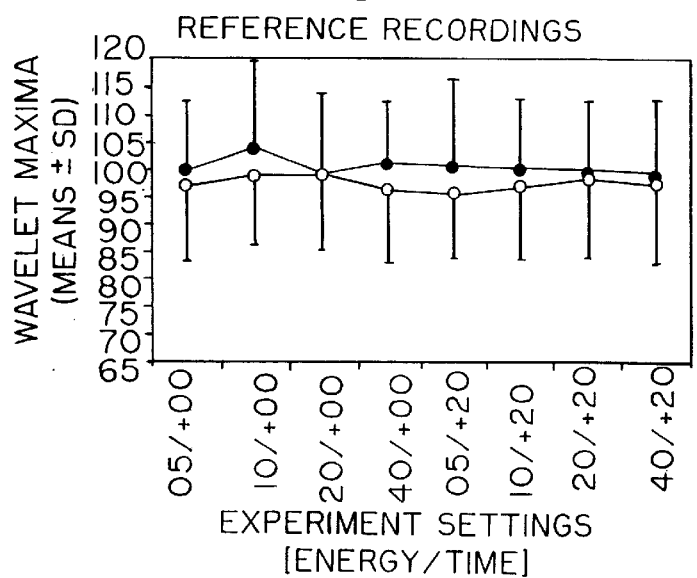
FIG. 51 is a data set of observed data.
Figure 52:
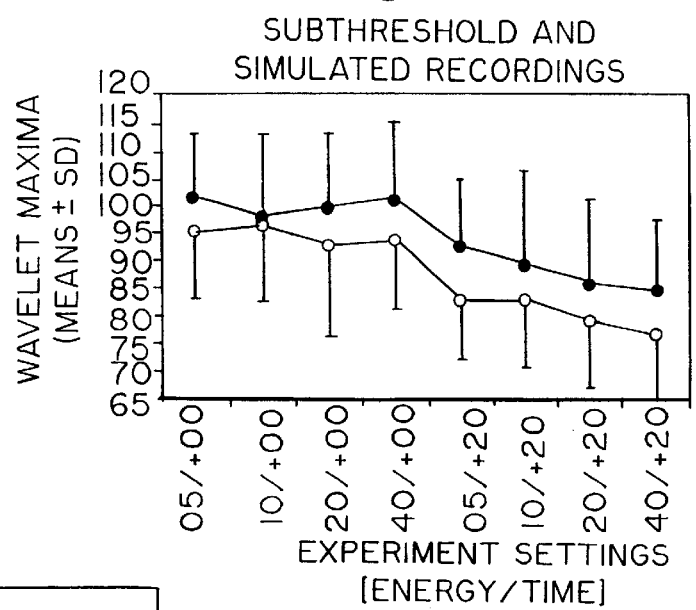
FIG. 52 is a data set of observed data.

In reference recordings, FIG. 51, there were no statistical differences between VT patients (shown as closed dots) and controls (open dots). In subthreshold stimulated recordings, the local maxima decreased (3D spectral envelopes became more smooth). This decrease was greater in healthy controls and with stimulation after the R wave FIG. 52, wherein all the differences except in experiment 10/00 were significant up to $p<0.001$. Accordingly, subthreshold external stimulation makes the depolarization wave more uniform, mainly when delivered in the terminal QRS part in healthy volunteers.

Although the electrical alternans of the ST segment and T-wave has been extensively researched the alternans of the QRS complex, has generally not been investigated-mainly because of difficulties in detecting it. Applicants innovations overcome such previous limitations, and allowed further assessment as follows.

In 35 patients with EP inducible ventricular tachycardia and in 30 healthy volunteers, 120 to 400 QRS complexes were digitally recorded using orthogonal leads. From these sequences of beats, the complexes with even and odd order numbers were separately aligned and averaged. The resulting high gain signals were processed with wavelet decomposition (53 scales of Morlet wavelets with central frequencies of 40 to 250 Hz) and the differences between the resulting 3D spectral envelopes were computed. These created altemans-related 3D spectral envelopes and were characterized by surface areas in subsequent 10 ms windows.

Figure 53:
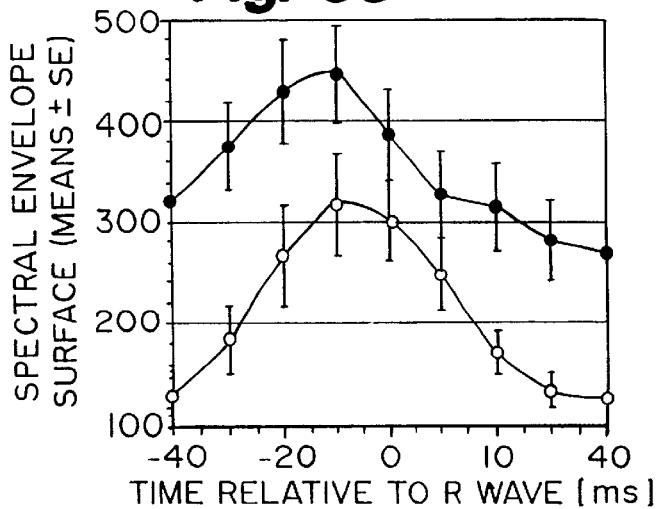
FIG. 53 is a data set of observed data.

The surfaces of the altemans-related 3D spectral envelopes were substantially larger, as shown in FIG. 53, in VT patients (full circles) compared to healthy controls (open circles). The differences between the groups were particularly marked within the initial and terminal portions of the QRS complex ($p<0.00005$ in the 10 ms window preceding the R wave by 40 ms). Thus, a wavelet decomposition of alternating signal averaged FCG is capable of detecting electrical alternans within the QRS complex, and the QRS complex alternans is significantly more expressed in VT patients compared to healthy controls. Also, the QRS complex altemans differs between VT patients and controls mainly at the beginning and at the end of the QRS complex.

Of the many improvements discussed above, it is worth noting that wavelet analysis is particularly significant. Indeed wavelet analysis is a highly reproducible method for SAECG processing which is as powerful as the time-domain analysis for the identification of ischemic VT patients. As compared to the time-domain analysis, wavelet analysis is not dependent on infarct site, and is able to distinguish post myocardial infarction patients without VT from healthy subjects. As compared to known applications of wavelet representations, Applicants utilized much finer distinctions of scales (7 vs. 54) with a different range of middle frequencies (70–200 Hz vs. 40–250 Hz). Applicants also determined that wavelet analysis of signal-averaged ECGs is superior to the standard time-domain analysis in predicting post myocardial infarction events. In particular this analysis identifies not only those post MI patients who are at risk of non-fatal sustained ventricular tachycardia, but also those who are at risk of sudden cardiac death. Thus, this is the first discovery of using wavelet analysis for categorical risk analysis with prospectively collected signal-averaged ECG data in an almost consecutive population of MI survivors. As such, a significant advantage of this technology is that compared with standard time-domain analysis, the wavelet decomposition of signal-averaged ECGs provides a more powerful distinction between survivors of an acute MI who are and are not at high risk of further complications. FIG. 54 shows sample data of the interdependence of time-domain and wavelet decomposition indices, in which is presented the correlation coefficient between the two techniques. The value of correlation coefficient is shown above the diagonal, and the corresponding p-values are displayed below. FIG. 55 is data representing a comparison of signal-averaged ECG indices in patients with and without follow-up events. For each category of follow-up events and for each time-domain and wavelet decomposition parameters, the table lists the averaged value in patients with and without the event. The last column ($p=$) shows the significance of statistical comparison of values in patients with and without events (nonparametric Mann-Whitney test). FIG. 56 shows the association of positive SAECG findings with: follow-up events. For each category of two year follow-up events and for each of four diagnostic criteria, the table shows the number of true positive (tp) and true negative (tn) patients as well as the statistical significance ($p-$) of the association of events with findings of a positive signal averaged ECG analysis (Fishers exact test). Herein, CM represents cardiac mortality, PAD represents potentially arrhythmic death, SCD represents sudden cardiac death, VT represents sustained ventricular tachycardia, PAE represents potentially arrhythmic events, and ARF represents sudden cardiac death and/or ventricular fibrillation. FIG. 57 is a comparison of positive predictive accuracy of predicting follow-up events. In this Figure, for each category of follow-up events and for six selected levels of sensitivity (Sen) the table shows maximum positive predictive accuracy (PPA) achieved at that level of sensitivity with timedomain indices (TD) and wavelet decomposition indices (WD) of signal averaged ECGs. The table also shows the numbers of patients for which the diagnostic criteria of both techniques adjusted for the given level of sensitivity did not agree (Discordance) divided into the number of those for which the time-domain diagnosis was correct (TD+) and those for which the wavelet decomposition diagnosis (WD+). The last column shows the statistical significance ($p=$) of the comparison of values of TD+ and WD+ (sign test).

One additional signal improvement technique involves improved noise management in the QRS realm. When sensing signals from electrodes, a certain amount of environmental background noise is unavoidable. This noise may vary in frequency and direction, causing certain electrode placements to be more sensitive to receiving it than others. The following software-based approach addresses an implementation to reduce sensitivity to this background environmental noise during the processing of data recorded from electrodes.

When sensing signals from electrodes, a certain amount of environmental background noise is unavoidable. This noise can vary in frequency and direction causing certain electrode placements to be more sensitive to receiving it than others. To improve alignment of QRS complexes of multiple channel ECG data (XYZ, multi-lead intercardiac, 2 lead, etc.,) a mechanism which reduces sensitivity to background noise may be applied. The mechanism involves the determination of the signal level of the background noise and the signal level of the desirable:signal (in the case of ECG data, the QRS). These parameters are determined for each data channel. The parameters are combined into ratios of Desirable/Background signals (hereby called D/B ratio). Channels with low D/B ratios are excluded from use during QRS alignment. Since it is possible for background noise to vary over time, an alternate implementation of this mechanism could be to assess the signal around each QRS complex for D/B ratio and exclude QRS's based on their individual ratios.

One embodiment of software source code to implement the above wavelet processing for SAECG data may include one or more of the following functionality features:

a. the software shall accept two orthogonal XYZ SAECG signals for analysis along with any parameters required to perform the remaining analysis;

b. the software shall process the region of interest of the two signals into individual wavelet surfaces using the Morlet wavelet;

c. the software shall mathematically combine the two wavelet surfaces to form a wavelet residuum;

d. the software shall calculate the'surface area for the region of interest within the wavelet residuum;

e. the software shall return the surface area calculation along with any other pertinent results of the calculation; and f. the software shall calculate the count of local maxima of the two wavelet surfaces in the region of interest and return these counts.

Figure 58:
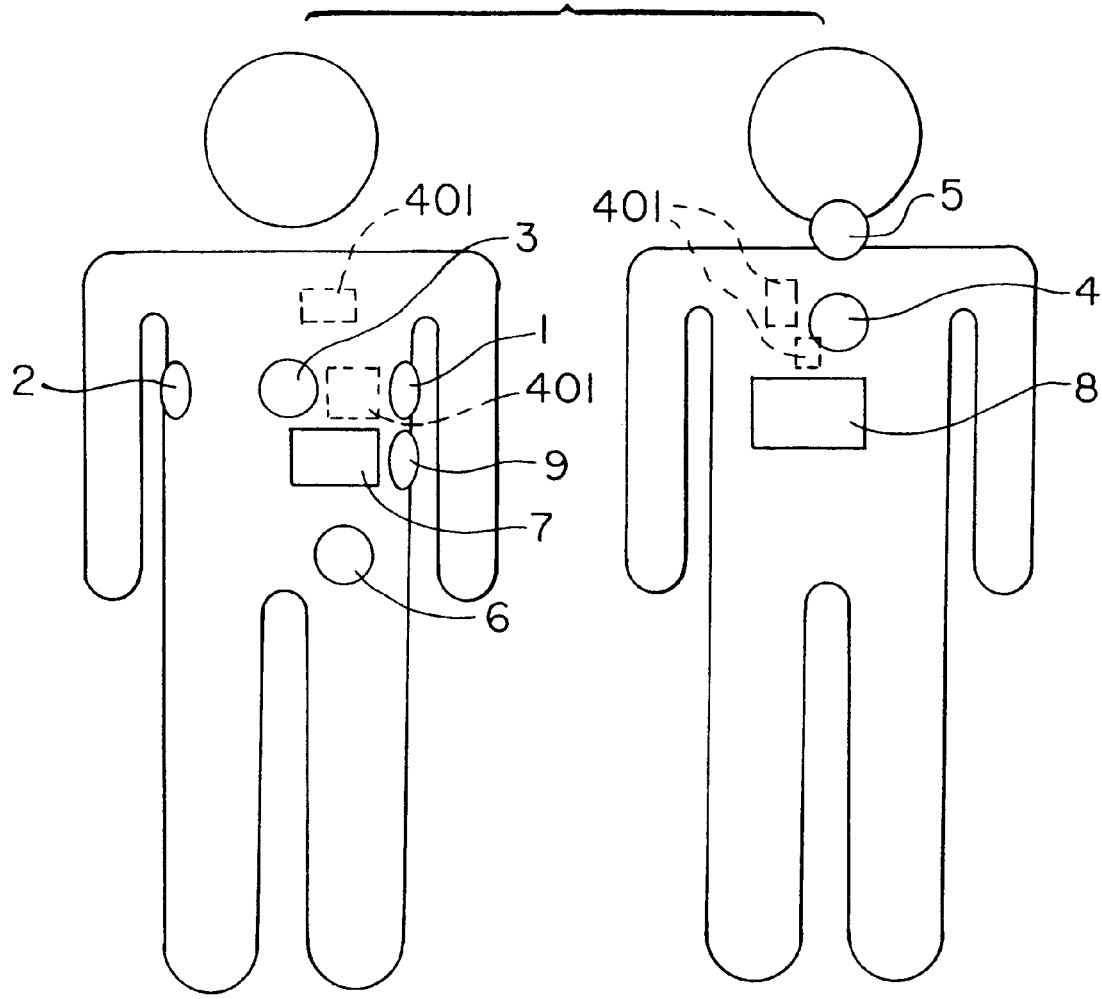
FIG. 58 is an exemplary depiction of a patient showing possible electrode patient locations combined with elements of existing ambulatory and/or implantable technology.

Although many of the above embodiments have been described in the context of a system and method having non-invasive elements only, it is not necessarily a limitation of this invention. Indeed, in other embodiments it-is preferred to combine the above technically advantageous stimulation features and controls with elements of existing ambulatory and/or implantable technology. For example, one embodiment is shown schematically in FIG. 58 in which select portions of electronic interface 18 , computer 27, monitor 23, and lead system 12 may be incorporated into an external ambulatory or implantable module 401. As shown, module 401, or sub-components of module 401, may be positioned as a permanent or temporary component within or on the body of the patient 35. One embodiment locates module 401 as a pectoral region implant while another embodiment comprises locating the module as an abdominal region implant. It is of course possible to locate such implant(s) or in on other sites of the body, as appropriate.

Accordingly, it is possible to combine the sensing means of the above described invention as a component and feature of an implantable pacemaker, defibrillator, cardioverter, or similar device. Other elements may also be combined as an implanted component or feature, such as, for example, fast recovery means, timing or synchronization means, processing means, or other features shown in the embodiments of FIGS. 1–46 as external of the patient's body. In this manner, the system and method allows for an external or internal stimulation using the unique stimulation techniques disclosed herein along with implanted signal sensing and processing means. This combination provides for greatly expanded features having considerable value to patients and medical providers by allowing virtual on-demand in-situ monitoring and analysis of cardiac susceptibility and change without the drawbacks normally associated with full electrophysiologic studies or Holter monitoring. Alternatively, it is also of substantial benefit to combine features of the above invention to portable external monitoring systems to afford non-permanent ambulatory analysis having extraordinary accuracy and predictive value without substantial encumbrance of the patient. Indeed such a systems will likely prove more efficacious than existing ambulatory monitoring systems in establishing baseline recordings which will provide well-defined intervention criteria and lead to demonstrably improved therapy, both prophylactically as well as reactive to cardiac events.

Thus, it is possible to stimulate externally while sensing and processing the above described signals with permanent or temporary internal system components; or it is possible to stimulate internally and detect and process internally; or in other embodiments it is possible to stimulate internally or externally and detect externally using mobile units such as a mobile pack or the like. In various embodiments of these systems and methods it may be necessary to stimulate so as to capture the ventricle, or be synchronous with the R-wave, in order to avoid patient compromise and to optimize performance. Overall, however, these are techniques that differ in the context of this use form normal threshold testing or mapping techniques.

These embodiments also allow for use of this technology in ways not envisioned or even perceived possible before. For example, in one embodiment, an implanted defibrillator or pacemaker can also periodically establish cardiac baseline analyses using the sub-threshold stimulation and sensing techniques described above but installed in the implanted unit. Moreover, with proper placement, it may be possible to locate the requisite sensing means for this invention at various depths beneath the surface of the patient's external anatomy. Baselines or other analyses may also be performed with the external portable systems described above, or with a partially implanted system component such as a lead configured with stimulation or energy delivery means placed in or near the heart. The further advantage of these new systems is the relatively small amount of energy consumed by such baseline tests and analyses of this invention, a fact of particular relevance to implanted systems. Another advantage of this system is the ability to conduct sub-threshold baseline testing both before and after supra-threshold stimulation, e.g. a defibrillation shock, to consistently and accurately monitor cardiac risk factors, tissue rate of change indicia, heart rate variability, memory effect, or other phenomenon.

Analysis was performed regarding Wavelet decomposition of Wedensky modulated signal averaged electrocardiograms. Investigations were performed utilizing electrocardiographic recordings supplied by Harbinger Medical.

The recordings analyzed originated from Wedensky modulated signal averaged electrocardiograms and were supplied in pairs for each investigated subject. These pairs contained both signal averaged modulated electrocardiograms and control electrocardiograms obtained from unmodulated alternating cardiac cycles. Each recording was given in three orthogonal leads both unfiltered and digitally filtered. The analysis performed utilized the unfiltered recordings.

As with the previous set of electrocardiograms that were processed at the end of 1998, each triplet of orthogonal signal average leads was subjected to the wavelet analysis using 53 scales of Mornet wavelet and from the resulting orthogonal wavelet decompositions, wavelet vector magnitude was calculated. The data of the wavelet vector magnitudes were stored digitally on a dedicated personal workstation and used for a extraction of characteristic parameters. All the data is available and if any further analysis is needed, the computation of the wavelet decomposition does not need to be repeated.

For the purposes of the analysis of this data set, a new version of the wavelet decomposition software package has been programmed. The original implementation which utilized Borland Pascal was transferred into C++ and implemented using a 32 bit compiler by Watcom. A substantial gain in processing time was achieved in this way. With the present version, processing of one set of three orthogonal electrocardiograms including the computation of the wavelet vector magnitude takes approximately four to five minutes on a personal computer equipped with a 450 MHz Pentium II processor. While programming this new implementation of the decomposition system, further experience has been gained and further reprogramming concepts developed that should potentially allow the processing of one recording to be achieved within less than one minute on a suitable fast personal computer.

The parameters extracted from the vector magnitudes of wavelet decompositions were firstly related to the individual decompositions and secondly taken from the differences of the Wedensky modulated and reference recordings that were obtained within the same experiment.

The parameters extracted from the individual recording were related to the localized maxima of the wavelet decomposition envelope. Within each wavelet scale, local maxima were counted in a pre-specified interval relative to the R wave of the analyzed electrocardiogram. These counts, taken within the same time segment, were subsequently summed over the whole spectrum of scales. The numerical parameters obtained in this way represented the general smoothness of the wavelet decomposition and was hence likely to differentiate between subjects with and without disturbed intra-cardiac conduction.

The parameters related to the wavelet decomposition residuum, i.e. to the difference between the vector magnitude of wavelet decomposition of the Wedensky modulated and reference electrocardiograms, were based on calculating the surface area of the residuum. For this purpose the residuum was represented also by a 3-D envelope along individual scales of the original wavelet decompositions and the time synchronized in individual scales. Four different segments relative to the R wave as well as relative to the stimulation moment the surface area of the residuum was calculated. For this purpose, the spatial distance between the individual scales was considered negligible and the surface area of the residuum was represented by the sum of the distances along the 2-D graphs corresponding to individual scales within the specified time segment.

Graphical images of both the original wavelet decompositions of the Wedensky modulated and reference electrocardiograms as well as of the wavelet decomposition residua were produced and visually checked on the computer screen. The images did not substantially differ from the images produced with the previous set of recordings at the end of 1998 and were therefore not printed on paper because of the complexity of the technical work involved. Selected images were converted; into transportable bitmaps and used for presentation purposes such as selected slides and poster presentations. Generally, the images suggested that the noise level achieved in the present recordings was slightly lower than compared to that observed previously.

Together with the original electrocardiographic data set, a database of individual subjects was received from Harbinger Medical in which the general clinical distinction between the normal subjects and patients with EP documented ventricular tachycardia was made. From this database, all subjects recorded within the new data set were considered with the exception of 136 recordings that were excluded. As previously observed, the count of wavelet maxima in 50 msec segments distinguishes statistically normal subjects from VT patients.

Figure 59A:
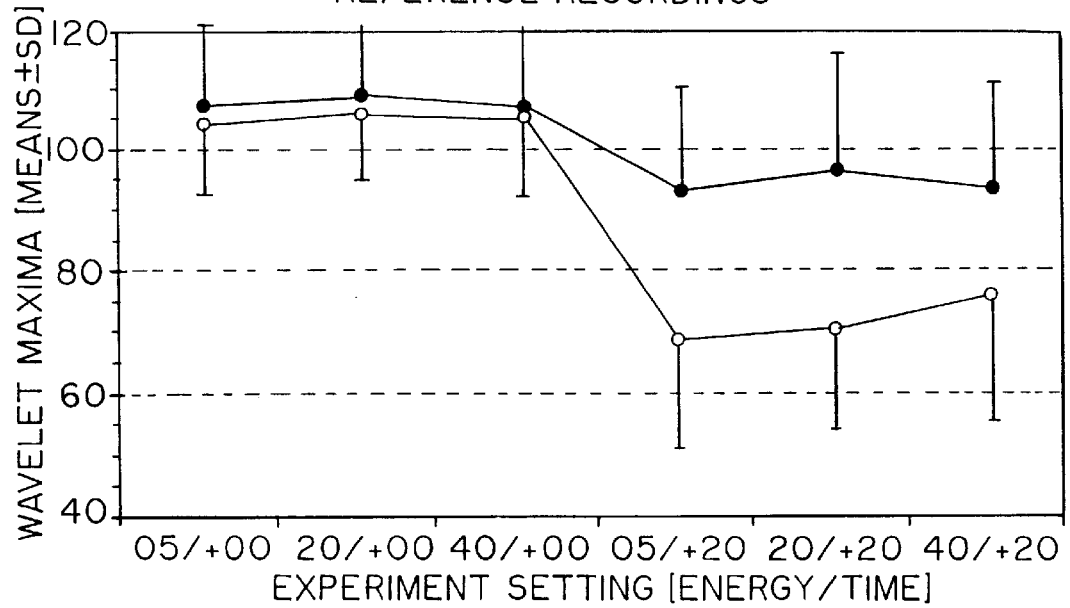
FIGS. 59A–B are graphs depicting data sets of observed data.
Figure 59B:
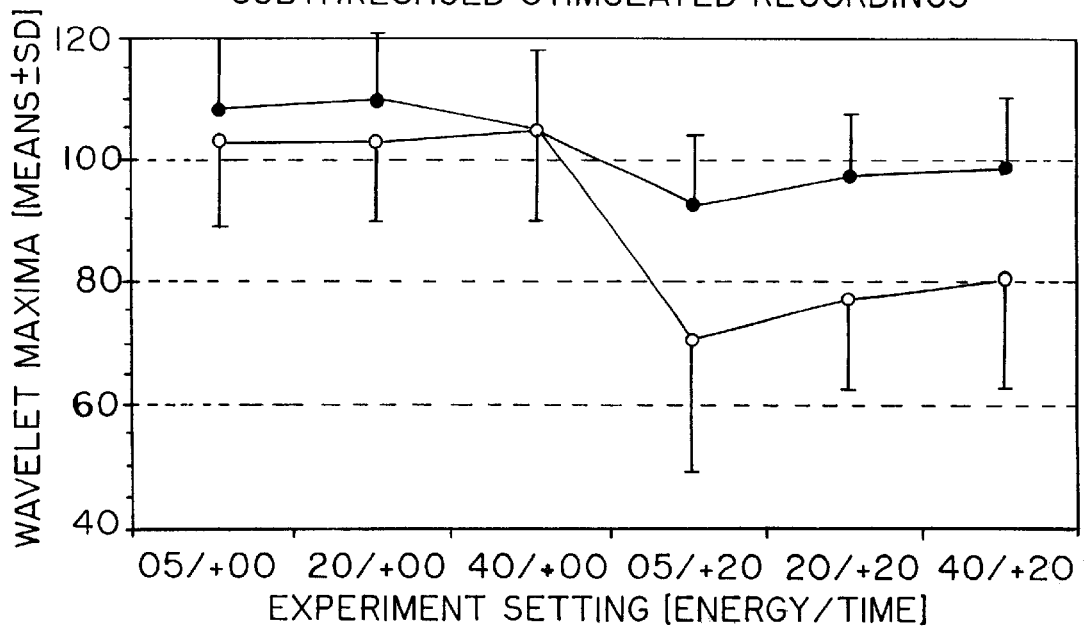
Figure 60A:
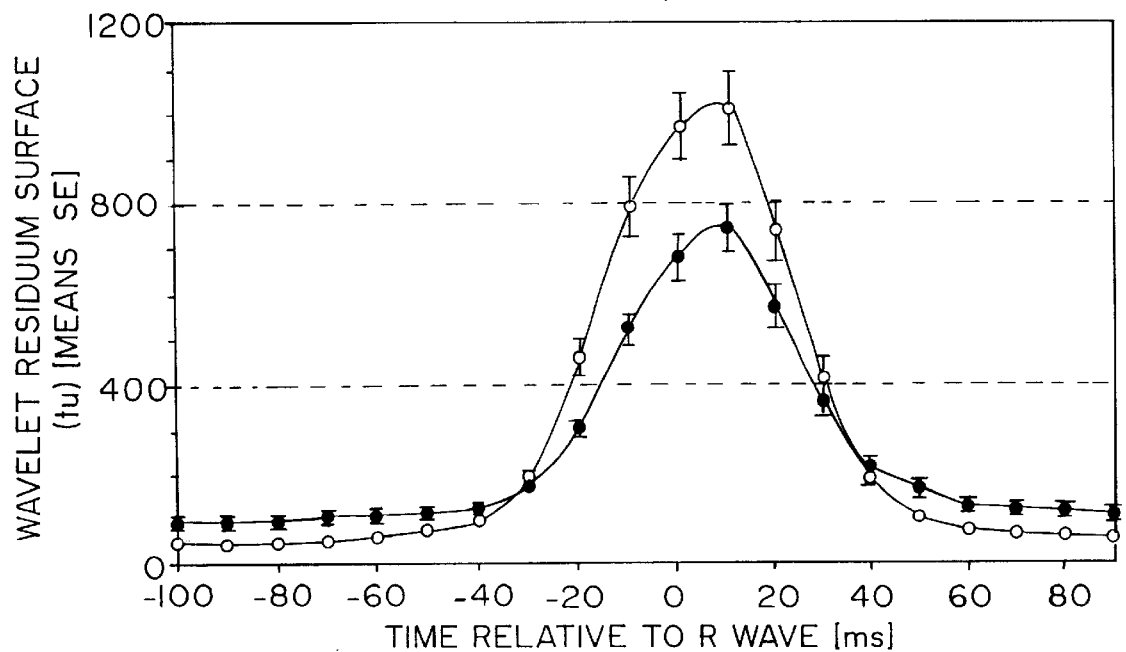
FIGS. 60A–F are graphs depicting data sets of observed data.
Figure 60B:
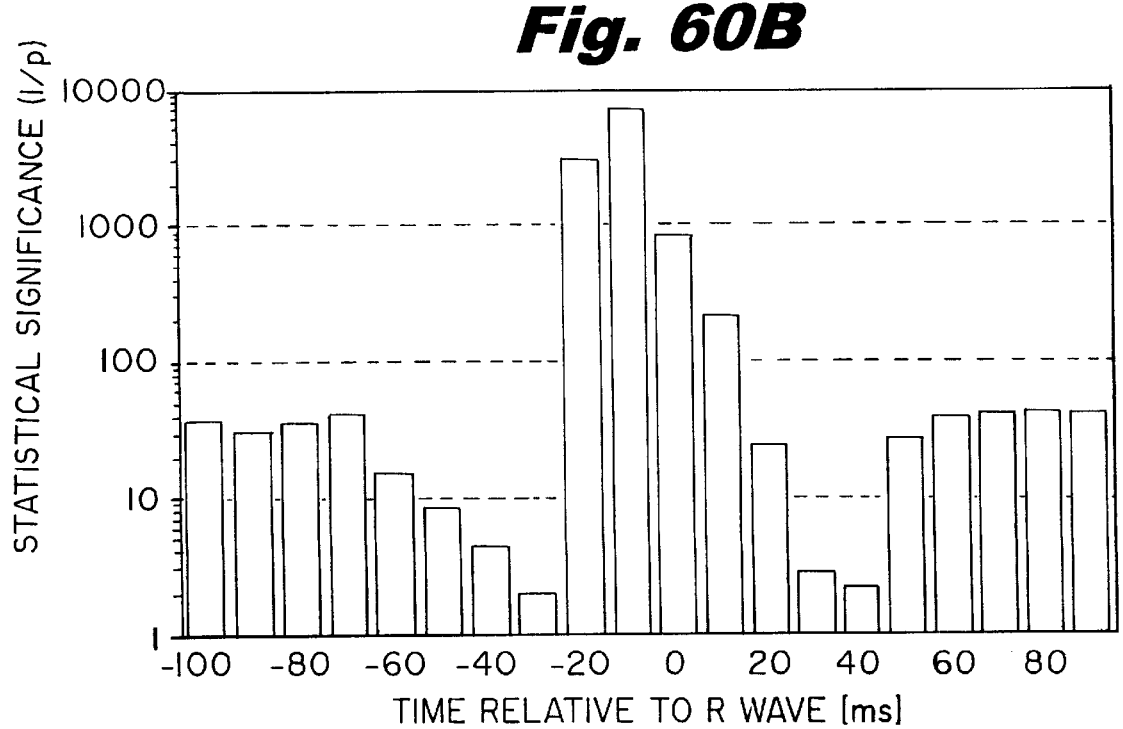
Figure 60C:
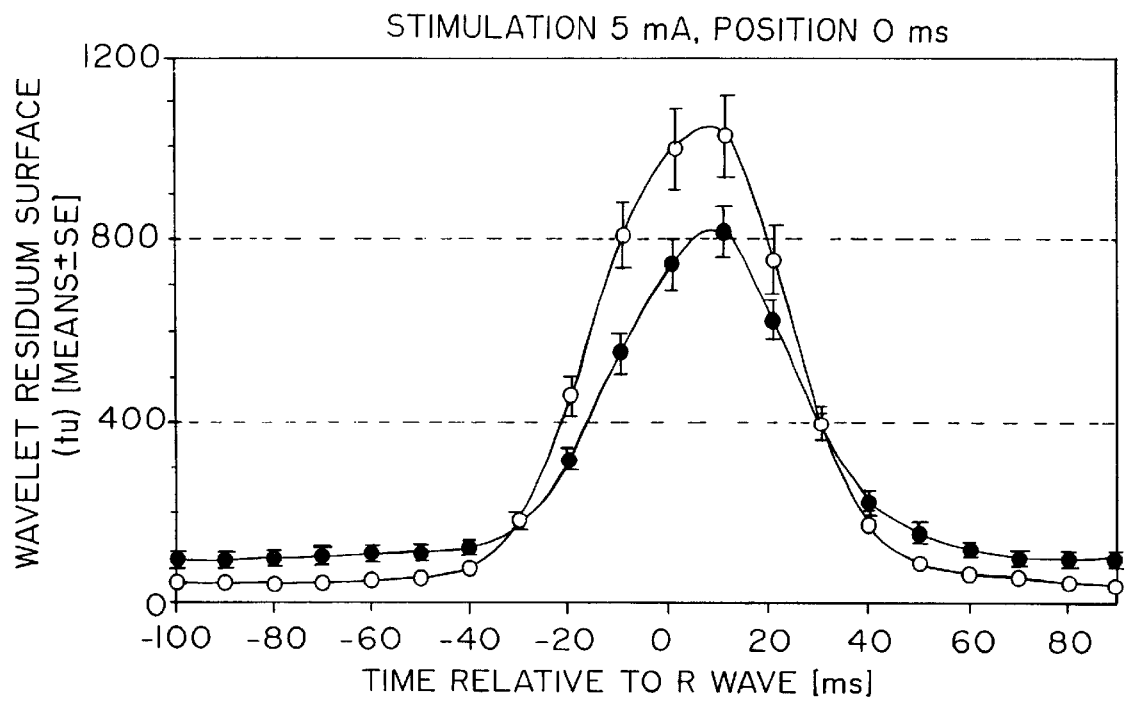
Figure 60D:
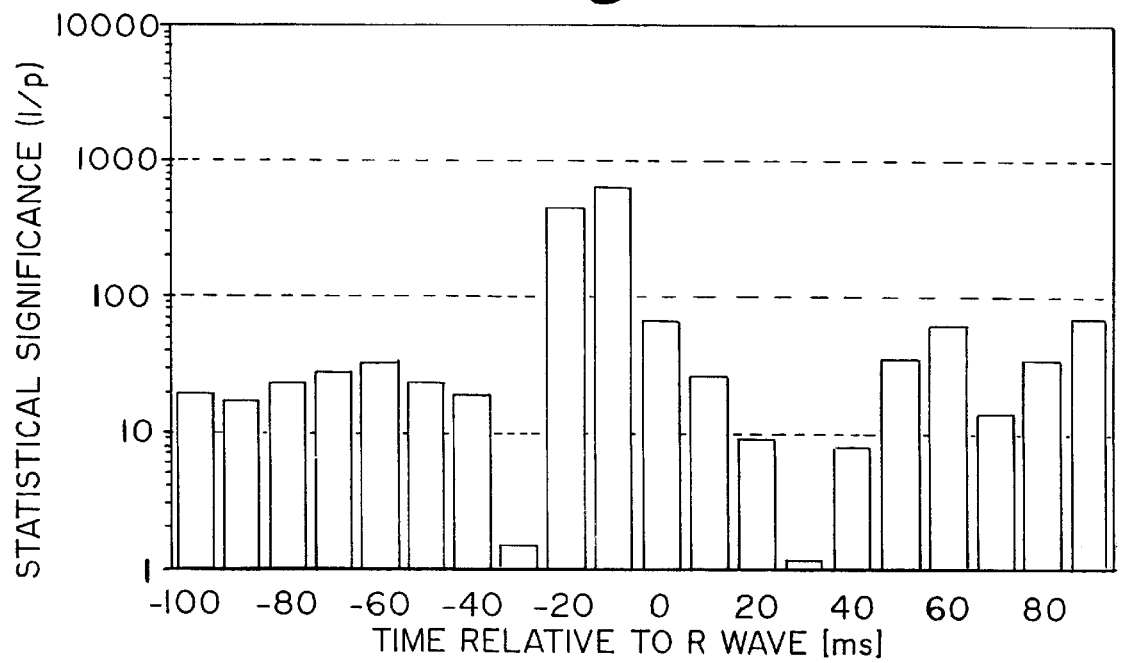
Figure 60E:
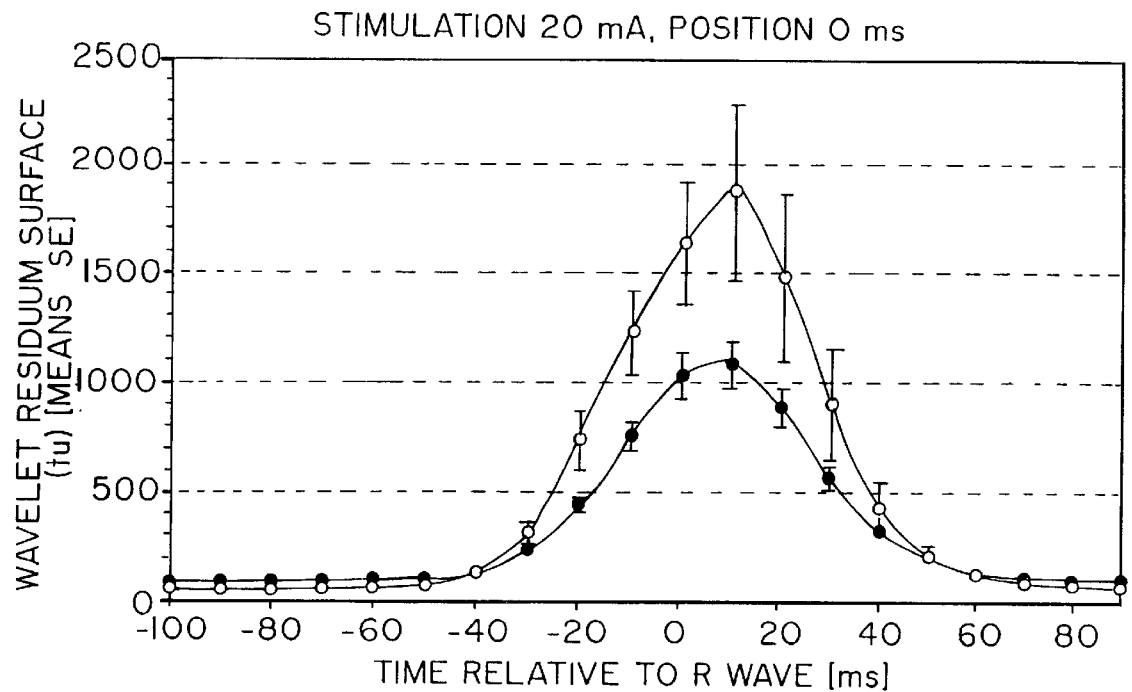
Figure 60F:
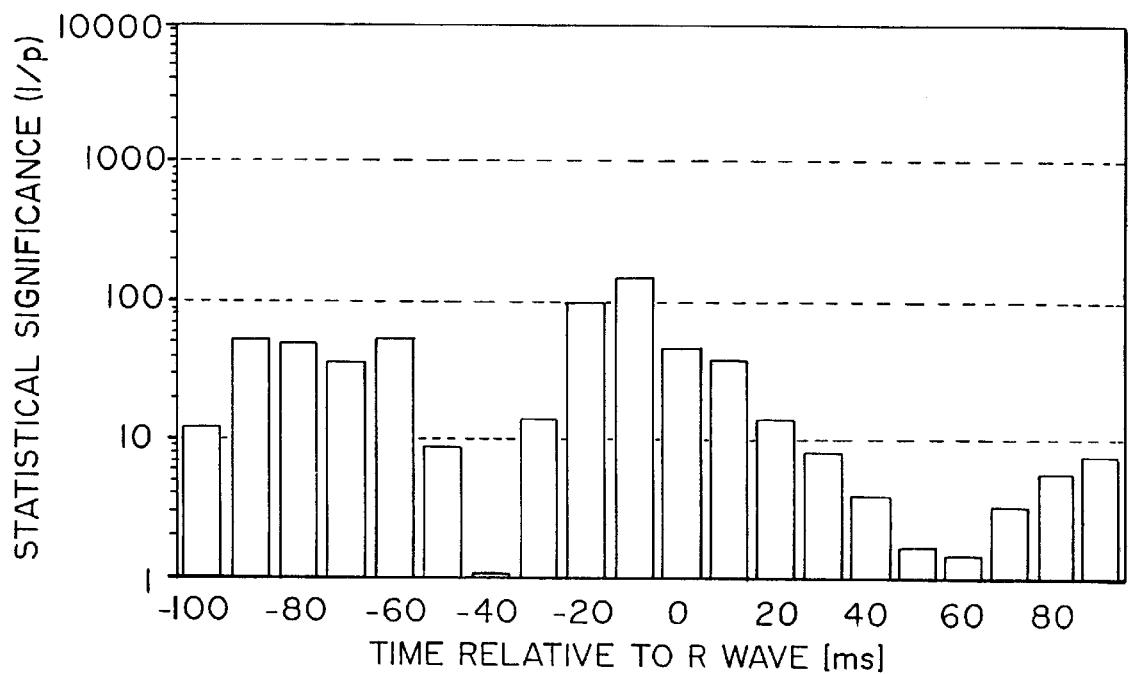

In the present data set, this distinction was observed in both sub-threshold stimulated and reference recordings. The distinction was namely achieved when analyzing the segments shifted by 20 msec from the R wave as seen in the graphs of FIGS. 59A–B. In these graphs, the lines with open circles correspond to healthy volunteers and the lines with the closed circles correspond to patients with EP documented ventricular tachycardia. The same layout of the graphs is maintained throughout the whole of this report.

Contrary to the observations made in the analysis made on the previous set of recordings, the distinction based on the maxima count does not differ between the reference and sub-threshold stimulated recordings. This is in line of our present understanding of the differences caused by Wedensky stimulation in the 3-D wavelet decomposition envelopes which seem to produce a rather smooth additional activation pattern.

Despite this present understanding of the pattern produced by Wedensky stimulation in the 3-D wavelet envelopes, a more systematic study investigating the difference in the wavelet maxima was attempted. For this purpose, the whole 3-D wavelet envelope was divided into non-overlapping 10 msec segments. Within mutually corresponding segments, the wavelet envelope maxima were counted and compared in the reference and sub-threshold stimulated recordings. The differences of these maxima count and the bottom being the reciprocal of statistical significance when comparing the data of individual segments of the wavelet envelopes between normal subjects and VT patients. As can be seen in FIGS. 59A–B, statistical significance seems to be rather disorganized and is not generally convincing.

Similar to the analysis performed with the previous data set, the surfaces of the wavelet residua were calculated in three different modes.

Firstly, the whole envelope of the residuum was divided into non-overlapping segments of 10 msec and comparisons were made between the individual patients and volunteers group (i.e. the groups of subject for whom corresponding experiments were available) for these individual segments. A number of the graphs of the analysis are shown in FIGS. 60A–F. Again, one page is shown for each experimental setting. In the top graph, the original data is shown and in the bottom graph, the reciprocal of statistical significances corresponding to the top graph are listed. The 10 msec segments in which the comparisons were made centered around the times that are shown in the graphs.

Generally, the same observation that was previously made, can be seen in these figures. Healthy volunteers tend to produce higher responses to the sub-threshold stimulations compared to the VT patients. Because of the leakage of the signal in calculating the original wavelet envelopes and their residual difference, the change produced by the sub-threshold stimulation is seen both after and before the sub-threshold stimulus. The separation of the groups, however, tends to be more prominent in segments following the stimulation moment.

The only exception of this general rule is the graph showing the stimulation of 20 mA at the position of 30 msec after the R wave detect. In this situation, the inverse relation between the normal subjects and VT patients was noticed, which is probably due to the small number of individuals involved in this test. All other results are consistent with the previously made observations.

Figure 61A:
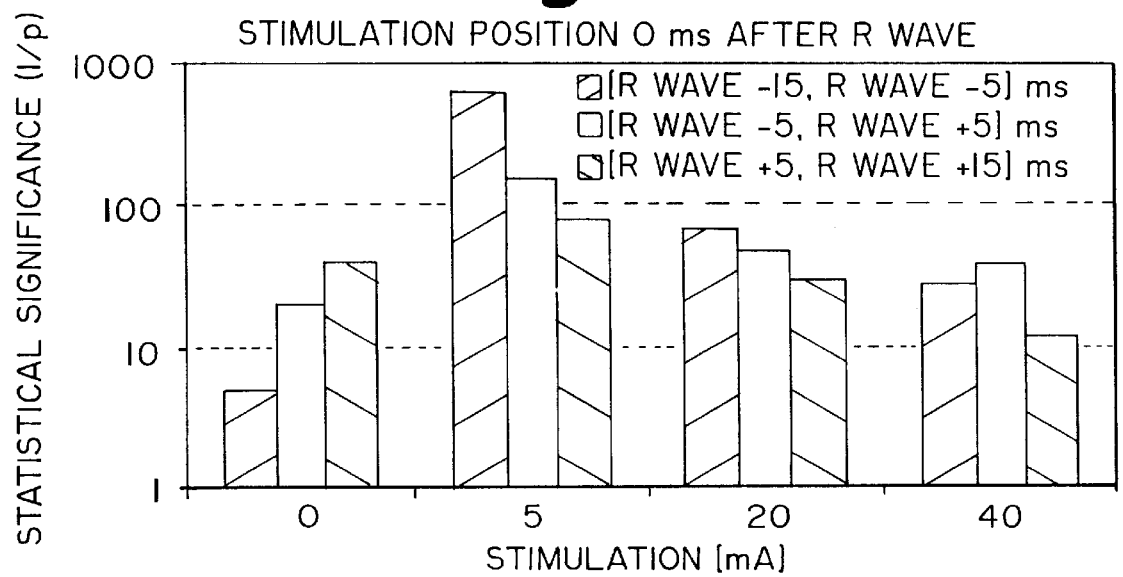
FIGS. 61A–B depict graphs of the dose response evaluation.
Figure 61B:
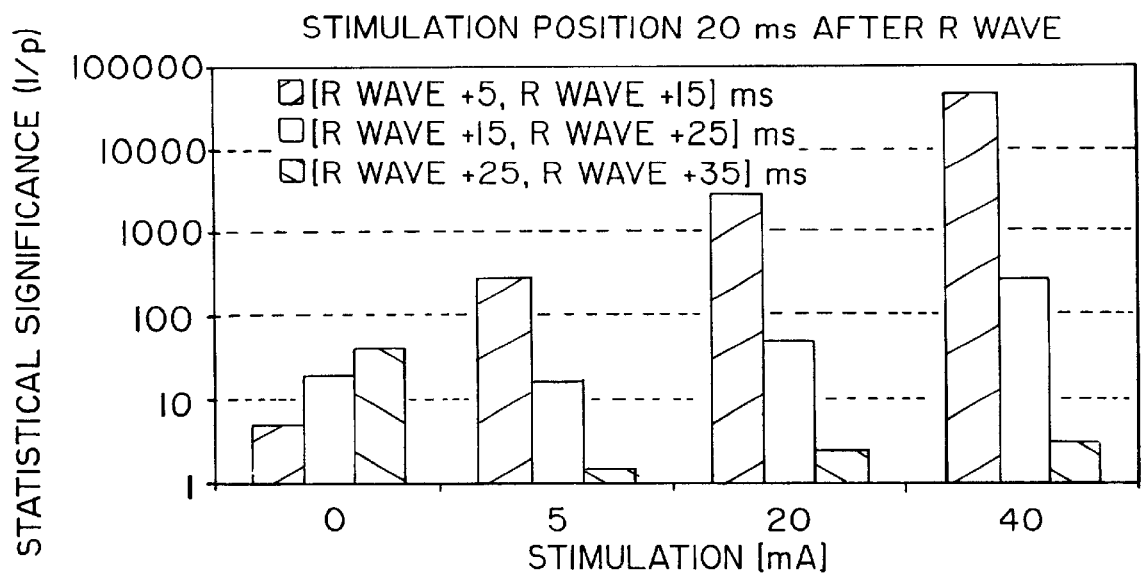
Figure 62A:
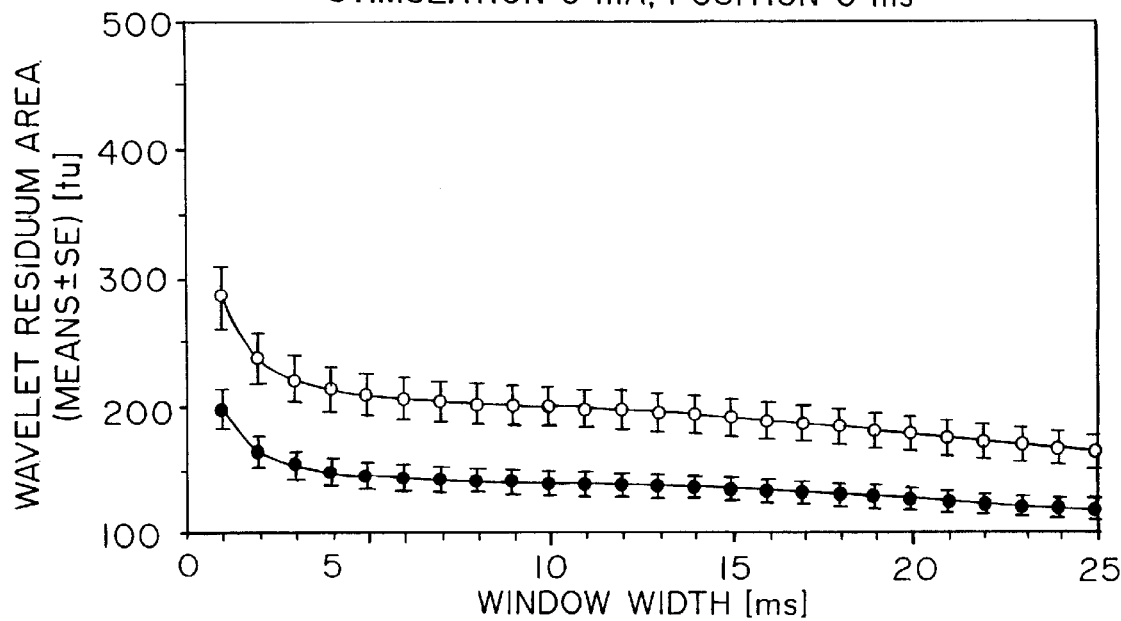
FIGS. 62A–F are graphs depicting comparisons in windows symmetric around the R wave.
Figure 62B:
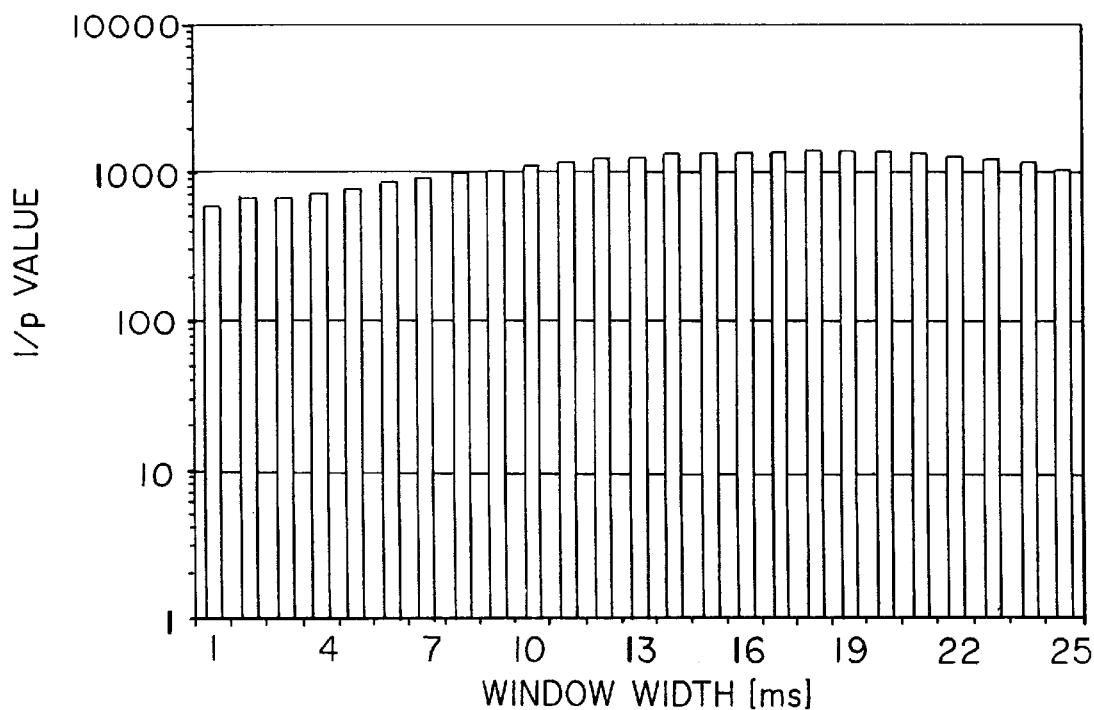
Figure 62C:
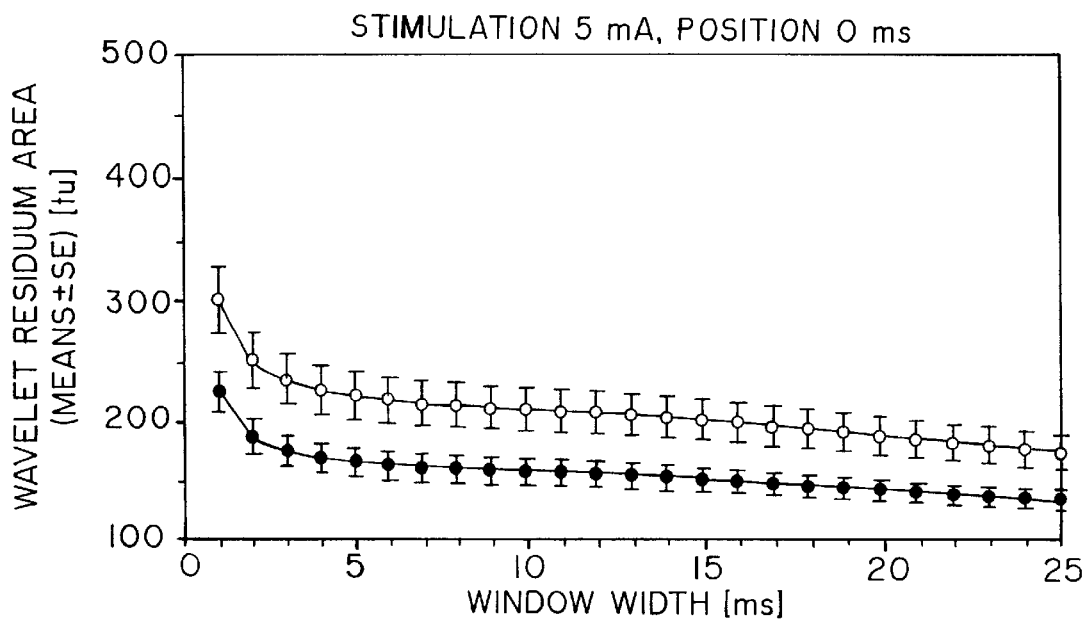
Figure 62D:
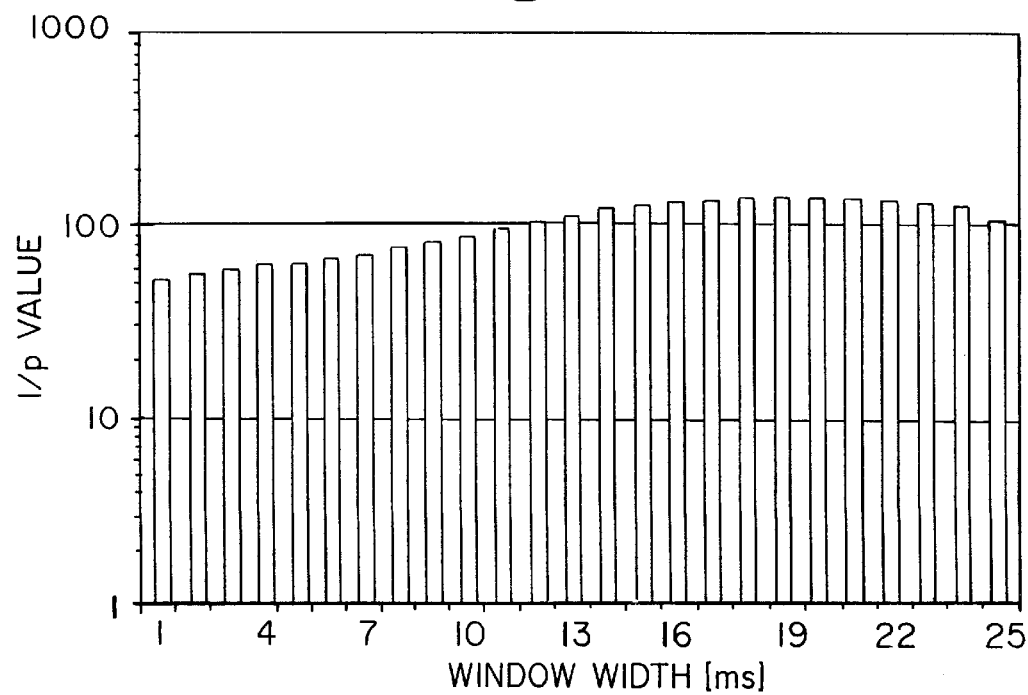
Figure 62E:
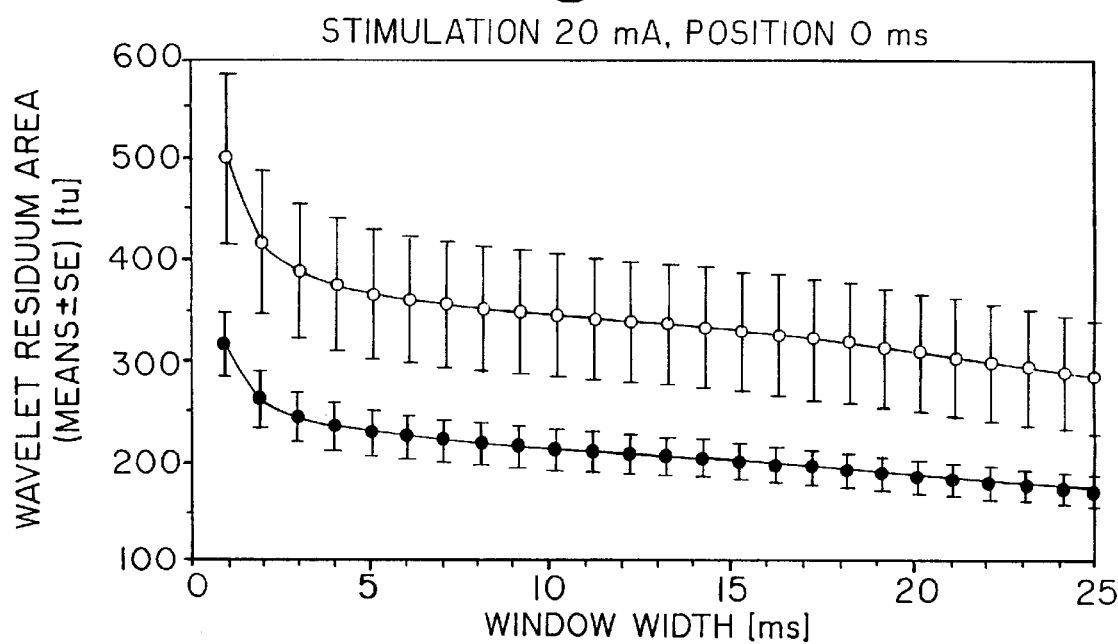
Figure 62F:
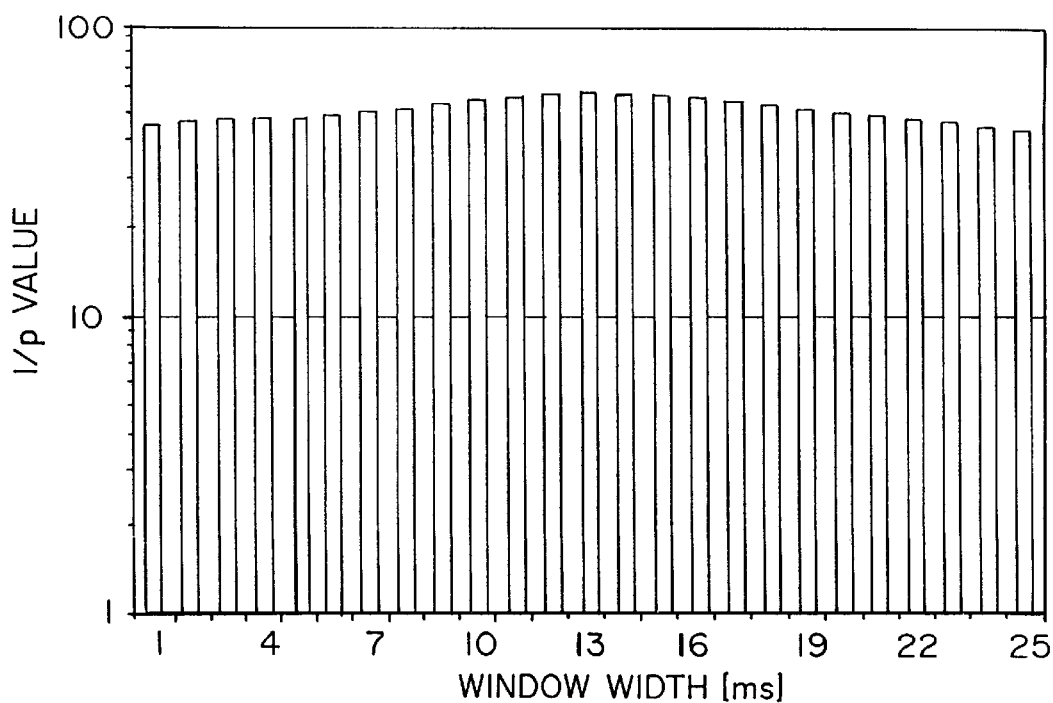
Figure 63A:
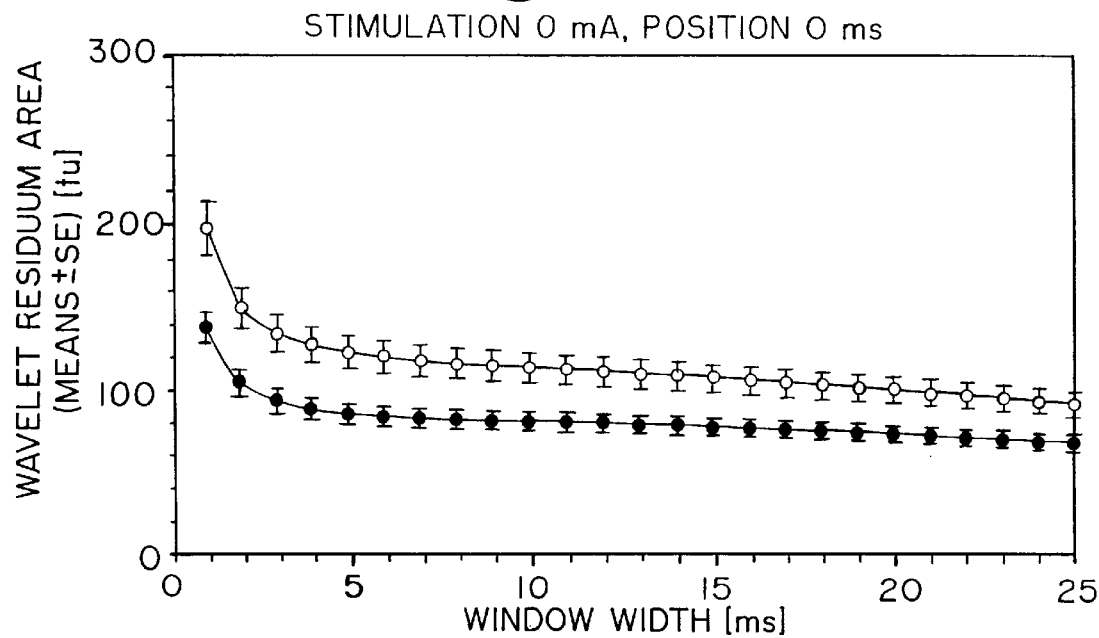
FIGS. 63A–F are graphs depicting the corresponding analysis of FIGS. 63A–F in segments following the R wave.
Figure 63B:
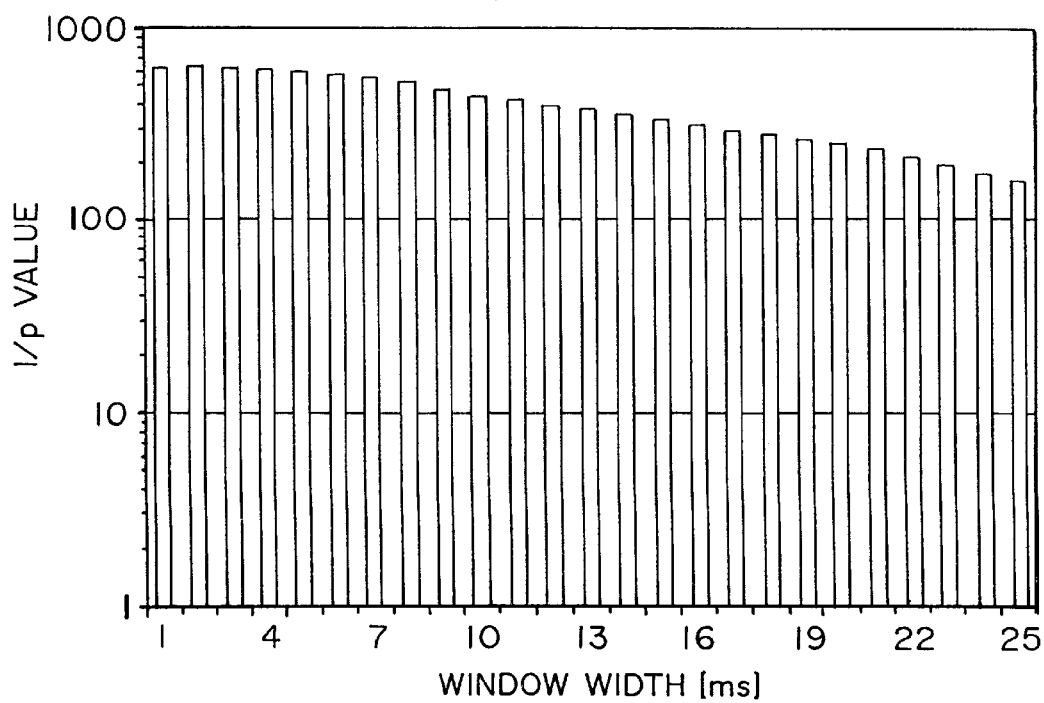
Figure 63C:
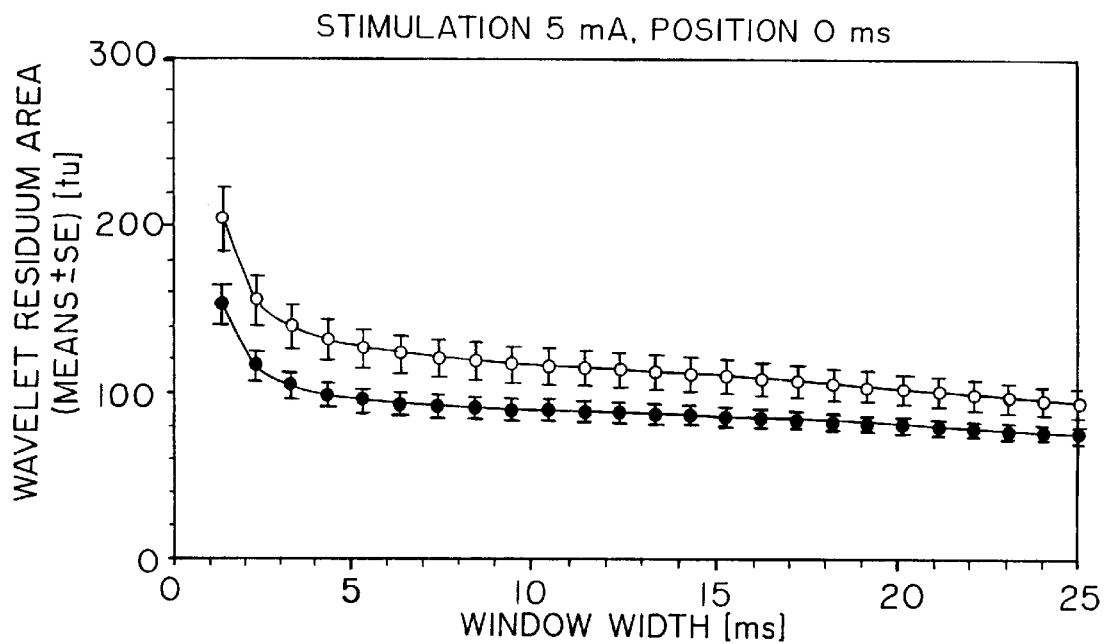
Figure 63D:
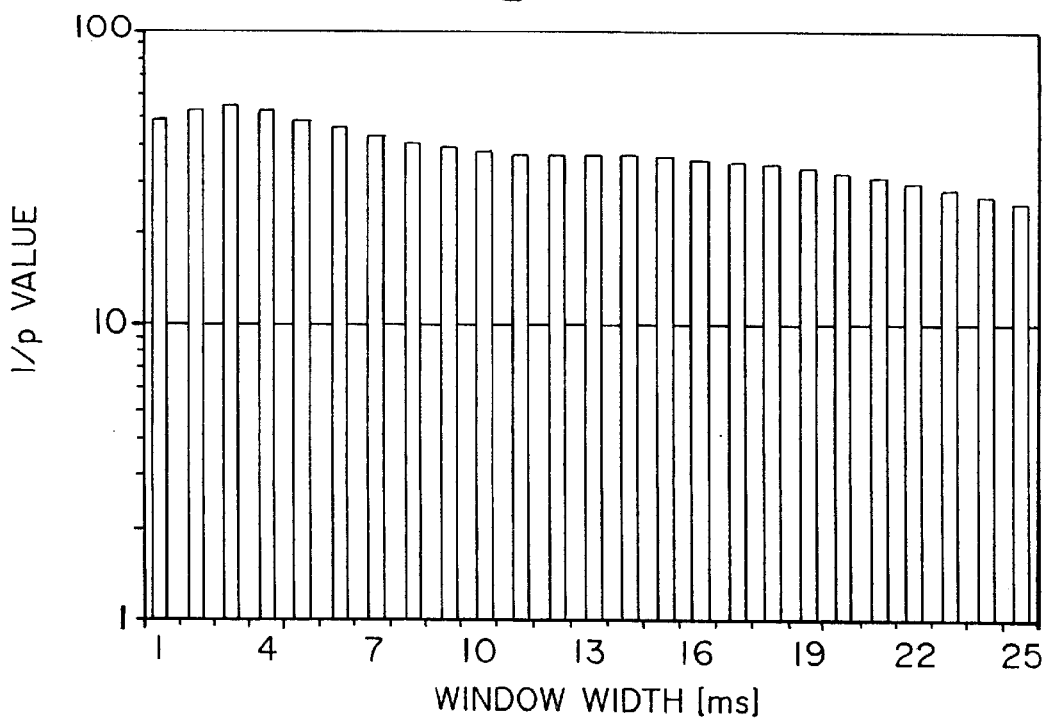
Figure 63E:
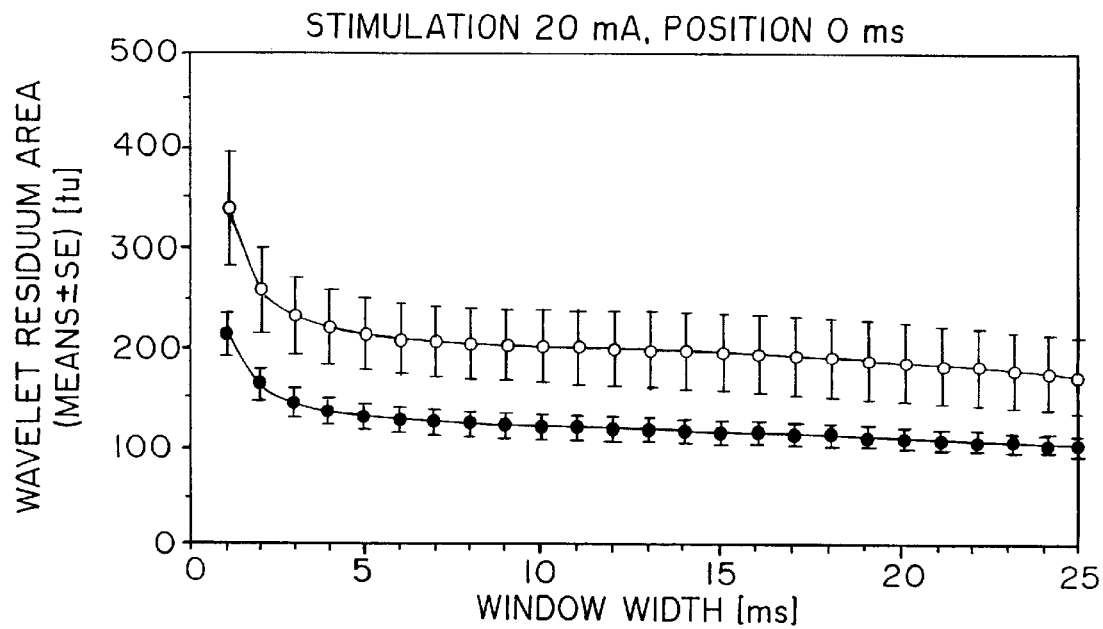
Figure 63F:
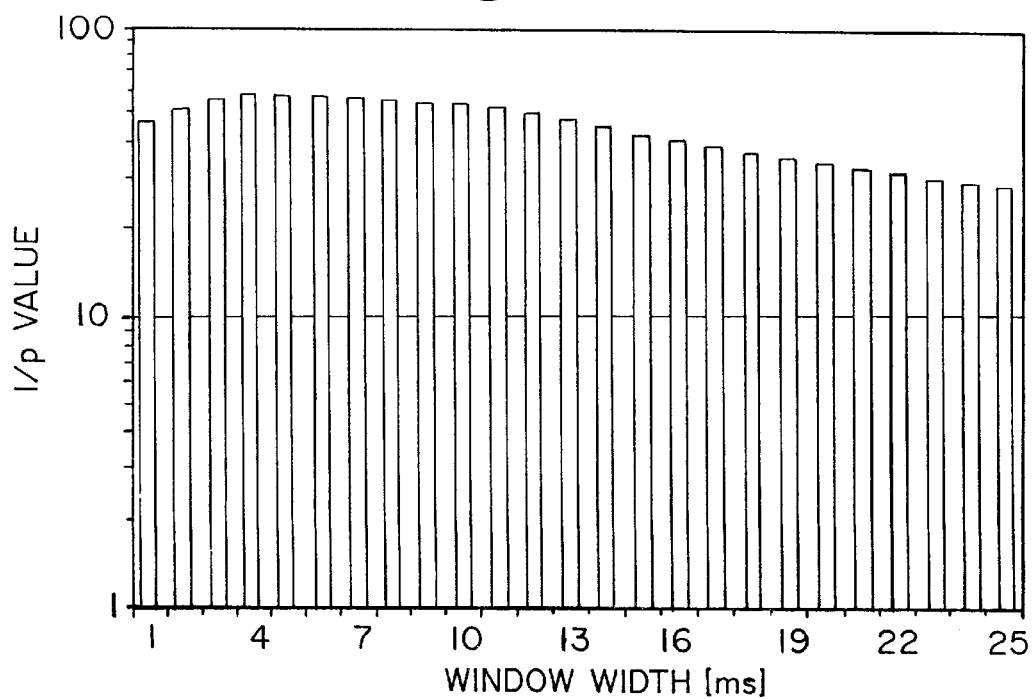

The evaluation of the dose response to the separation of the clinical groups in respect of the stimulation analogy was attempted for the stimulation synchronous with the R wave and for the stimulation delivered 20 msec after the R wave because only in these cases, a sufficient number of individuals were available for a comparative study. The graphs of the dose response evaluation are shown in FIGS. 61A–B. For both positions, reciprocal of statistical significance are shown for three different segments following the R wave and difference stimulation energies.

Both graphs are highly suggestive of a dose response effect which is different for the stimulation synchronous with the R wave and delayed by 20 msec. However, these observations are to some extent at odds with the observations of the dose response affect made in the analysis of the previous data set. Consequently, the issue of the dose response effect and, likewise, of the optimum stimulation energy should be further investigated.

To guide further investigations in respect of the optimum analytical window positioning and width, a comprehensive analysis was performed comparing the residuum surfaces in windows related to the R wave of different duration. Graphs showing to comparisons in windows symmetric around the R wave are shown in FIGS. 62A–F while graphs showing the corresponding analysis in segments following the R wave are shown in FIGS. 63A–F.

Generally, it can be concluded that an optimum window should be centered around the sub-threshold stimulation moment and that it should last for at least 10 to 20 msec to achieve a suitable separation of the clinically relevant responders and non-responders to the Wedensky phenomenon.

The observations previously made, especially those that the wavelet residuum surface distinguishes normal subjects from patients with EP documented ventricular tachycardia were not artifactual and seem to be firmly established by these observations. A further study is needed to establish whether these differences are related to the presence of ventricular tachycardia of whether they are merely related to the presence of the underlying cardiac condition such as the ischaemic heart disease. For this purpose, a group of patients with a post-infarction ischaemic heart disease and uncomplicated follow-up after myocardial infarction should be performed. By comparing the Wedensky phenomenon related parameters recorded in such patients to the corresponding parameters recorded in patients with ventricular tachycardia, it will be possible to elucidate whether the observations of the different characteristics of the noninvasively induced Wedensky phenomenon are related to ventricular tachycardia and whether they carry potential prognostic significance.

Because of the small number of subjects involved in the individual studies and because of the difference of the protocol in individual subjects, the data presently available does not allow a firm conclusion on the optimum stimulation moment or on the optimum stimulation energy to be made. Because of the substantial differences in the phenomenon induced synchronously with the R wave and delayed after the R wave, the possibility of stimulating prior to the R wave should be carefully considered. It is also not obvious whether grouping the individual subjects according to the stimulating energy in milliamperes is the optimum procedure. It might be more appropriate to consider the true energy delivered during the stimulation since the same current might have different effects in different individuals with different trans-thoracic impedance.

If the appropriateness of the present setting of computing the wavelet residuum surface is confirmed in the study of uncomplicated ischaemic heart disease patients, search for additional data analytical procedures will probably not be necessary. Once such a confirmation is available the development of a standard version of the data analytical procedures should be organized so that an analytical system can be distributed to different centers which will allow to compare results obtained in a truly multi-site manner.

Embodiments of the present invention also included analysis of computer simulations of optimum electrode configuration for the induction of noninvasive Wedensky Phenomenon in man. A technical study was conducted that used a 2-D computer model of trans-thoracic cross-sections to simulate current density within ventricular myocardium with a special aim of investigating the optimum properties of an electrode system that might be used for the noninvasive induction of Wedensky phenomenon in man.

An anatomical atlas has been used to select three representative cross-sections of the human thorax within the lower mediastinum that corresponded approximately to the upper (FIG. 64A), middle (FIG. 64B) and lower (FIG. 64C) cross sections of ventricular myocardium.

Figure 64A:
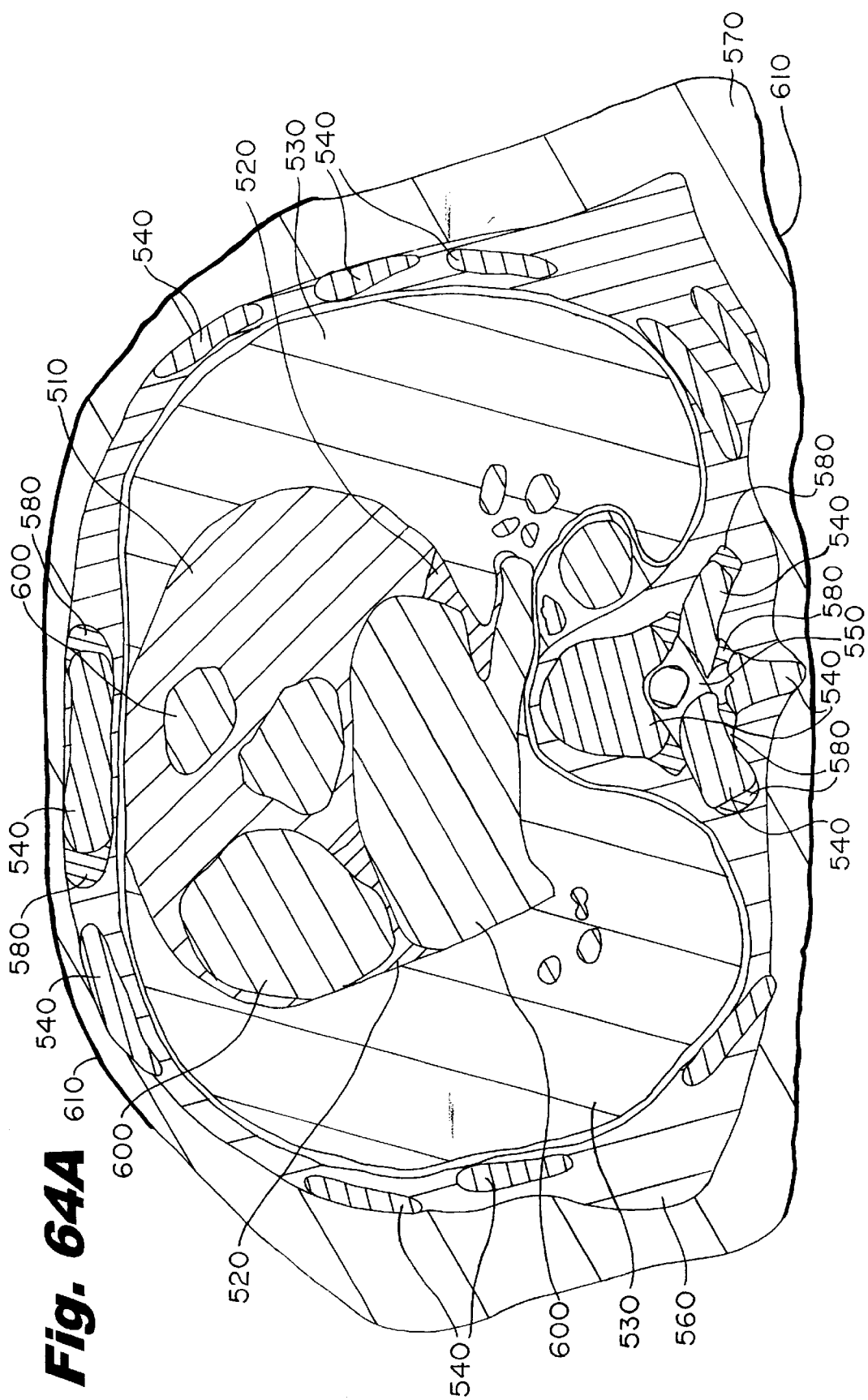
Figure 64B:
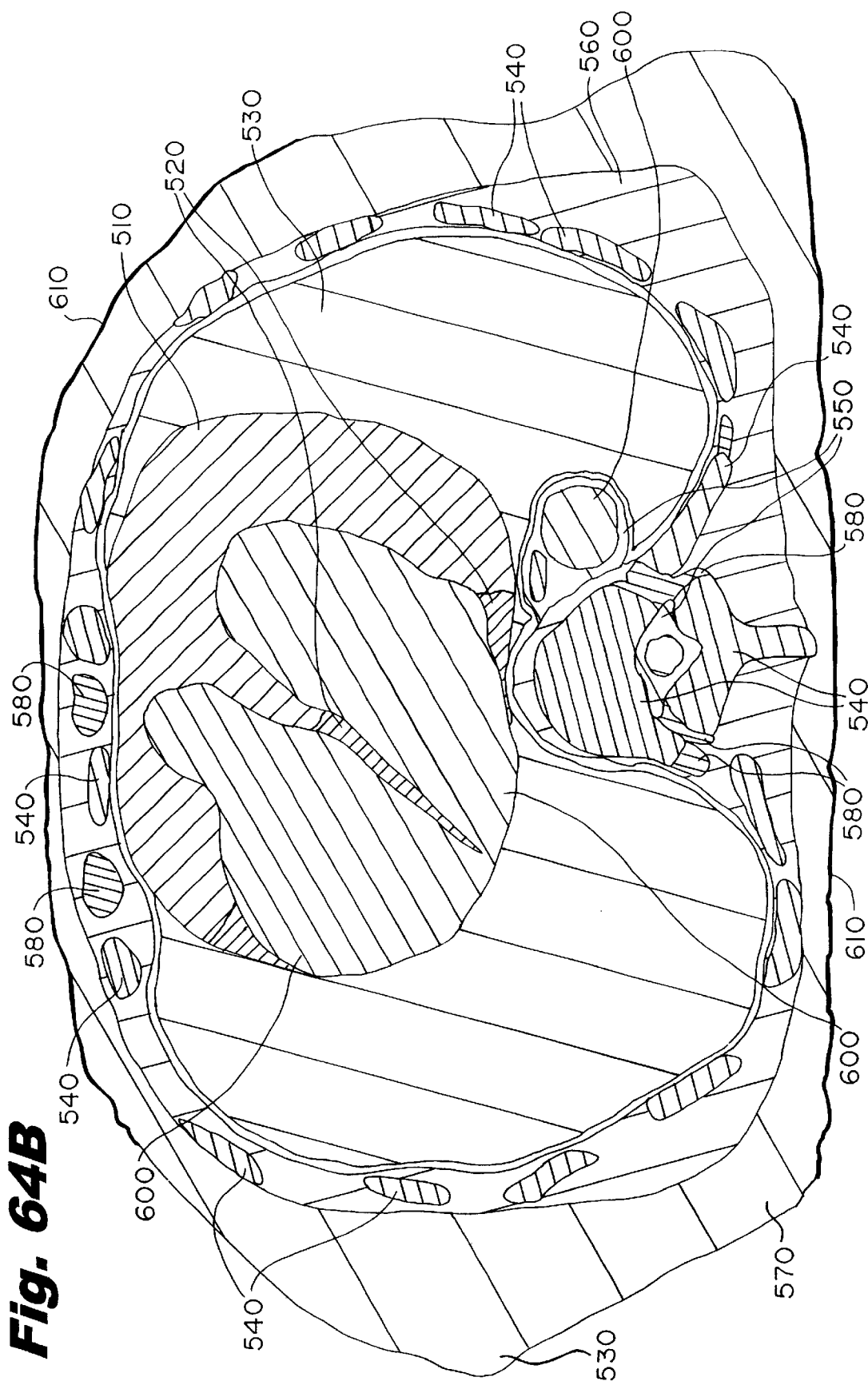
Figure 67B:
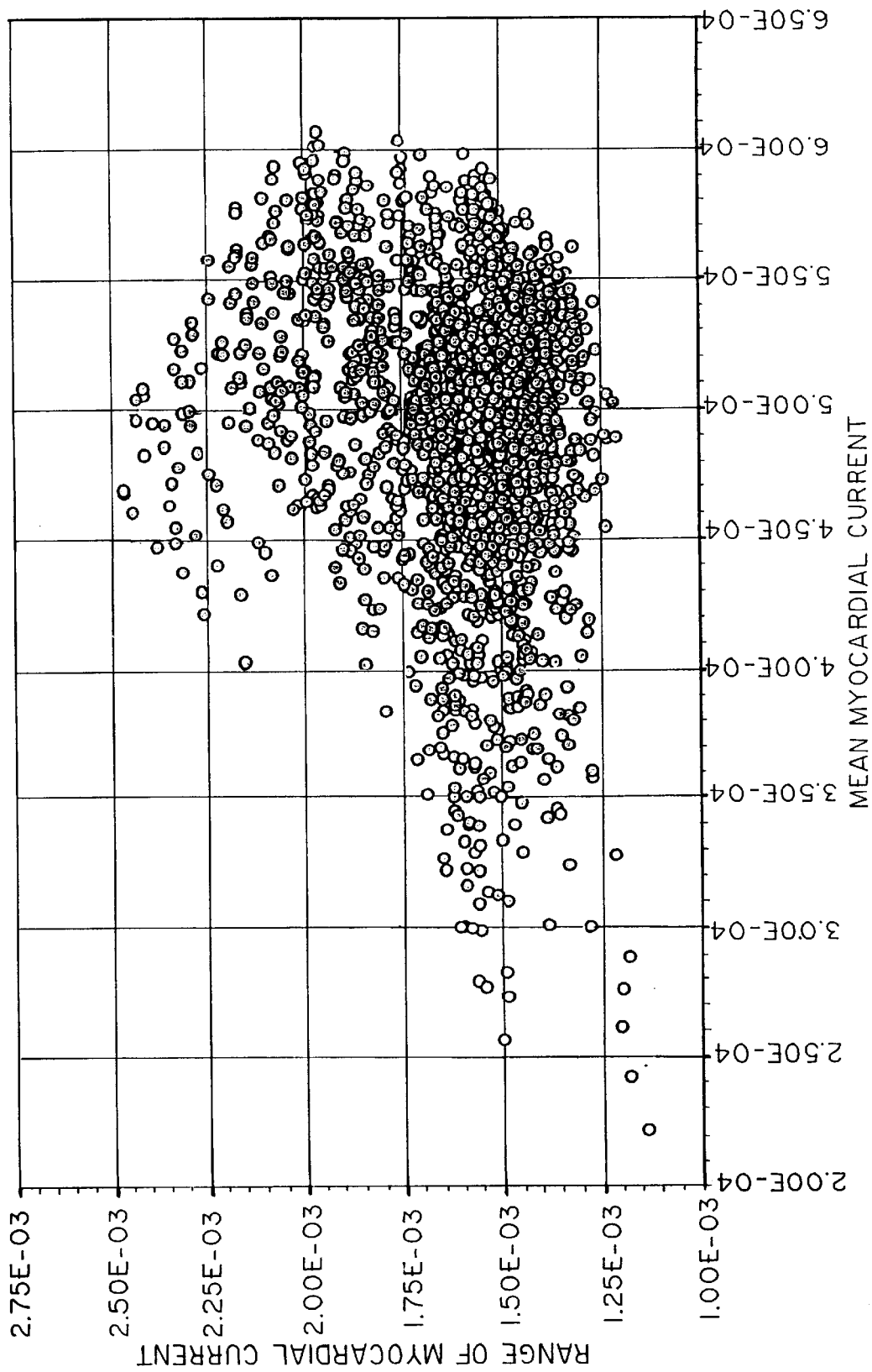
Figure 67C:
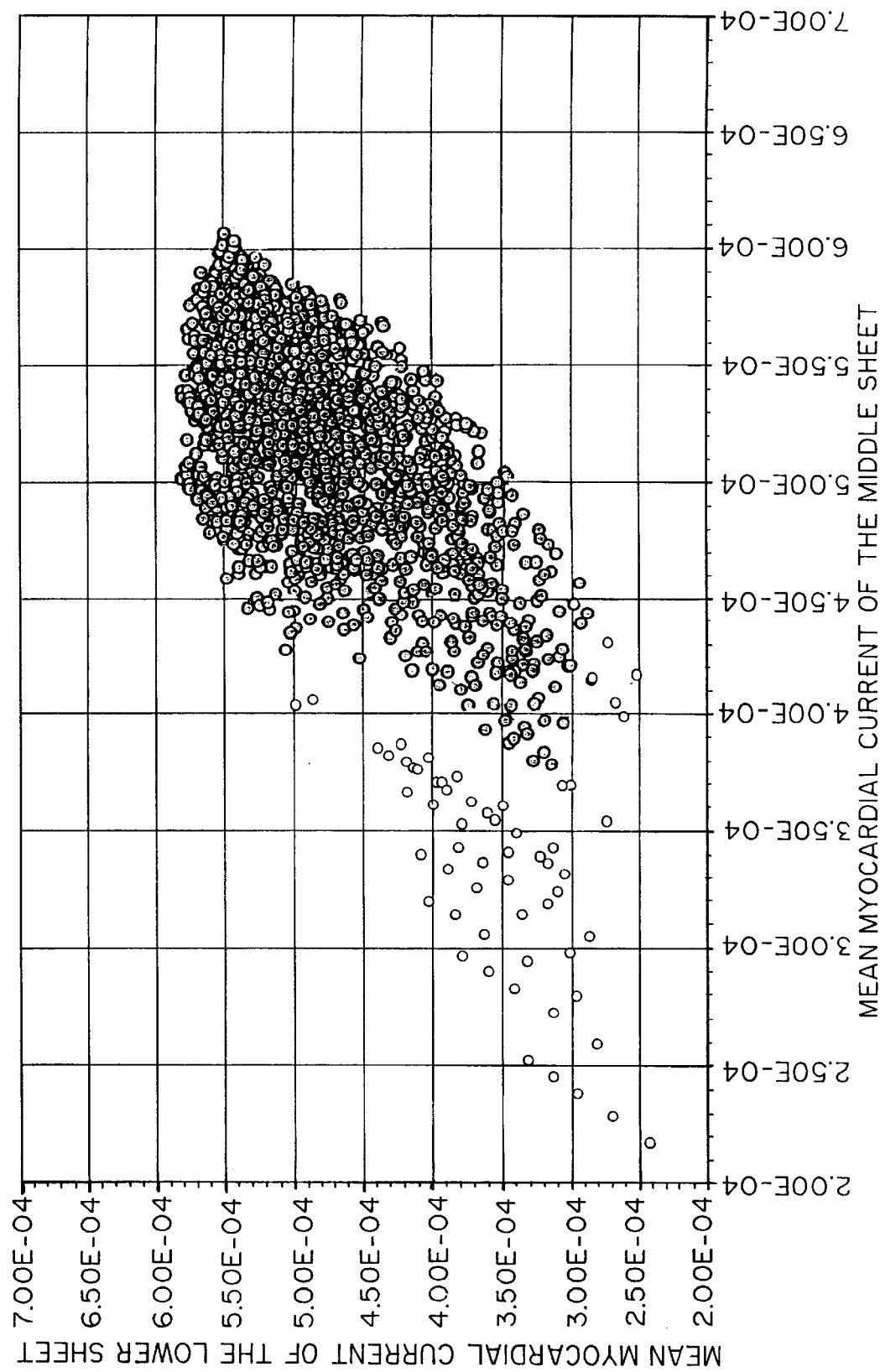
Figure 67D:
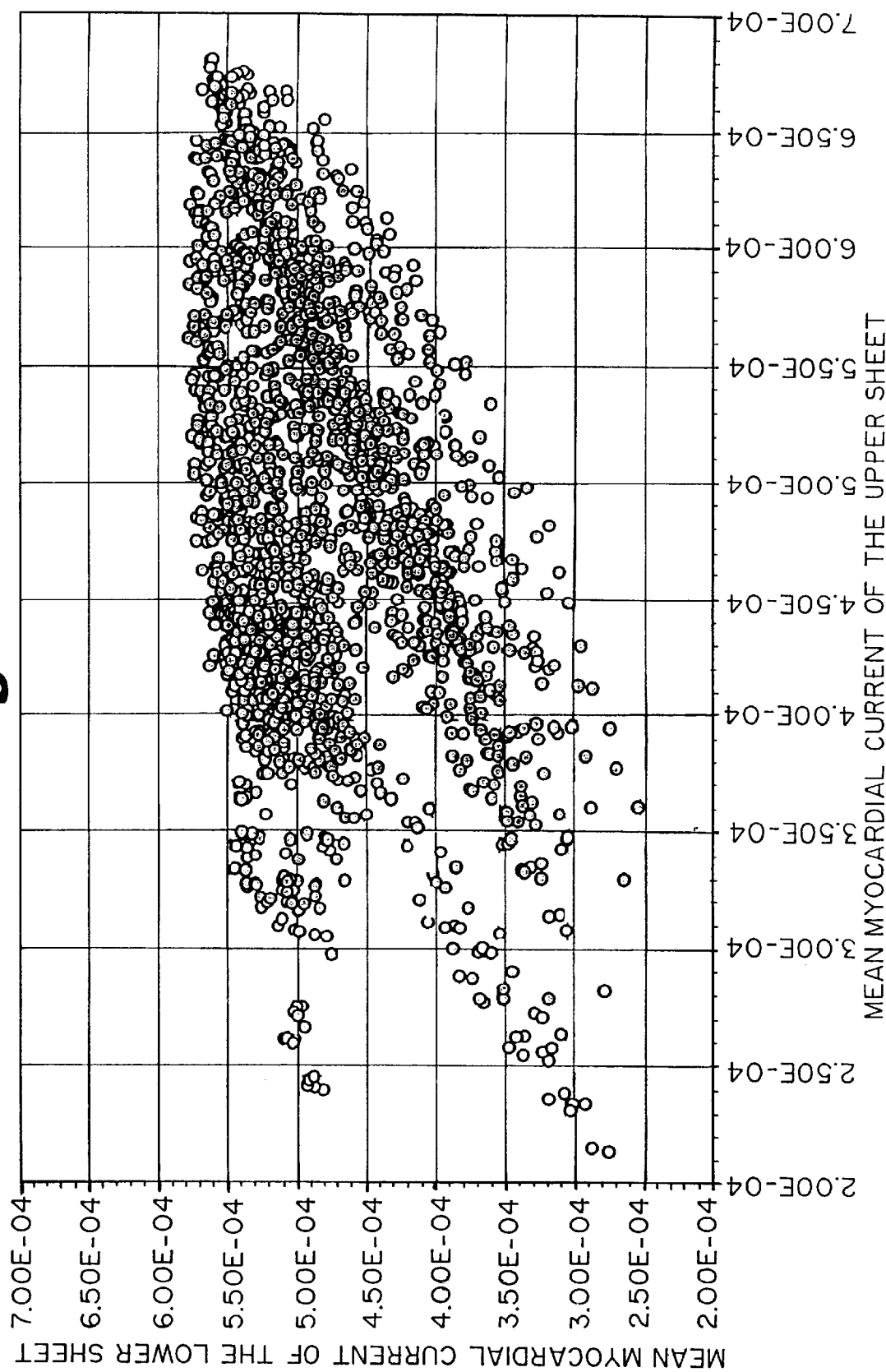
Figure 67E:
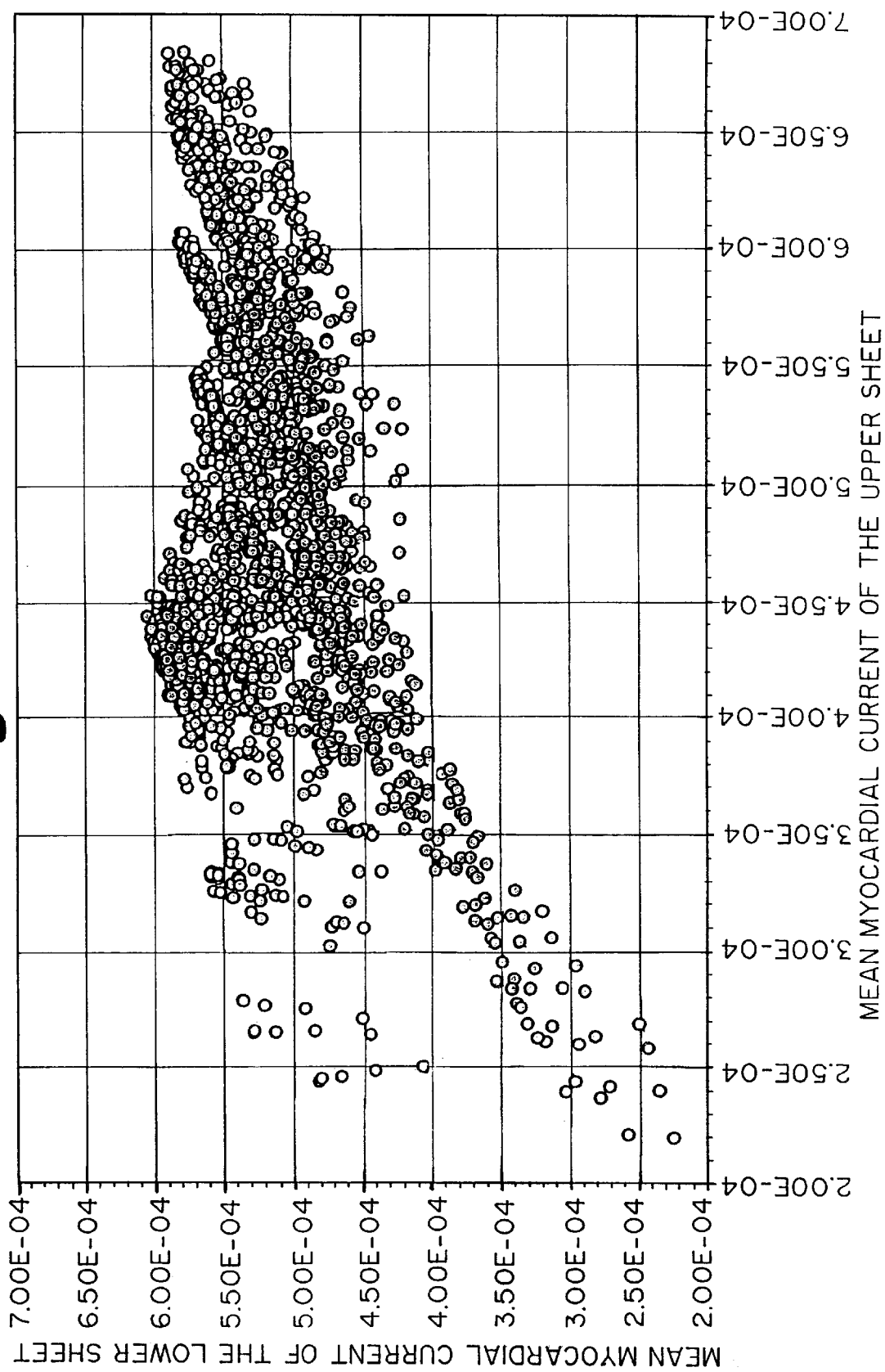
Figure 67F:
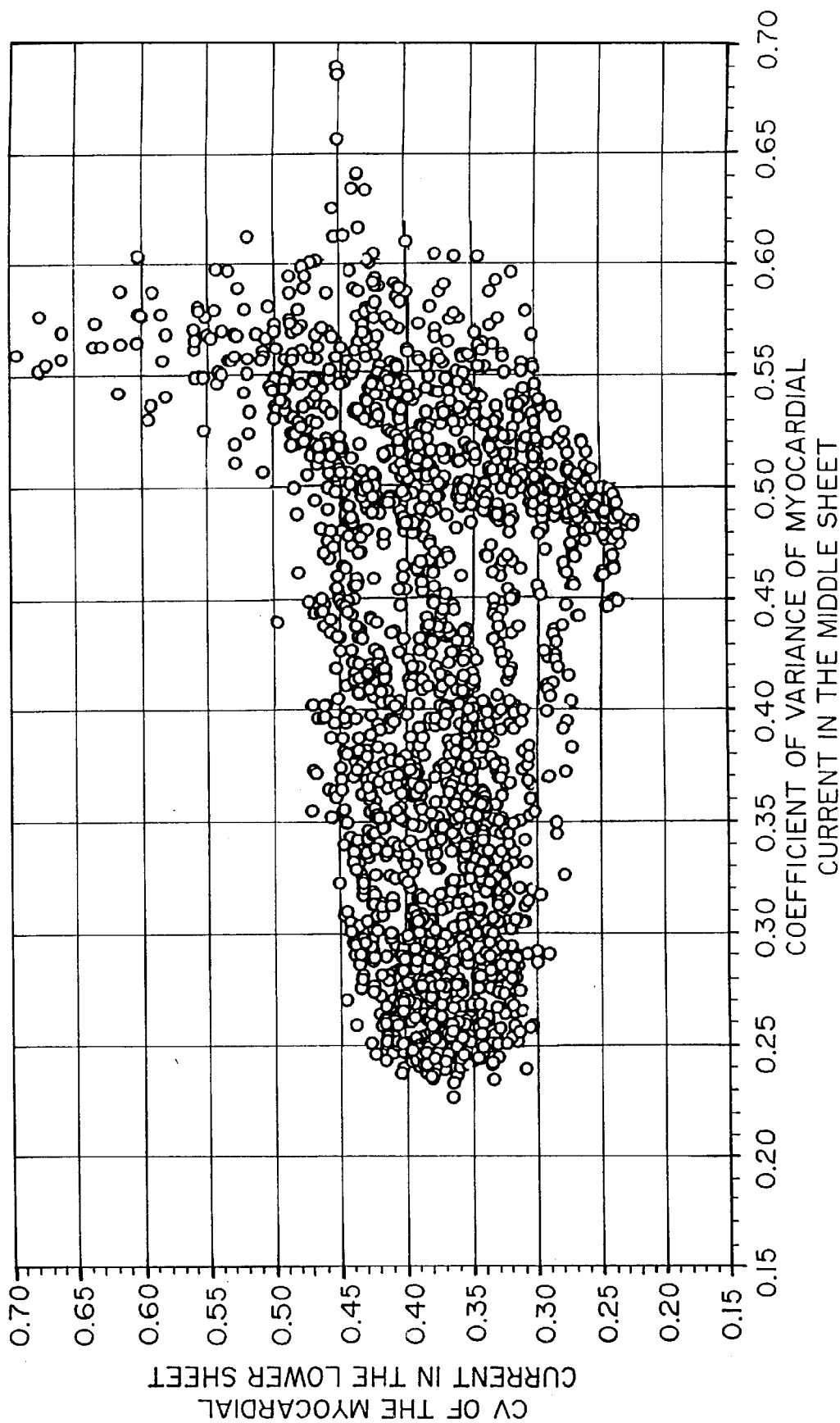
Figure 67G:
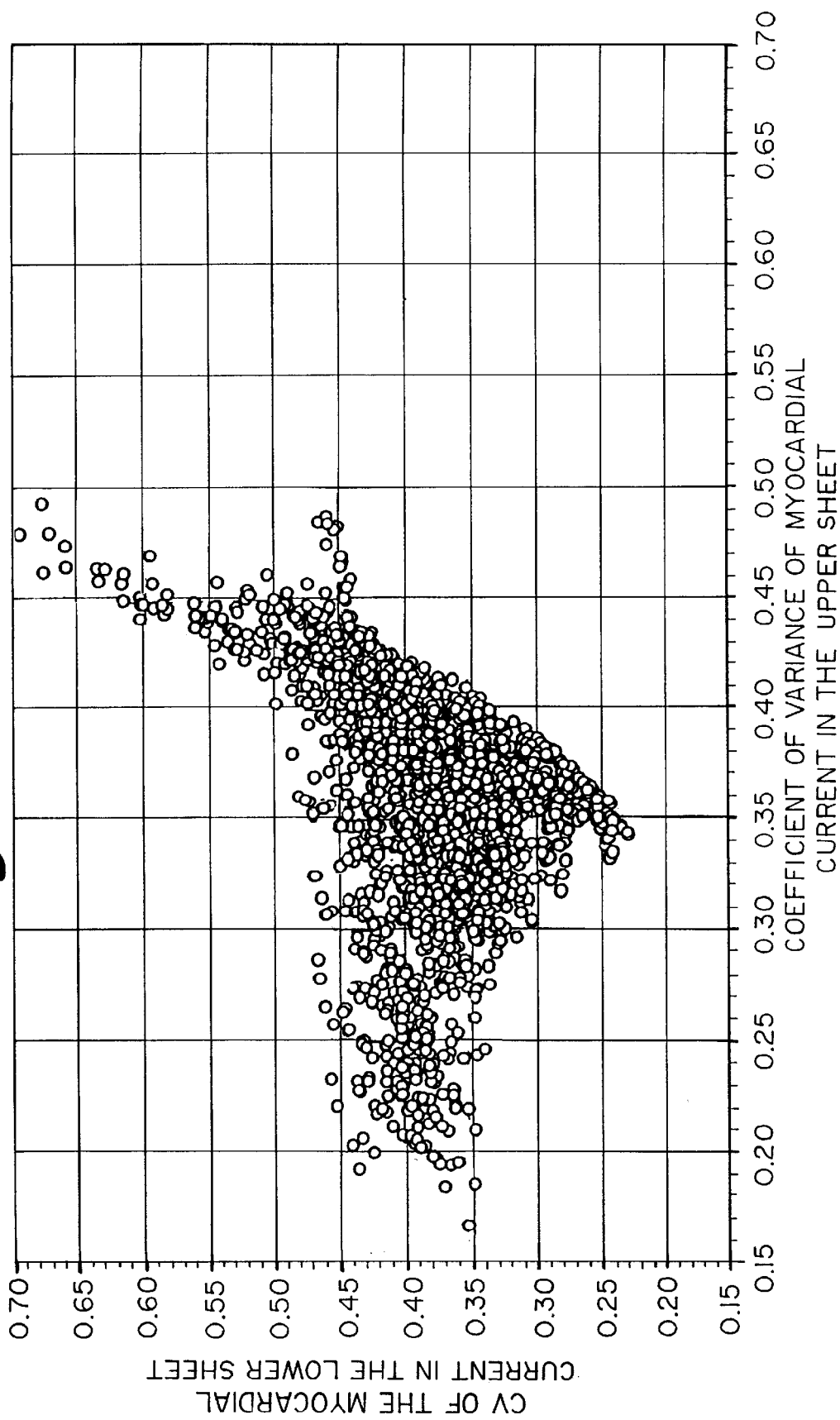
Figure 67H:
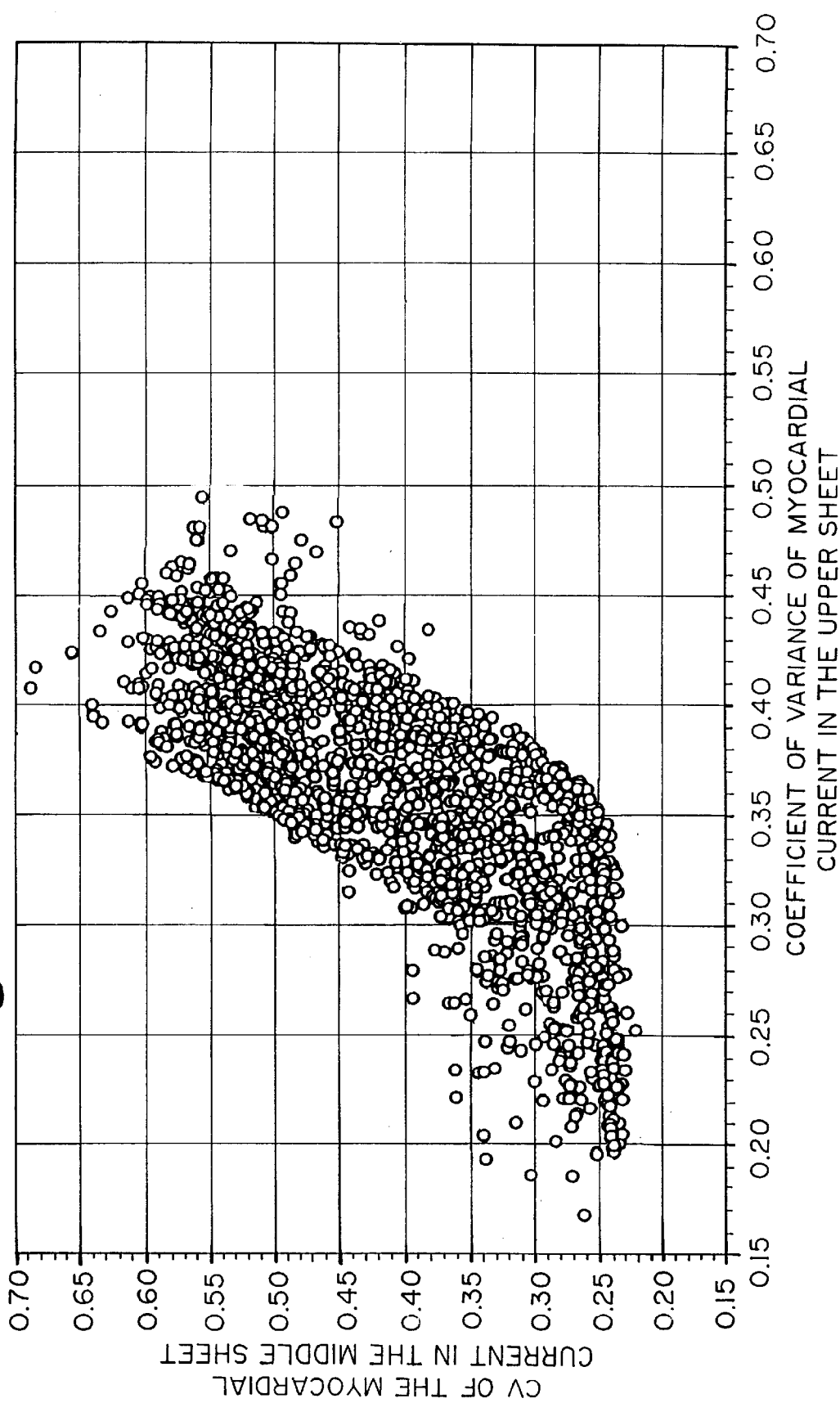
Figure 68A:
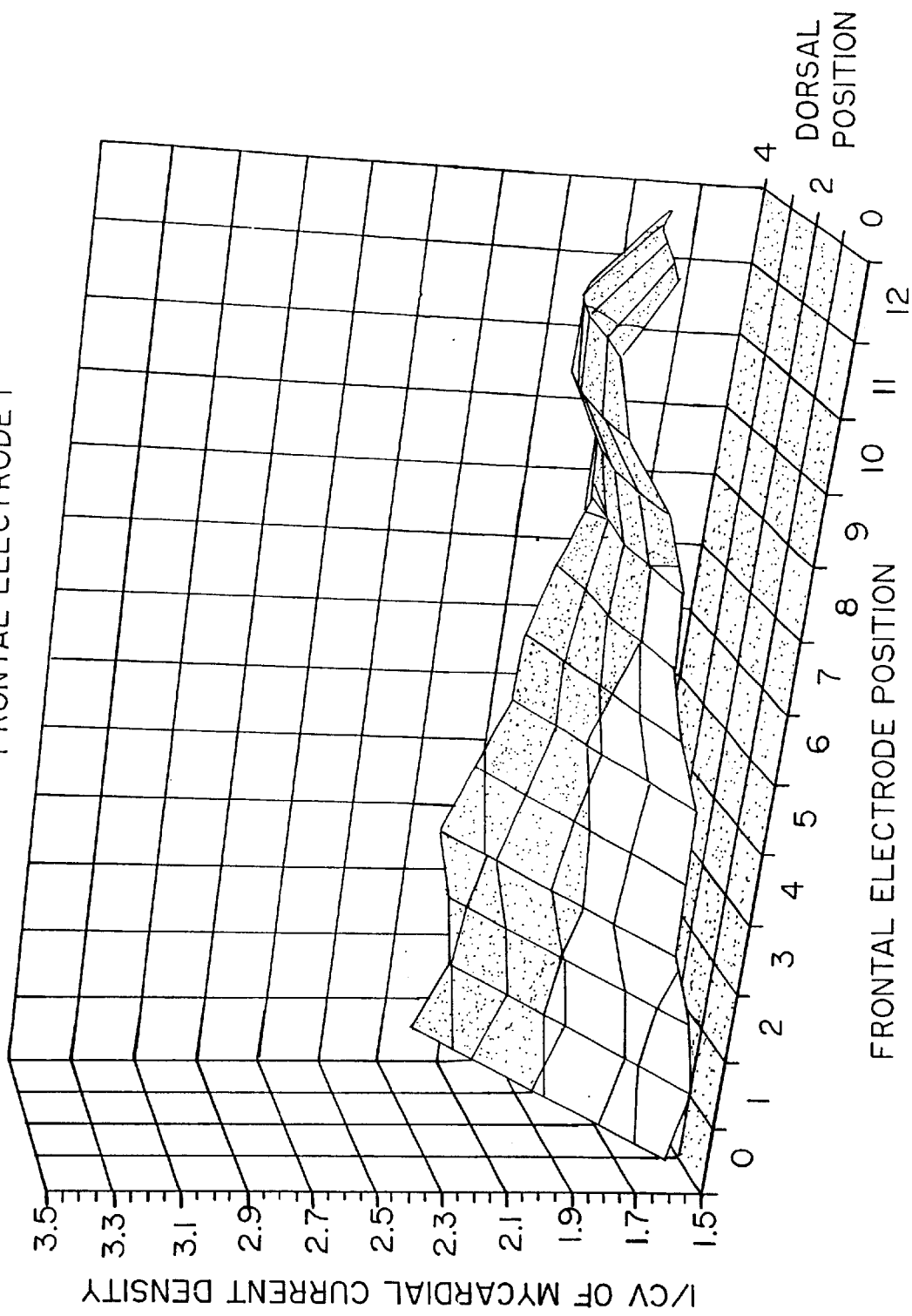
Figure 68B:
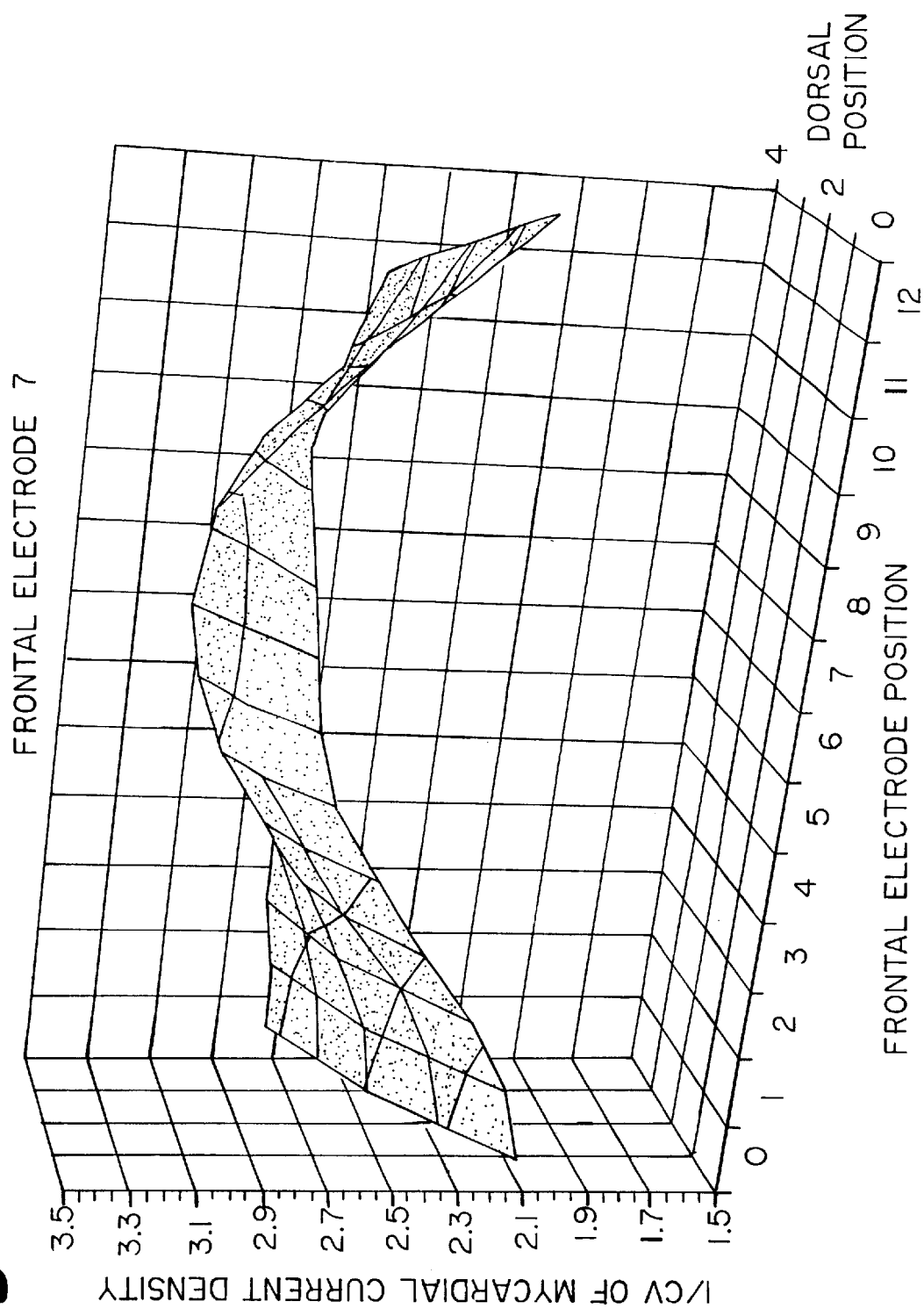
Figure 68D:
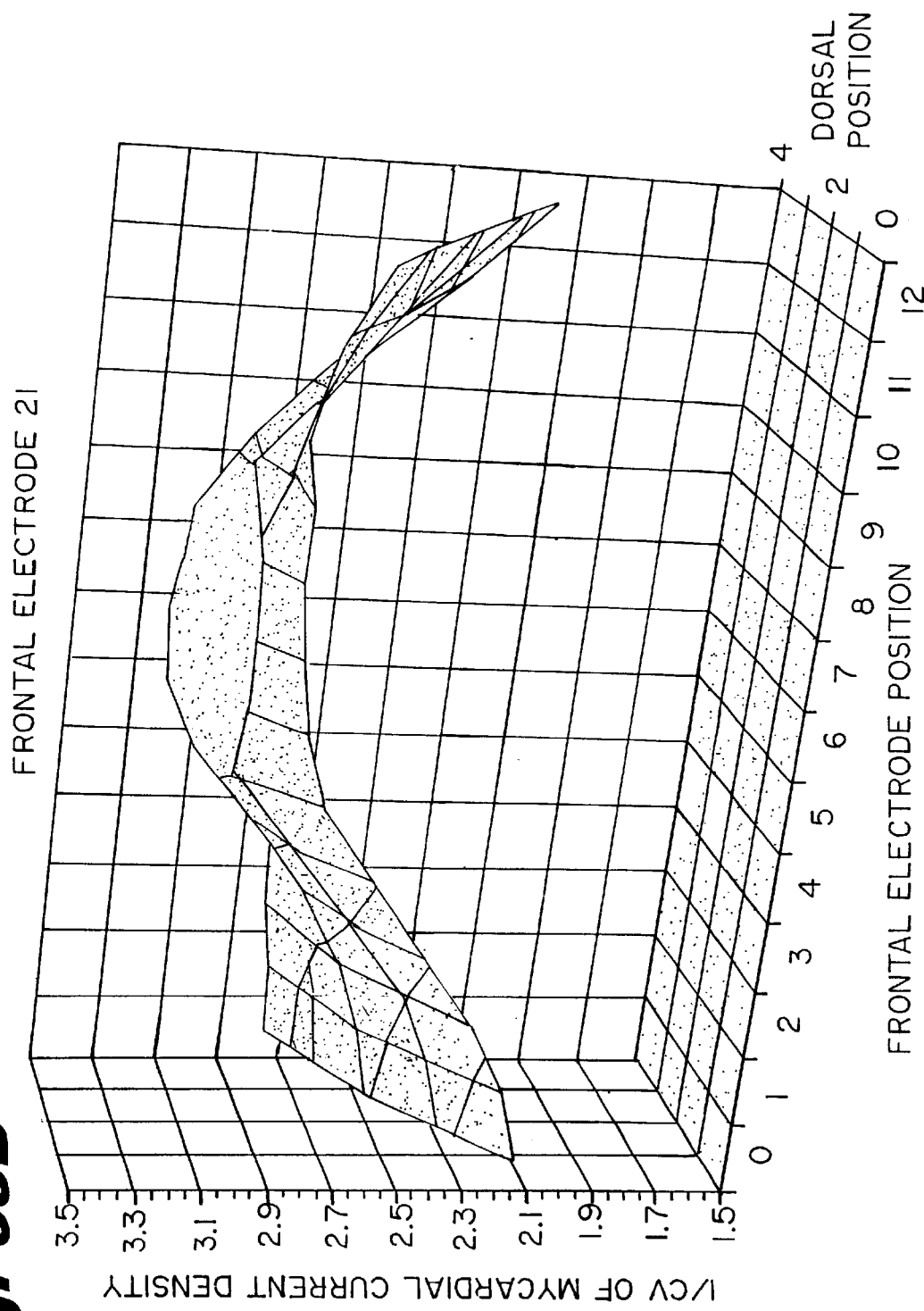
Figure 68E:
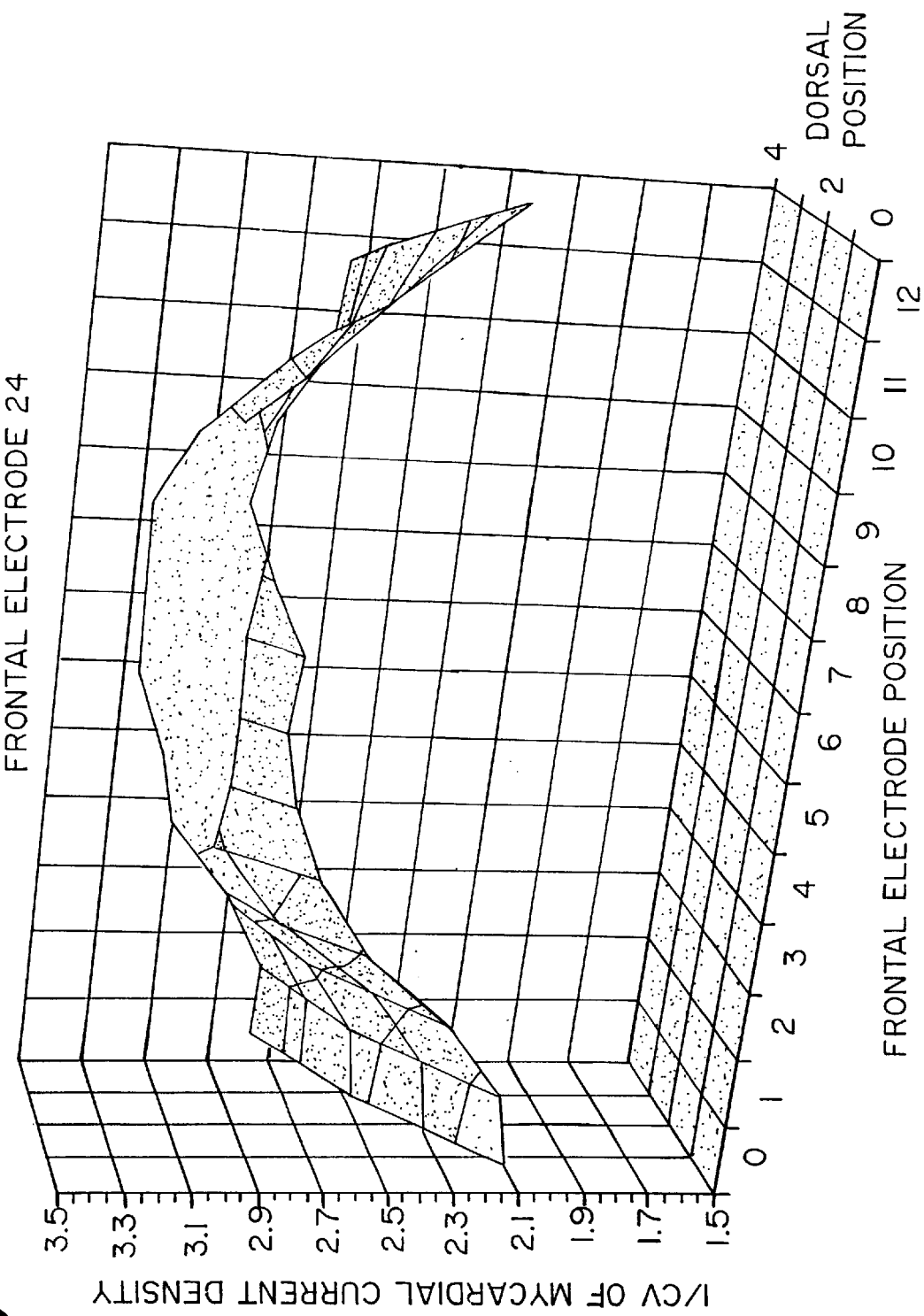
Figure 68F:
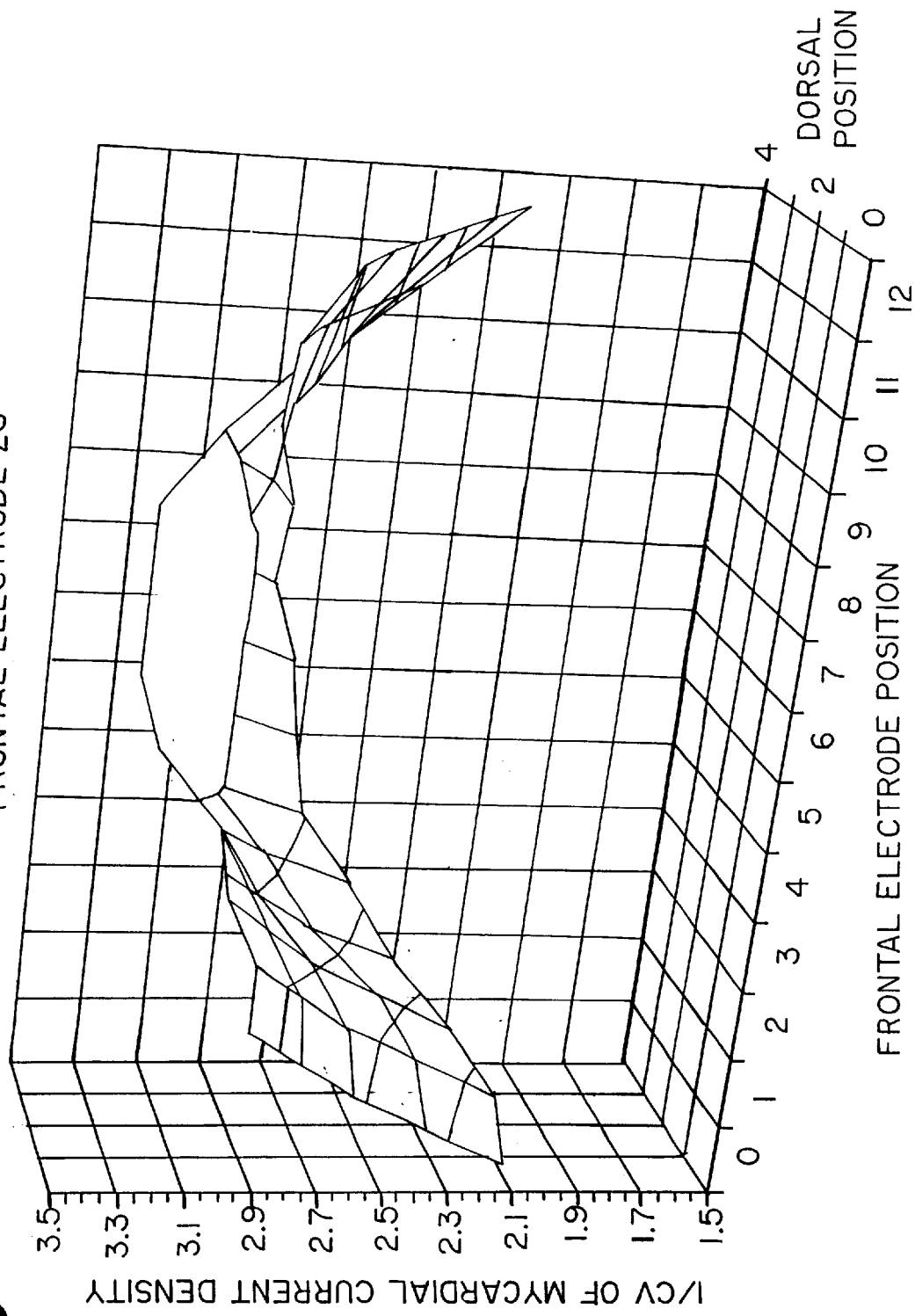
Figure 68G:
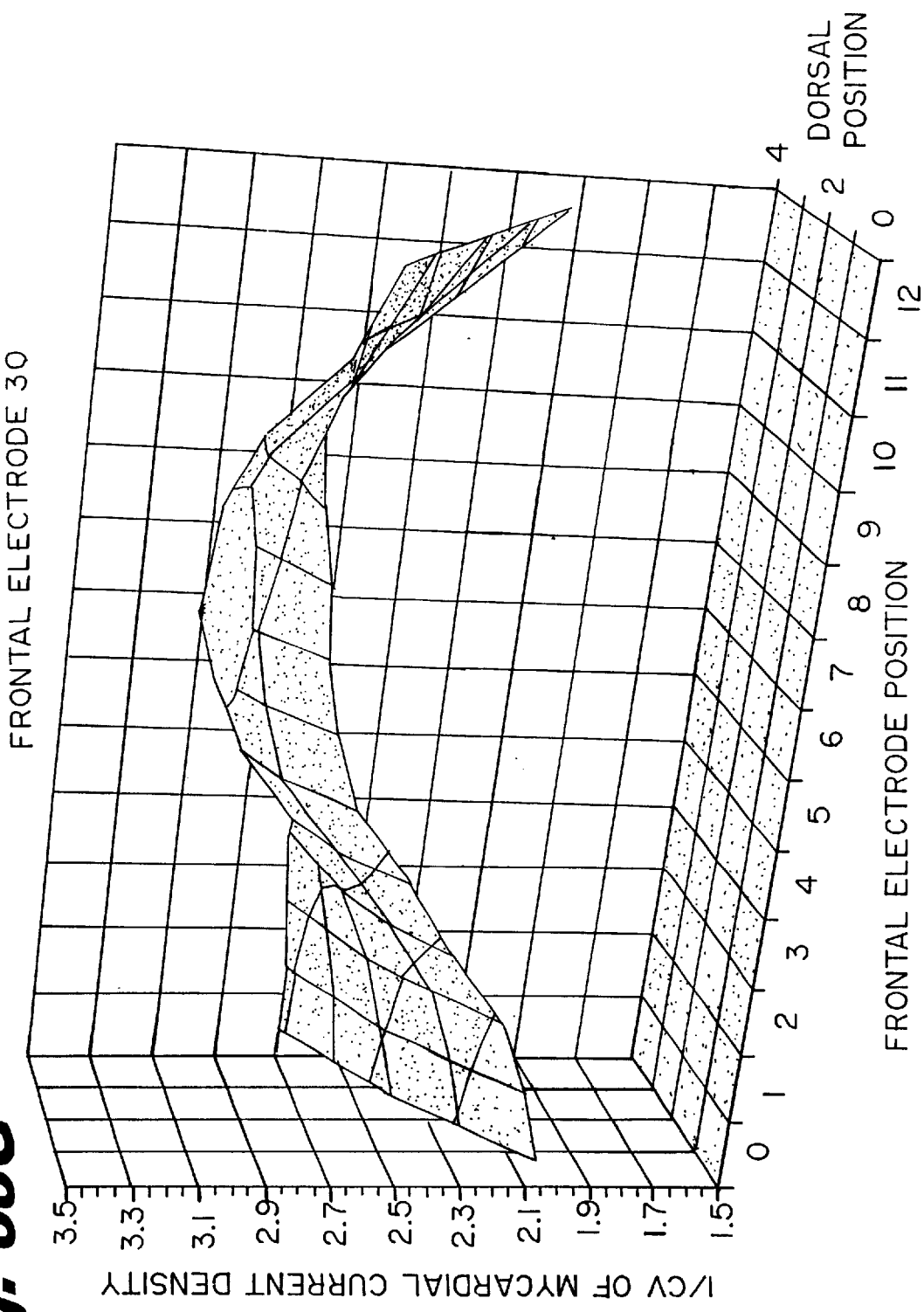
Figure 69:
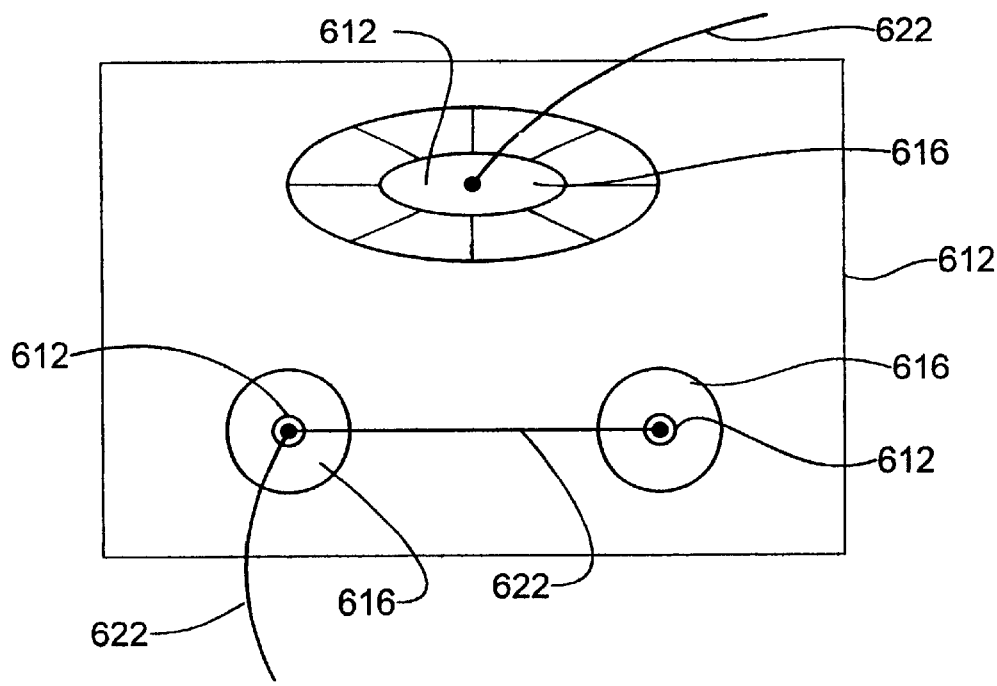
FIG. 69 depicts one embodiment of the present invention comprising a stimulation lead or electrode.
Figure 72:
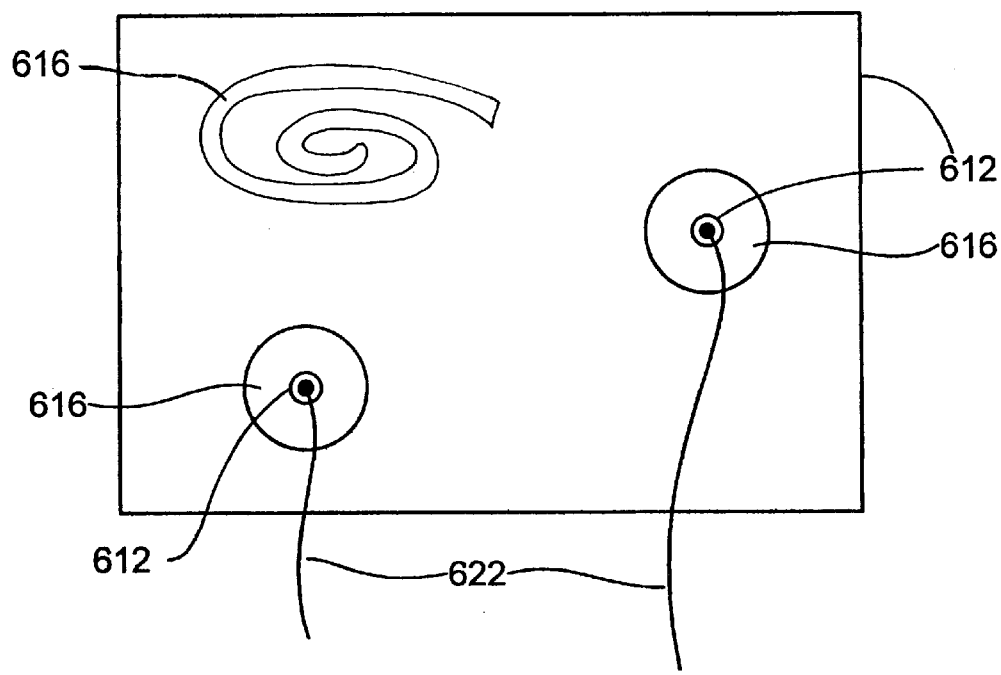
FIG. 72 depicts one embodiment of the present invention comprising a stimulation lead or electrode.
Figure 71A:
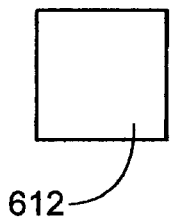
FIGS. 71A–F depict various embodiments of the present invention comprising stimulation leads or electrodes.
Figure 71B:
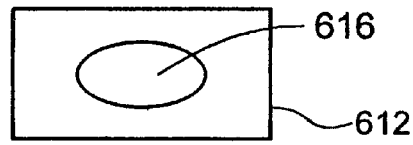
Figure 71C:
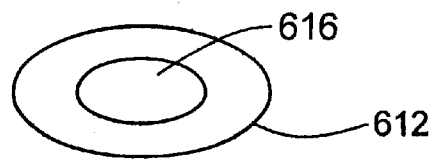
Figure 71D:
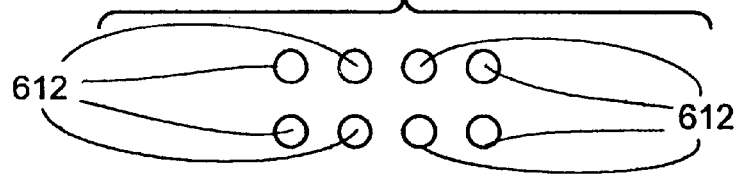
Figure 71E:
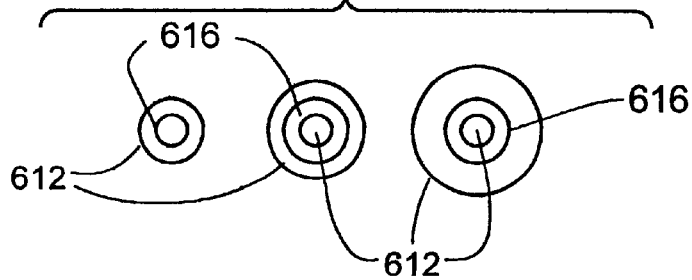
Figure 71F:
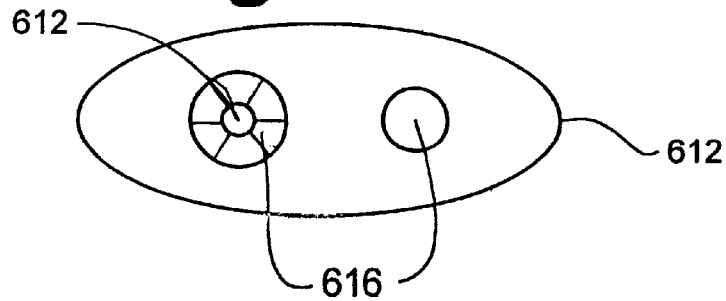

The cross sections were scanned digitally and converted into color bit map images that were manually edited in order to achieve suitable distinction of different morphologies. Color images of the bit maps that were obtained in this way are shown in FIGS. 64A–C. FIGS. 64A–C depict images, which include the following cross-sections, ventricular myocardium 510, atrial myocardium 520, lungs 530, bones 540, cartilage 550, muscle layers 560 fat and cutanous tissue 570, esophagus 580, liver 590 and blood 600. It should be noted that the cross sections were taken form the orientation used in the original atlas and hence correspond to the view caudo-cranial rather than cranio-caudal.

The images of the cross sections shown in FIGS. 64A–C also show the possible positioning of electrodes considered in individual modeling studies. These are shown in cyan line 610 on the frontal and dorsal part of each cross section.

The individual tissue types were assigned electrical resistances that are listed in the table in FIG. 65. The table contains values in technical units and their absolute numbers are meaningless. Nevertheless, the relationship between these individual resistance characteristics corresponds to the relationship between electrical resistance of true tissue types. Individual tissue structures were considered homogenous. In particular, no difference between the electrical resistance of the myocardium in respect of fiber orientation was introduced.

The model was implemented on an advanced model of a personal work-station that was equipped, with a 450 MHz Pentium II processor. The resolution of the bit map images shown in FIGS. 64A–C was not compromised and each pixel in these images was considered as a separate nod of three individual 2-D conduction models. The total sheet used in each model was 704×464 nodes and correspondingly the resolution of the model was approximately in 0.5 mm steps. Taking all the three cross sections together, the tissue of ventricular myocardium was modeled by more than 79,000 individual nodes.

The model was implemented as a grid of electrically conductive rectangular mesh with individual resistance values assigned to individual nodes rather than connectors. These corresponded to the resistance constants as introduced for each tissue type considered.

When introducing simulated electrodes on the frontal and dorsal part of the model, electrical current passing through the structures of individual sheets was computed according to the Kirkhoff laws by the standard finite difference method. In more detail, the Kirkhoff laws were used to describe each of the 2-D models by a set of linear equations with as many variables as non-empty nodes in each sheet. The set of such equations was solved by GaussJordan elimination method and the distribution of potential was obtained for each computational experiment.

In each experiment, the potential of the front electrode introduced into the computational experiment was considered to equal to zero while the potential of the electrode simulating the dorsal part was considered to equal to one on a hypothetical voltage distribution scale. From these two potentials, the voltage distribution across each whole sheet of the model was computed and the voltage differences between neighboring nodes were, together with their resistance constants, used to calculate the current density for each node of the model.

The values of the current densities obtained for the ventricular myocardium were considered and statistically evaluated for each electrode combination.

Compared to the defibrillation models which aim at achieving a minimum current density in a pre-specified percentage of myocardial tissue, the concepts involved in simulating the optimum electrode positioning for the induction of Wedensky phenomenon is different. The phenomenon relies of sub-threshold stimulation and should therefore be ideally introduced with the same level of sub-threshold current density in the whole myocardium. Since the level of the current density can be made variable by introducing different voltage gradient between the frontal and dorsal electrodes the optimum position of the electrodes will be such that the variance of the myocardial current density is the lowest. In practice, this means trying to identify such a combination of frontal and dorsal electrodes which will lead to the lowest coefficient of a variance (i.e. the standard deviation divided the mean) of myocardial current densities. This approach was used in this modeling study.

Since the dorsal patch is unlikely to have a very significant effect of the efficacy of the system, a simple 15 cm continuous patch was considered in five different positions starting at the very right edge of the dorsal electrode area. (Note that the area for electrode placement of the three sheets of the model correspond fairly each to the other.) This position at the very right edge was termed "Position 0" and was further shifted in steps of simulated 2 cm. Positions 1 to 4 (shifted by 2 to 8 simulated centimeters) were obtained in this way.

In a similar manner, the positioning of the frontal electrode was introduced. Thirteen different positions of an electrode were considered. Position 0 again corresponded to the very right edge of the frontal electrode areas and further 12 positions were introduced by shifting the original position by simulated 7½ mm. The frontal positions of the electrode were combined with 30 different shapes of the electrodes. Shapes of electrodes similar to the ones utilized herein are depicted in FIGS. 69, 70A–E, 71A–F and 72 The sizes of the electrodes in this appendix are listed in bitmap pixels of the model which approximately correspond to 0.5 mm. Thus, the largest electrode considered was the electrode 7 which corresponded to a 12 cm long continuous patch.

As it can be seen in FIG. 66, electrodes 1 to 7 were composed of one solid segment and modeled differently only single patches. Electrodes 8 to 21 were composed of two segments and thus corresponded to a patch with one perforation (the sizes of the segment of the patch as well as the sizes of the perforation differed in these electrodes). Similarly, electrodes 22 to 26 were composed of three different segments, electrodes 27 to 29 of four difference segments and finally the electrode 30 of five different segments (that is a model of a patch with four individual perforations).

All the different possibilities of the dorsal patch in positions 0 to 4 were combined with all different electrode shapes 1 to 30 in frontal electrode positions 0 to 12 and were considered for each sheet of the model. That is, for each sheet of the model, 1,950 individual computational experiments were performed and for each of these experiments, the mean and standard deviation of the myocardial current density was obtained both for the individual sheets as well as for the composition of the myocardial tissue combining all the three sheets together.

Graphical summaries of the individual results obtained in the whole set of 1,950 experiments are shown in FIGS. 67A–H. It is obvious that there are remarkable differences not only between individual electrodes positioning but also between the three sheets of the model. Therefore the composite values which consider all three sheets of the model together are most representative and will be further relied on in the subsequent analyses.

FIGS. 68A–G shows the individual values of the coefficient of variance of myocardial current density obtained for individual electrode configuration and positioning. The individual sheets of FIGS. 68A–G correspond to the individual shapes of the frontal electrode while the variability in their positioning is depicted in the 3-D graphs. Rather than showing the values of the coefficient of variance, the graphs of FIGS. 68A–G show their reciprocal values. This the higher values, the better for the performance of a Wedensky induction system.

It can be clearly seen that the larger the area occupied by the electrode, the better its performance. The best results were obtained with the shapes of the electrode 19 and 24, followed by the shape 28 and finally followed by the shape 7. The differences are not very large but it should also be noted that the stability ol the electrodes modeling a very large patch with perforations (e.g. shapes 19 and 24) are more stable in terms of achieving very low coefficient of variance of the myocardial current density for different frontal positionings. Electrode 7 which models the large single patch is without any perforation is less efficient in this respect.

It should be also noted that the coefficient of variance of the myocardial current decreases from electrode shape 1 to electrode shape 7 dramatically which suggests that for achieving a low coefficient of variance of the myocardial current density, one should use a rather large precordial patch.

It should also be noted that the variability in both mean and standard deviation of the myocardial current density introduced by varying either the frontal electrode position or the frontal electrode shape and different dorsal position is considerable.

The model is of course very restricted since it is based only on the three individual sheets and does not include the true 3-D structure of the heart and thorax which would be needed for a more accurate prediction of the effects of different electrode positionings. Nevertheless, even from this restricted set of experiments, significant conclusions may be drawn.

For the optimum induction of Wedensky phenomenon in man, a rather large frontal electrode should be used. The electrodes presently available of the experiments performed by Harbinger Medical seem to be appropriate for this purpose.

Since the differences between the solid patch front electrodes and perforated path front electrodes seen in the model were rather negligible, current experimenting performed by Harbinger Medical should be continued with the presently available electrode design. The observation of the model should be tested that a more pronounced induction of the Wedensky phenomenon will be achieved when placing the frontal electrode more medially than laterally.

Additional embodiments of the invention also consider perforated frontal electrodes. The model suggests that a large electrode composed of two segments with a larger center opening was the optimum in this two 2-D study. Probably, electrodes composed of several large squares with openings of about 2 cm in-between would correspond most to the model prediction.

As previously discussed, various means of optimizing the noninvasive detection and localization of potential or actual sites of arrhythmias are possible and hereby enabled. In addition to the embodiments disclosed previously, it is possible to enhance this invention by careful electrode design, location, configuration, size, and current delivery means. For example as depicted in FIGS. 69, 70A–E, 71A–F and 72, one or more energy delivery electrodes 612 of any shape having one or more holes 616 of various similar sizes and positions may be employed. Holes or apertures 616 in the electrode 612 may be empty or have an electrically (or magnetically) nonconducting material in them. If these holes are material filled, this material may also have one or more holes as described above which are filled with energy delivery electrode material 618. Any energy delivery material can be connected to a dedicated energy delivery wire, or, some or all of the energy delivery material within an electrode can be electrically connected with other material within the same electrode. This pattern of holes-nonconducting material-holes-nonconducting material, etc., and various connections described above may be repeated either symmetrically or asymmetrically according to the application.

In yet another embodiment, a plurality of small electrodes may be substituted instead of a singular large electrode in order to properly and more accurately deliver energy. Such small electrodes may deliver energy simultaneously or separately under hardware and/or software control. FIGS. 69, 70A–E, 71A–F and 72 illustrate various embodiments of the above disclosures. For example, in these figures element 12 represents a stimulation lead or electrode having one or more holes or apertures 16 consisting of nonconducting material, and energy delivery wires or similar energy delivery means 22.

These embodiments of the invention, utilizing portions of nonconducting material within the normal periphery of stimulation leads or electrodes, may actually result in substantial increases in energy performance of these materials. This optimizes field shaping and current delivery to the subject. This technique may also facilitate the staging of current among leads in sequential, seriatim or another pattern of energy delivery not normally used or associated with this diagnostic procedure. In one example, this staging of current may facilitate optimization in some form of synchronization with the cardiac sinus rhythm or other bodily rhythm.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations which fall within the spirit and broad scope of the invention.

What is claimed is:

1. A method for detecting patient susceptibility to arrhythmias comprising the steps of:
   providing means for injecting low level electromagnetic energy stimulations into a patient's body suitable to alter at least one cardiac signal to allow a comparison of acquired distinguishable signal differences with at least one other cardiac signal which has not been affected by said injected energy;
   connecting a lead system for both sensing the cardiac signals and delivering the injected energy to said means for injecting low level electromagnetic energy into the patient's body, said lead system, comprising a plurality of energy sensing and energy delivery leads and a plurality of energy sensing and energy delivery electrodes;
   applying the electrodes, connected to said lead system, to the patient's body;
   optimizing the electrodes to induce Wedensky phenomena;
   utilizing sensing improvement means for improving the quality of the sensed electromagnetic energy during the stimulation and acquisition process; and
   evaluating the sensed signal for one- or more arrhythmia predictive factors selected from a group consisting of: heart rate variability, QRST timing changes, ST segment elevation and T wave changes.

2. The method of claim 1 in which the sensed cardiac signal is evaluated for change in intervals between reoccurring activity in the heart whereby cardiovascular and autonomic condition are studied.

3. The method of claim 1, in which the sensed cardiac signal is evaluated for changes occurring between an S-wave and a T-wave whereby cardiovascular and autonomic condition are studied.

4. The method of claim 1, which the sensed cardiac signal is evaluated for changes occurring between an S-wave and a subsequent heartbeat whereby cardiovascular and autonomic condition are studied.

5. The method of claim 1, in which said sensing improvement means comprises wavelet processing.

6. The method of claim 5 in which the wavelet processing comprises the steps of:
   accepting two orthogonal XYZ signal averaged ECG signals along with any parameters required to perform the remaining analysis;
   processing a region of interest of the two signals into individual wavelet surfaces using the Morlet wavelet;
   mathematically combining the two wavelet surfaces to form a wavelet residuum;
   calculating the surface area of the region of interest within the wavelet residuum;
   calculating local maxima of the two wavelet surfaces; and
   returning the surface area calculation and count of local maxima.

7. A method for assessing heart characteristics comprising the steps of:
   providing means for injecting low level electromagnetic energy stimulations into a patient's body suitable to alter at least one cardiac signal to allow a comparison of acquired distinguishable signal differences with at least one other cardiac signal which has not been affected by said injected energy;
   connecting a lead system for both sensing the cardiac signals and delivering the injected energy to said means for injecting low level electromagnetic energy into the patient's body, said lead system, comprising a plurality of energy sensing and energy delivery leads;
   applying electrodes, connected to said lead system, to the patient's body;
   optimizing the electrodes to induce Wedensky phenomena; and
   utilizing sensing improvement means for improving the quality of the sensed electromagnetic energy during the stimulation and acquisition process.

8. The method of claim 7 wherein the electrodes are optimized by increasing surface area of the at least one electrode relative to the other electrodes.

9. The method of claim 7 in which the electrodes are optimized by including one or more perforations through at least one of said electrodes.

10. The method of claim 9 in which one or more perforations are filled with a nonconducting material.

11. The method of claim 7 which the electrodes are optimized by including portions of nonconducting material within the periphery of at least one electrode.

12. The method of claim 11 in which the one or more electrode material portions are operably interconnected.

13. The method of claim 11 in which the one or more electrode material portions are individually connected to the lead system.

14. The method of claim 7 in which the electrodes are optimized by including at least one electrode having one or more electrode material portions and one or more nonconducting material portions and wherein said electrode material portions and nonconducting material portions are disposed alternately about a center position.

15. The method of claim 7 in which the electrodes are optimized by shaping them as annuli.

16. The method of claim 15 in which at least one annulus is filled with a nonconducting material.

17. The method of claim 7 in which the electrodes are optimized by utilizing a plurality of small electrodes.

18. The method of claim 7 in which the electrodes are optimized by forming the electrodes as annuli concentric about a circle of electrode material alternating annuli of nonconducting material therebetween.

19. The method of claim 7 in which the electrodes are optimized by forming the electrodes as a circle of nonconducting material surrounded by alternating concentric annuli of electrode material alternating with annuli of nonconducting material.

20. The method of claim 7 in which at least one electrode is optimized by including one or more perforations therethrough and at least one annular perforation therethrough.

21. The method of claim 7 in which the electrodes are optimized by including a plurality of annular perforations each having an island of electrode material in the center thereof.

22. The method of claim 21 in which the perforations are filled with a nonconductive material.

23. The method of claim 7 in which the electrodes are optimized by including a plurality of annular perforations each having an island of electrode in the center thereof, in which some islands are connected to a first lead and other islands are connected to a second lead of said lead system and further including a spiral shaped perforation therethrough.

24. The method of claim 23, in which the perforations are filled with a nonconducting material.

25. An electrode set comprising a plurality of electrodes wherein the electrodes are optimized to induce Wedensky phenomena by sub-threshold transcutaneous stimulation, the Wedensky phenomenon induction optimizing characteristics selected from a group consisting of: size, shape, presence of perforations, configuration of perforations and any combination thereof.

26. The electrode set as claimed in claim 25, comprising at least one electrode of increased surface area relative to other electrodes in the electrode set.

27. The electrode set as claimed in claim 25, comprising at least one electrode including one or more perforations therethrough.

28. The electrode set as claimed in claim 27, in which one or more perforations are filled with a nonconducting material.

29. The electrode set as claimed in claim 28, in which the at least one electrode comprises one or more electrode material portions that are electrically interconnected.

30. The electrode set as claimed in claim 28, in which the at least one electrode comprises one or more electrode material portions that are individually connected to the lead system.

31. The electrode set as claimed in claim 25, comprising at least one electrode including portions of nonconducting material within the periphery thereof.

32. The electrode set as claimed in claim 25, in which at least one of the electrodes comprises one or more electrode material portions and one or more nonconducting material portions wherein said electrode material portions and nonconducting material portions are disposed alternately about a center position in at least one electrode.

33. The electrode set as claimed in claim 25, in which at least one of the electrodes is annular in shape.

34. The electrode set as claimed in claim 33, in which the annular electrode is filled with nonconductive material.

35. The electrode set as claimed in claim 25, which a subset of the plurality of electrodes comprises a second lesser plurality of small electrodes, the lesser plurality of small electrodes connected to a single lead.

36. The electrode set as claimed in 25, claim comprising a center portion of electrode material surrounded by concentric annuli of electrode material alternating with annuli of nonconducting material therebetween.

37. The electrode set as claimed in claim 25, comprising a center portion of nonconducting material surrounded by concentric annuli of electrode material alternating with annuli of nonconducting material therebetween.

38. The electrode set as claimed in claim 25, comprising electrode material including a plurality of annular perforations therethrough each annular perforation having a portion of electrode material in which some portions are connected to a first lead and other portions are connected to a second lead.

39. The electrode set as claimed in claim 38, in which the perforations are filled with nonconducting material.

* * * * *